US006825199B2

(12) United States Patent
Domagala et al.

(10) Patent No.: US 6,825,199 B2
(45) Date of Patent: Nov. 30, 2004

(54) 7-SUBSTITUTED QUINAZOLIN-2,4-DIONES USEFUL AS ANTIBACTERIAL AGENTS

(75) Inventors: John Michael Domagala, Canton, MI (US); Edmund Lee Ellsworth, Brighton, MI (US); Liren Huang, Edmonton (CA); Thomas Eric Renau, Santa Clara, CA (US); Rajeshwar Singh, Edmonton (CA); Michael Andrew Stier, Ypsilanti, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/971,343

(22) Filed: Oct. 4, 2001

(65) Prior Publication Data

US 2002/0115674 A1 Aug. 22, 2002

Related U.S. Application Data

(62) Division of application No. 09/508,796, filed as application No. PCT/US98/19877 on Sep. 23, 1998, now Pat. No. 6,331,538.

(60) Provisional application No. 60/063,556, filed on Oct. 28, 1997, and provisional application No. 60/098,588, filed on Aug. 31, 1998.

(51) Int. Cl.[7] .................... C07D 239/96; C07D 403/04; C07D 471/06; C07D 471/04; A61K 31/505

(52) U.S. Cl. ................... 514/252.16; 544/279; 514/258

(58) Field of Search .......................... 544/279; 514/258, 514/252.16

(56) References Cited

U.S. PATENT DOCUMENTS 5,283,248 A 2/1994 Hubschwerlen et al. .... 514/267

FOREIGN PATENT DOCUMENTS

| | | |
|---|---|---|
| DE | 1068263 | 11/1959 |
| EP | 0316630 | 5/1989 |
| JP | 491090 | 3/1992 |

OTHER PUBLICATIONS

Ghoneim et al. Novel 2–substituted aminonicotinhydroxaminc acids, Egypt. J. Pharm., 1987.*

Eckstein et al. A facile rearrangement of pyridinecarbohydroxamic acids in formamide, Heterocycles, 20: 1899–1901.*

Cianci et al., "Identification of N–hydroxamic acid and N–hydroxy–imide compounds that inhibit the influenza virus polymerase", *Antiviral Chemistry & Chemotherapy*, vol. 7, No. 6, 1996, pp 353–360.

Ghoneim et al., "Nove 1 2–Substituted Aminonicotinhydroxamide Acids", *Egypt J. Pharm*, vol. 28, No. 1–4, 1987, pp 9–16.

Eckstein, et al., "A fa cile rearrangement of *Heterocycles*, pyridinecarbohydroxamic acids in formamide", vol. 20, No. 10, 1983, pp 1899–1901.

Tserng, et al., "El ectron–Impact Induced Fragmentation of 3–Hydroxy Quinazoline–2,4(1H,3H)dione, Pyridopyrimidine–2,4(1H,3H)diones, Lumazine and Alloxazine", *J. Het Chem.*, vol. 12, No. 1, 1975, pp 79–83.

Schapira and Lamdan, "C yclic Hydroxamic Acids Derived from Quinazoline", *I. Het. Chem.*, vol. 9, No. 3, 1972, pp 569–576.

Reddy, et al., "Une xpected formation of cyclic hydroxamic acids from O–(2–aminobenzoyl)hydroxylamine", *Synth. Commun.*, vol. 26, No. 15, 1996, pp 2843–2846.

Grochowski and Boles awska, "Appl ication of quaternary phosphonium salts in alkylation and acylation of N–hydroxylactams", *Pol I Chem*, vol. 55, No. 3, 1981, pp 615–621.

Kobashi et al., "Effe ct of acyl residues of hydroxamic acids on urease inhibition", *Biochim. Biophys. Acta*, vol. 227, No. 2, 1971, pp 429–441.

Kühl e and Wegler, "Zur Ke nntnis der N–hydroxy–dicarbonsäuerimide und ihrer O–Sulfonylverbindungen, einer neuen Klasse organisher Fungizide", *Ann. (Jutus Liebigs Ann. Chem.)*, vol. 616, 1958, pp 183–206.

Taniyama and Yasui, "St udies on Chemotherapeutics for *Mycobacterium tuberculosis*. XXI. On the Rearrangement Reaction of Thiazolidinone Hydroxamic Acid Derivatives", *Yakugaku Zasshi*, vol. 81, No. 3, 1961, pp 427–430.

Hurd, et al., "Suc cino– and phthalo–hydroxamic acids", *J. Org. Chem.*, vol. 19, 1954, pp. 1140–1149.

Jacini, "La reazione de Baeyer del diossindolo con acido nitroso", *Gazz Chim. Ital*, vol. 74, 1944, pp 3–12.

Jacini, "R icerche sulla reazione tra isatina e ammo–niaca", *Gazz. Chim Ital*, vol. 77, 1947, pp 295–308.

Chu et al., "St ructure–activity relationship of quinolone antibacterial agents: the effects of C–2 substitution", *Drugs Exptl. Clin. Res.*, vol. 16, No. 5, 1990, pp 215–224.

Ortwine et al., "Ge neration of N–Methyl–D–aspartate Agonist and Competitive Antagonist Pharmacophore Models. Design and Synthesis of Phosphonoalkyl–Substituted Tetrahydroisoquinolines as Novel Antagonists" *J. Med. Chem*, vol. 35, No. 8, 1992, pp 1345–1370.

Gmünde r et al., "Effect of Pyrimido[1,6–a]Benzimidazoles, Quinolones, and $Ca^{2+}$ on the DNA Gyrase–Mediated Cleavage Reaction", *Antimicrob. Agents Chemother.*, vol. 39, No. 1, 1995, pp 163–169.

Cas printout for Cianci et al., Jan. 1996.

Cas printout for Connor et al., Jan. 1996.

* cited by examiner

*Primary Examiner*—Richard L. Raymond
*Assistant Examiner*—Hong Liu
(74) *Attorney, Agent, or Firm*—Heidi Berven

(57) ABSTRACT

The invention is a series of 7-substituted quinazolin-2,4-diones useful as antibacterial agents, processes for the preparation of the compounds, and a pharmaceutical composition containing one or more of the compounds.

15 Claims, No Drawings

7-SUBSTITUTED QUINAZOLIN-2,4-DIONES USEFUL AS ANTIBACTERIAL AGENTS

This is a division of application Ser. No. 09/508,796, filed Mar. 15, 2000 now U.S. Pat. No. 6,331,538, which was the National Stage of International Application No. PCT/US98/19877 filed Sep. 23, 1998. This application claims of U.S. Provisional Application No. 60/063,556, filed Oct. 28, 1997, and U.S. Provisional Application No. 60/098,588, filed Aug. 31, 1998.

BACKGROUND OF THE INVENTION

Antibiotic resistance is a worldwide problem (*J. Med. Chem.*, 1996;39:3853) with catastrophic potential (*Southern Med. J.*, 1995;88:797). In 1995, the American Society of Microbiology Task Force issued a report defining the resistance problem and calling for new antibacterial agents with novel structures or mechanisms to offer alternatives to existing therapeutic choices.

The quinolone antibacterials as exemplified by ciprofloxacin 1 represent a significant addition to the therapeutic options currently available. The quinolones are potent, inhibit gram positive and gram negative bacteria, and may be administered orally or IV. The quinolones also have several significant side effects (*J. Antimicrob. Chemother.*, 1994;33:685), and significant resistance has been frequently noted (Gootz, *Medicinal Research*, 1996;Rev. 16:433).

1

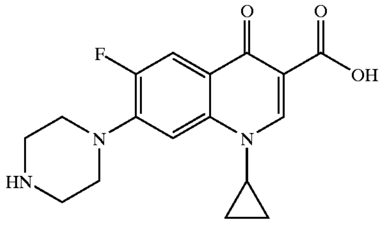

The quinolones have a distinct structure activity relationship which has been defined by several thousands of analogs prepared over the last 30 years (*Progress in Drug Research*, Editor S. Mitsuhashi, 1992;38:11–147). In the quinolone SAR, it is well-established that the $N_1$ group with the $C_3$-carboxyl and the $C_4$ carbonyl are essential for activity and that any substituents at $C_2$ detract from activity (*J. Antimicrob. Chemother.*, 1994;33:685 and Gootz, supra., 1996). It is also well-established that $R_6$ is ideally fluorine, and that $R_7$ is a nitrogen containing heterocycle. $R_1$ is ideally a small alkyl, cycloalkyl, or a phenyl group.

2

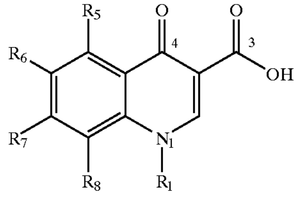

The quinolones inhibit bacterial growth by inhibition of DNA gyrase and Topoisomerase IV (Gootz, supra., 1996). The gyrase interaction appears to rely on the $N_1$—$C_4$-carbonyl-$C_3$-carboxyl relationship.

Attempts to design novel quinolone mimics have focused on the $N_1$—$C_4$-carbonyl-$C_3$-carboxyl relationship. Compounds of type 3 were designed to keep an all planar relationship and to have the NH of the isothiazole ring be as acidic as the quinolone $CO_2H$ (*Chu, Drugs Exptl. Clin. Res.*, 1990;16:215). While maintaining excellent quinolone activity, these compounds also showed antitumor and mammalian topoisomerase activity (*Drugs of the Future*, 1992;17:1101) which is undesired in an antibacterial agent.

3

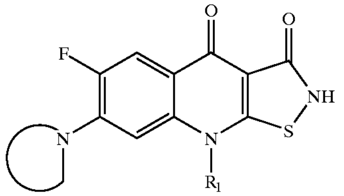

Several publications (U.S. Pat. No. 5,283,248; *J. Med. Chem.*, 1992;35:1358; *Antimicrob. Agents Chemother.*, 1995;39:163) cite compounds of type 4 as having antibacterial activity and inhibition of DNA gyrase. In compounds 4, the relationship of the $N_1$ to the $C_4$ carbonyl has been skewed. Compounds of type 4 were also ineffective against bacteria that were quinolone resistant.

4

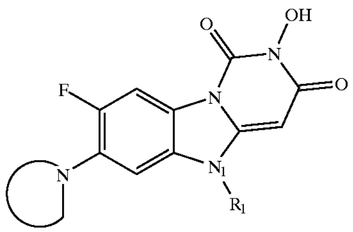

Compounds of type 5 have also been revealed as quinolone mimics (JP 4,091,090 March 1992; Interscience Conference on Antimicrobial Agents and Chemotherapy 1991, Abstract 1494). These agents were reported to possess antibacterial and gyrase activity. While the ideal $N_1$—$C_4$-carbonyl relationship is maintained in 5, the $C_2$ region where substitution is undesirable in the quinolones is filled with a major part of the ring. None of the quinolone mimics 3–5 exactly mimics the quinolone parent structure because all contain an extra third ring used to deliver the acidic H group required for activity.

WO 96/04288 describes a series of benzoheterocycles 6 which are glycine receptor antagonists. X, Y, and Z are chosen to provide hydrogen bond acceptor and donator groups. Among the compounds depicted are some N-hydroxy-quinazoline-2,4-diones 7, where $R_1$–$R_4$ may be hydroxy, amino, nitro, a variety of alkyls, esters, and amides. In all cases, the substituent on $N_1$ is hydrogen. None of the substituents $R_1$–$R_4$ are nitrogen containing heterocycles. No antibacterial activity is revealed.

5

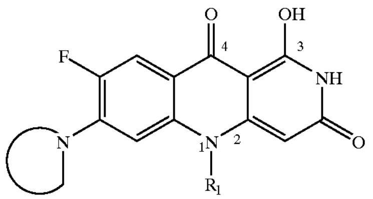

-continued

6

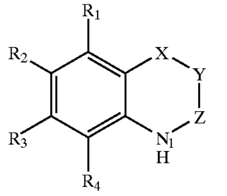

7

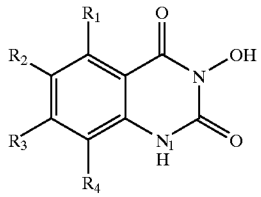

U.S. Pat. No. 5,155,110 (October 1992) reveals certain $N_1$-aryl-N-hydroxy-quinazoline-2,4-diones 8 as cyclooxygenase and lipoxygenase inhibitors. R may be halo, cyano, hydroxy, and substituted amino. Amino heterocycles are not included in R, and no antibacterial activity is described.

8

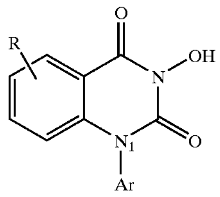

SUMMARY OF THE INVENTION

Described are compounds of Formula I which are new:

I

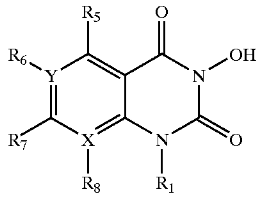

or a pharmaceutically acceptable salt thereof wherein:

$R_1$ is H, a straight or branched alkyl of 1 to 6 carbons, cycloalkyl of 3 to 6 carbons, a heterocycle of 4 to 6 atoms having 1 to 2 heteroatoms, or a phenyl group, each is optionally substituted by R, F, Cl, OR, or $N(R)_2$ wherein R is H, a straight or branched alkyl of 1 to 6 atoms having 0 to 1 degrees of unsaturation, a ring of 3 to 6 atoms having 0 to 2 heteroatoms, or a phenyl group, each may be substituted by F, Cl, CN, $NO_2$, OH, $NH_2$; also, two R's may form a 3- to 7-membered ring with the atom to which it is attached which ring may have 0 to 1 heteroatoms;

$R_5$, $R_6$, and $R_8$ are each independently H, F, Cl, Br, $NO_2$, CN, $CF_3$, $(C(R)_2)_nOR$, $(C(R)_2)_nCO_2R$, $(C(R)_2)_nCON(R)_2$, $(C(R)_2)_nN(R)_2$, $(C(R)_2)_nNRCOR$, a straight or branched alkyl of 1 to 4 carbons containing 0 to 1 degrees of unsaturation, a cycloalkyl of 3 to 6 carbons, each optionally substituted by F, Cl, OR, or $N(R)_2$ wherein R is as defined above;

$R_1$ and $R_8$ may form a ring of 6 to 7 atoms having 1 to 2 heteroatoms which ring may be substituted by one or more R's wherein R is as defined above;

$R_7$ is selected from $R_5$, $R_6$, $R_8$, a carbocycle of 3 to 7 carbons, a phenyl, or a heterocyclic ring of 4 to 7 atoms, a fused heterocyclic ring of 8 to 10 atoms, a bicyclic heterocycle of 6 to 9 atoms, or a spiro heterocycle of 7 to 12 atoms each having 1 to 4 heteroatoms, and each of which is optionally substituted by one or more of R', F, Cl, $(C(R)_2)_nN(R)_2$, $(C(R)_2)_nOR$, O, $(C(R)_2)_nCON(R)_2$, $(C(R)_2)_nCOR$, $(C(R)_2)_nNRCOR$, $(C(R)_2)_nCO_2R$, wherein R is defined above and R' is defined as R which is defined above; any of the adjacent groups $R_5$–$R_8$ may together form a 5- to 7-membered ring having 0 to 2 heteroatoms, which rings may be substituted by any of the groups described for $R_7$;

n is an integer of from 0 to 3; and

X and Y are each independently carbon or nitrogen with the understanding that if X or Y is nitrogen, no substituent $R_6$ or $R_8$ is attached.

The invention is also a pharmaceutical composition of the above compounds and methods of using the compounds as pharmaceuticals useful in the treatment of bacterial infection.

DETAILED DESCRIPTION

Preferred compounds of the invention are those of Formula I in which:

$R_1$ is methyl, ethyl, cyclopropyl, t-butyl, 2-fluorocyclopropyl, 1- or 2-methylcyclopropyl, cyclopropylmethyl, $CHCH_2$, 4-fluorophenyl, or 2,4-difluorophenyl;

R is H, a straight or branched alkyl of 1 to 6 atoms, a ring of 3 to 6 atoms having 0 to 2 heteroatoms, or a phenyl group, each may be substituted by F, Cl, OH, $NH_2$; alternatively two R's may form a 3- to 7-membered ring having 0 to 2 additional heteroatoms;

$R_5$, $R_6$, and $R_8$ are each independently H, F, Cl, Br, $NO_2$, CN, $CF_3$, $CH{=}CH_2$, $(C(R)_2)_nOR$, $(C(R)_2)_nCO_2R$, $(C(R)_2)_nCON(R)_2$, $(C(R)_2)_nN(R)_2$, $(C(R)_2)_nNRCOR$, a straight or branched alkyl of 1 to 4 carbons, a cycloalkyl of 3 to 6 carbons wherein the alkyl or cycloalkyl is optionally substituted by F, Cl, OR, or $N(R)_2$;

$R_7$ is selected from $R_5$, $R_6$, $R_8$, a heterocyclic ring of 4 to 7 atoms, a fused heterocyclic ring of 8 to 10 atoms or a bicyclic heterocycle of 6 to 9 atoms, each having 1 to 4 heteroatoms, and each of which may be substituted by one or more of R', F, Cl, $(C(R)_2)_nNR_2$, $(C(R)_2)_nOR$, O, $(C(R)_2)_nCONR_2$, $(C(R)_2)_nCOR$, $(C(R)_2)_nNRCOR$, $(C(R)_2)_nCO_2R$, wherein R' is H, a straight or branched alkyl of 1 to 6 atoms having 0 to 1 degrees of unsaturation, a ring of 3 to 6 atoms having 0 to 2 heteroatoms, or a phenyl group, each may be substituted by F, Cl, CN, $NO_2$, OH, $NH_2$; also, two R''s may form a 3- to 7-membered ring with the atom to which it is attached which ring may have 0 to 1 heteroatoms;

n is an integer from 0 to 3; and

X and Y are each independently carbon or nitrogen.

Other preferred compounds of the invention are those of Formula I wherein any of the adjacent groups $R_5$–$R_8$ may together form a 5- to 7-membered ring having 0 to 2 heteroatoms and such rings may be substituted by any of the groups described for $R_7$;

n is 0 to 3;

R is H, a straight or branched alkyl of 1 to 4 carbons, a ring of 3 to 6 atoms having 0 to 2 heteroatoms or a phenyl, each may be optionally substituted by F, Cl, OH, CN, $NO_2$, or $NH_2$; and X and Y are independently carbon or nitrogen.

More preferred compounds of the invention are those of Formula I in which:

$R_1$ is ethyl, cyclopropyl, 2-fluorocyclopropyl, cyclopropylmethyl, t-butyl, or phenyl optionally substituted by F, Cl, OR, or $N(R)_2$;

R is H, methyl, ethyl, isopropyl, t-butyl, or phenyl;

R' is methyl, ethyl, phenyl, or a 2, 3, or 4-pyridyl each of which may be substituted with F, Cl, $CH_3$, $(CH_2)_nN(R)_2$, or OR;

$R_5$, $R_6$, and $R_8$ are each independently selected from H, F, Cl, Br, $CH_3$, $NH_2$, $CH{=}CH_2$, $NO_2$, and $OCH_3$;

$R_7$ is selected from $R_5$, $R_6$, $R_8$, a heterocyclic ring of 4 to 7 atoms, a fused heterocyclic ring of 8 to 10 atoms or a bicyclic heterocycle of 6 to 9 atoms, each having 1 to 4 heteroatoms, and each of which may be substituted by one or more of R', F, Cl, $(C(R)_2)_nNR_2$, $(C(R)_2)_nOR$, O, $(C(R)_2)_nCON(R)_2$, $(C(R)_2)_nCOR$, $(C(R)_2)_nNRCOR$, $(C(R)_2)_nCO_2R$, a straight or branched alkyl of 1 to 4 atoms, or a phenyl group which may also be substituted as described above;

n is an integer from 0 to 3; and

X is a carbon or nitrogen and Y is a carbon.

Still more preferred compounds of the invention are those of Formula I in which:

$R_1$ is ethyl, cyclopropyl, t-butyl, or phenyl, optionally substituted by F, Cl, OR, or $NR_2$;

$R_5$, $R_6$, and $R_8$ are each independently selected from H, F, Cl, Br, $CH_3$, $NH_2$, $NO_2$, and $OCH_3$;

$R_7$ is a 5- or 6-membered ring heterocycle, having 1 to 2 heteroatoms, optionally substituted by $(C(R)_2)_nN(R)_2$; a [4.3.0]-bridged heterocycle with 1 to 2 heteroatoms, optionally substituted by $(C(R)_2)_nN(R)_2$; a [3.1.0]-bridged heterocycle having 1 heteroatom, optionally substituted by $(C(R)_2)_nN(R)_2$; a bridged heterocycle of 7 to 9 atoms having 1 to 3 heteroatoms, or a spiro heterocycle of 7 to 12 atoms having 1 to 2 heteroatoms optionally substituted by $(C(R)_2)_nN(R)_2$, which heterocycles may also be substituted by R', F, Cl, or OH;

n is an integer from 0 to 3;

R is H, a straight or branched alkyl of 1 to 6 atoms, which may be substituted by F, Cl, OH, $NH_2$; alternatively two R's may form a 3- to 7-membered ring having 0 to 2 additional heteroatoms;

R' is a straight or branched alkyl of 1 to 4 carbons, a phenyl or a heterocycle of 5 or 6 atoms with 1 or 2 heteroatoms optionally substituted by F, Cl, OH, CN, $NO_2$, or $(CH_2)_nN(R)_2$; also, two R"s may form a cyclopropyl or a cyclobutyl ring; and X is carbon or nitrogen; and Y is carbon.

Still other more preferred compounds of Formula I are those in which $R_1$ is ethyl, cyclopropyl, cyclopropylmethyl, t-butyl, or phenyl, optionally substituted by F, Cl, OR, or $N(R)_2$.

Other still more preferred compounds are those of Formula I, wherein adjacent groups $R_5$–$R_8$ form a 5- or 6-membered ring having 1 to 2 heteroatoms and which may be substituted by any of the groups described above for $R_7$;

n is 0 to 1;

R is H, a straight or branched alkyl of 1 to 4 carbons, a ring of 3 to 6 atoms having 0 to 2 heteroatoms or a phenyl, optionally substituted by F, Cl, OH, CN, $NO_2$, or $NH_2$; and X and Y are independently carbon or nitrogen with the understanding that if X or Y is nitrogen, no substituent $R_6$ or $R_8$ is attached.

Other still more preferred compounds are those of Formula I wherein $R_1$ and $R_8$ form a 6-membered ring having 1 to 2 heteroatoms and where the ring is optionally substituted with H, $CH_3$, $CH_2CH_3$, F, or $OCH_3$;

R is H, a straight or branched alkyl of 1 to 3 atoms or phenyl optionally substituted by F, Cl, OH, or $NH_2$;

$R_5$ and $R_6$ are each independently H, F, Cl, Br, $NO_2$, $NH_2$, $CH_3$, $CHCH_2$ or $R_5$ and $R_6$ may form a ring of 5 to 7 atoms having 0 to 2 heteroatoms;

$R_7$ is selected from $R_5$, $R_6$ and $R_8$, cyclopropane, cyclobutane, cyclopentane, cyclohexane, a heterocyclic ring of 4 to 7 atoms, a fused heterocyclic ring of 8 to 10 atoms, or a bicyclic heterocycle of 6 to 9 atoms, each having 1 to 4 heteroatoms, and each of the above may be optionally substituted by one or more of R', F, Cl, $(CR_2)_nN(R)_2$, $(CR_2)_nOR$, or O, wherein R' is methyl, ethyl, isopropyl, phenyl, a heterocycle of 5 to 6 atoms having 1 to 2 heteroatoms, each of which may be substituted by F, Cl, $CH_3$, $(CH_2)_nN(R)_2$, or OR;

n is an integer of 0 to 3; and

Y may be carbon or nitrogen.

Still other more preferred compounds in the invention are those of Formula I where $R_1$ is ethyl, cyclopropyl, or fluorocyclopropyl;

R is H, ethyl, propyl, isopropyl or phenyl, each optionally substituted with F, Cl, OH, or $NH_2$;

$R_5$, $R_6$, and $R_8$ are each independently H, F, Cl, Br, $NO_2$, methyl, ethyl, ethylene, or any $R_5$–$R_8$ may form a ring of 5 to 6 atoms having 0 to 2 heteroatoms;

$R_7$ is a carbocycle of 3 to 6 atoms, a heterocycle of 5 to 6 atoms having 1 to 2 heteroatoms, a fused heterocycle having 9 atoms and 2 heteroatoms, a bicyclic heterocycle of 6 to 8 atoms having 1 to 2 heteroatoms, each of which may be substituted by one or more of R', F, $N(R)_2$, $CH_2N(R)_2$, $CH_2CH_2N(R)_2$, $(CH_3)N(R)_2$, $C(CH_3)_2N(R)_2$, $CH_2OH$, $CH_2CH_2OH$, or OH, wherein R' is methyl, ethyl, or phenyl optionally substituted by any of the above;

Y is carbon; and

X is carbon or nitrogen.

Most preferred compounds in the invention are those of Formula I where $R_1$ is ethyl, cyclopropyl, cyclopropylmethyl, t-butyl, or phenyl, optionally substituted by F, OH, or $N(R)_2$;

R is H, methyl, or ethyl;

R' is methyl, ethyl, isopropyl, phenyl, a heterocycle of 5 to 6 atoms containing 1 to 2 heteroatoms, each of which may be substituted by F, Cl, $CH_3$, $(CH_2)_nN(R)_2$, or OR;

$R_5$ is H, F, or $NH_2$;

$R_6$ is H, F, Cl, Br, $OCH_3$, $CH{=}CH_2$, or $NO_2$;

$R_8$ is H, F, Cl, Br, $CH_3$, or $OCH_3$;

$R_7$ is a 5- or 6-membered ring heterocycle, having 1 to 2 heteroatoms, optionally substituted by $(C(R)_2)_nN(R)_2$; a [4.3.0]-bridged heterocycle, with 1 to 2 heteroatoms, which may be optionally substituted by $(C(R)_2)_nN(R)_2$; a [3.1.0]-bridged heterocycle, having 1 heteroatom, which may be optionally substituted by $(C(R)_2)_nN(R)_2$; a bridged heterocycle of 7 to 9 atoms having 1 to 3 heteroatoms, which may be optionally substituted by $(C(R)_2)_nNR_2$, which heterocycles may also be substituted by R', F, Cl, or OH;

n is 0 to 1;

Y is carbon; and

X is carbon or nitrogen.

Still most preferred are compounds:

1-Ethyl-6-fluoro-3-hydroxy-7-pyrrolidin-1-yl-1H-quinazoline-2,4-dione;

1-Ethyl-6-fluoro-3-hydroxy-7-(4-methyl-piperazin-1-yl)-1H-quinazoline-2,4-dione;

1-Ethyl-6-fluoro-3-hydroxy-7-morpholin-4-yl-1H-quinazoline-2,4-dione;

1-Ethyl-6-fluoro-3-hydroxy-7-piperidin-1-yl-1H-quinazoline-2,4-dione;

1-(1-Ethyl-6-fluoro-3-hydroxy-2,4-dioxo-1,2,3,4-tetrahydro-quinazolin-7-yl)-pyrrolidin-3-ylmethyl]-carbamic acid, tert-butyl ester;

7-(3-Aminomethyl-pyrrolidin-1-yl)-1-ethyl-6-fluoro-3-hydroxy-1H-quinazoline-2,4-dione, hydrochloride;

1-Ethyl-6-fluoro-3-hydroxy-7-piperazin-1-yl-1H-quinazoline-2,4-dione;

1-(1-Ethyl-6-fluoro-3-hydroxy-2,4-dioxo-1,2,3,4-tetrahydro-quinazolin-7-yl)-pyrrolidin-3-methyl-3-ylmethyl]-carbamic acid, tert-butyl ester;

7-(3-Aminomethyl-3-methyl-pyrrolidin-1-yl)-1-ethyl-6-fluoro-3-hydroxy-1H-quinazoline-2,4-dione, hydrochloride;

6-Fluoro-3-hydroxy-7-pyrrolidin-1-yl-1H-quinazoline-2,4-dione;

1-(6-Fluoro-3-hydroxy-1H-2,4-dioxo-1,2,3,4-tetrahydro-quinazolin-7-yl)-pyrrolidin-3-yl]-carbamic acid, tert-butyl ester;

6-Fluoro-3-hydroxy-1-methyl-7-pyrrolidin-1-yl-1H-quinazoline-2,4-dione;

7-(3-Amino-pyrrolidin-1-yl)-6-fluoro-3-hydroxy-1-methyl-1H-quinazoline-2,4-dione, hydrochloride;

1-(4-Hydroxyphenyl)-6-fluoro-3-hydroxy-7-pyrrolidin-1-yl-1H-quinazoline-2,4-dione;

1-(4-Fluorophenyl)-6-fluoro-3-hydroxy-7-pyrrolidin-1-yl-1H-quinazoline-2,4-dione;

1-(4-Fluorophenyl)-6-fluoro-3-hydroxy-7-(4-methylpiperazin-1-yl)-1H-quinazoline-2,4-dione, trifluoroacetate;

1-(4-Fluorophenyl)-6-fluoro-3-hydroxy-7-(3-aminopyrrolidin-1-yl)-1H-quinazoline-2,4-dione, hydrochloride;

1-(4-Methoxyphenyl)-6-fluoro-3-hydroxy-7-pyrrolidin-1-yl-1H-quinazoline-2,4-dione;

1-(4-Methoxyphenyl)-6-fluoro-3-hydroxy-7-(4-methylpiperazin-1-yl)-1H-quinazoline-2,4-dione;

1-(4-Methoxyphenyl)-6-fluoro-3-hydroxy-7-(3-aminopyrrolidin-1-yl)-1H-quinazoline-2,4-dione, hydrochloride;

1-(3-Chloro-4-fluorophenyl)-6-fluoro-3-hydroxy-7-(4-methylpiperazin-1-yl)-1H-quinazoline-2,4-dione;

1-(3-Chloro-4-fluorophenyl)-6-fluoro-3-hydroxy-7-(3-aminopyrrolidin-1-yl)-1H-quinazoline-2,4-dione, trifluoroacetate;

1-(3-Methoxyphenyl)-6-fluoro-3-hydroxy-7-pyrrolidin-1-yl-1H-quinazoline-2,4-dione;

1-(3-Methoxyphenyl)-6-fluoro-3-hydroxy-7-(4-methylpiperazin-1-yl)-1H-quinazoline-2,4-dione;

1-(3-Methoxyphenyl)-6-fluoro-3-hydroxy-7-(3-aminopyrrolidin-1-yl)-1H-quinazoline-2,4-dione, hydrochloride 1-(2-Fluorophenyl)-6-fluoro-3-hydroxy-7-pyrrolidin-1-yl-1H-quinazoline-2,4-dione;

1-(2-Fluorophenyl)-6-fluoro-3-hydroxy-7-(4-methylpiperazin-1-yl)-1H-quinazoline-2,4-dione;

1-(3-Fluorophenyl)-6-fluoro-3-hydroxy-7-pyrrolidin-1-yl-1H-quinazoline-2,4-dione;

1-(3-Fluorophenyl)-6-fluoro-3-hydroxy-7-(4-methylpiperazin-1-yl)-1H-quinazoline-2,4-dione;

1-(3-Fluorophenyl)-6-fluoro-3-hydroxy-7-(3-aminopyrrolidin-1-yl)-1H-quinazoline-2,4-dione, trifluoroacetate;

1-(2,4,5-Trifluorophenyl)-6-fluoro-3-hydroxy-7-(3-aminopyrrolidin-1-yl)-1H-quinazoline-2,4-dione, trifluoroacetate;

1-Cyclopropyl-6-fluoro-3-hydroxy-7-pyrrolidin-1-yl-1H-pyrido[2,3-d]pyrimidine-2,4-dione;

1-Cyclopropyl-6-fluoro-3-hydroxy-7-(4-methylpiperazin-1-yl)-1H-pyrido[2,3-d]pyrimidine-2,4-dione, hydrochloride;

1-Ethyl-6-fluoro-3-hydroxy-7-pyrrolidin-1-yl-1H-pyrido[2,3-d]pyrimidine-2,4-dione;

1-Ethyl-6-fluoro-3-hydroxy-7-(4-methylpiperazin-1-yl)-1H-pyrido[2,3-d]pyrimidine-2,4-dione;

7-(3-Aminopyrrolidin-1-yl)-1-ethyl-6-fluoro-3-hydroxy-1H-pyrido[2,3-d]pyrimidine-2,4-dione, trifluoroacetate;

1-Benzyl-6-fluoro-3-hydroxy-7-pyrrolidin-1-yl-1H-pyrido[2,3-d]pyrimidine-2,4-dione;

1-Cyclopropyl-6-fluoro-3-hydroxy-7-(pyrrolidin-1-yl)-1H-quinazoline-2,4-dione;

7-(3-Amino-pyrrolidin-1-yl)-1-cyclopropyl-6-fluoro-3-hydroxy-1H-quinazoline-2,4-dione;

7-(3-Aminomethyl-pyrrolidin-1-yl)-1-cyclopropyl-6-fluoro-3-hydroxy-1H-quinazoline-2,4-dione, trifluoroacetate;

7-(3-Amino-azetidin-1-yl)-1-cyclopropyl-6-fluoro-3-hydroxy-1H-quinazoline-2,4-dione, trifluoroacetate;

(1α,5α,6α)7-(6-Amino-3-aza-bicyclo[3.1.0]hex-3-yl)-1-cyclopropyl-6-fluoro-3-hydroxy-1H-quinazoline-2,4-dione, trifluoroacetate;

(4αS-cis)1-Cyclopropyl-6-fluoro-3-hydroxy-7-(octahydro-pyrrolo[3,4-b]pyridin-6-yl)-1H-quinazoline-2,4-dione, trifluoroacetate;

8-Fluoro-5-hydroxy-9-pyrrolidin-1-yl-2,3-dihydro-1-thia-3a,5-diaza-phenalene-4,6-dione;

9-(3-Amino-pyrrolidin-1-yl)-8-fluoro-5-hydroxy-2,3-dihydro-1-thia-3a,5-diaza-phenalene-4,6-dione, trifluoroacetate;

(1α,5α,6α)9-(6-Amino-3-aza-bicyclo[3.1.0]hex-3-yl)-8-fluoro-5-hydroxy-2,3-dihydro-1-thia-3a,5-diaza-phenalene-4,6-dione, trifluoroacetate;

1-Cyclopropyl-6,8-difluoro-3-hydroxy-7-pyrrolidin-1-yl-1H-quinazoline-2,4-dione;

1-Ethyl-5,6,8-trifluoro-3-hydroxy-7-pyrrolidin-1-yl-1H-quinazoline-2,4-dione;

1-Benzyl-6-fluoro-3-hydroxy-7-pyrrolidin-1-yl-1H-quinazoline-2,4-dione;

1-Benzyl-6-fluoro-3-hydroxy-7-(3-amino-pyrrolidin-1-yl)-1H-quinazoline-2,4-dione;

1-(2-Fluoroethyl)-6-fluoro-3-hydroxy-7-pyrrolidin-1-yl-1H-quinazoline-2,4-dione;

1-(2-Fluoroethyl)-6-fluoro-3-hydroxy-2,4-dioxo-1,2,3,4-tetrahydro-quinazolin-7-yl)-pyrrolidin-3-yl]-carbamic acid tert-butyl ester;

1-(2-Fluoroethyl)-6-fluoro-3-hydroxy-7-(ethyl-pyrrolidin-3-ylmethyl-amine-1-yl)-1H-quinazoline-2,4-dione;

1-(2,4-Difluorophenyl)-6-fluoro-3-hydroxy-7-pyrrolidin-1-yl-1H-quinazoline-2,4-dione;

1-(2,4-Difluorophenyl)-6-fluoro-3-hydroxy-7-(3-amino-pyrrolidin-1-yl)-1H-quinazoline-2,4-dione, hydrochloride;

6-Fluoro-1-(4-fluorophenyl)-3-hydroxy-7-pyrrolidin-1-yl-1H-pyrido[2,3-d]pyrimidine-2,4-dione;

1-Butyl-6-fluoro-3-hydroxy-7-pyrrolidin-1-yl-1H-pyrido[2,3-d]pyrimidine-2,4-dione;

6-Fluoro-3-hydroxy-7-pyrrolidin-1-yl-1-(4-trifluoromethylphenyl)-1H-pyrido[2,3-d]pyrimidine-2,4-dione;

1-(2,4-Difluorophenyl)-6-fluoro-3-hydroxy-7-pyrrolidin-1-yl-1H-pyrido[2,3-d]pyrimidine-2,4-dione;

6-Fluoro-3-hydroxy-1-(4-methylphenyl)-7-pyrrolidin-1-yl-1H-pyrido[2,3-d]pyrimidine-2,4-dione;

6-Fluoro-3-hydroxy-7-pyrrolidin-1-yl-1-(3-trifluoromethylphenyl)-1H-pyrido[2,3-d]pyrimidine-2,4-dione;

1-(2-Fluorophenyl)-6-fluoro-3-hydroxy-7-pyrrolidin-1-yl-1H-pyrido[2,3-d]pyrimidine-2,4-dione;

6-Fluoro-3-hydroxy-1-(4-methoxyphenyl)-7-pyrrolidin-1-yl-1H-pyrido[2,3-d]pyrimidine-2,4-dione;

1-Cyclopropylmethyl-6-fluoro-3-hydroxy-7-pyrrolidin-1-yl-1H-quinazoline-2,4-dione;

1-(4-Fluorophenyl)-6-fluoro-3-hydroxy-7-(3-amino-pyrrolidin-1-yl-1H-pyrido[2,3-d]pyrimidine-2,4-dione, hydrochloride;

(1α,5α,6α)[3-(1-(4-Fluorophenyl)-6-fluoro-3-hydroxy-2,4-dioxo-1,2,3,4-tetrahydropyrido[2,3-d]pyrimidine-7-yl)-3-aza-bicyclo[3.1.0]hex-6-yl]-carbamic acid tert-butyl ester;

7-(6-Amino-3-aza-bicyclo[3.1.0]hex-3-yl)-1-cyclopropyl-6,8-difluoro-3-hydroxy-1H-quinazoline-2,4-dione;

7-(3-Amino-pyrrolidin-1-yl)-1-cyclopropyl-6,8-difluoro-3-hydroxy-1H-quinazoline-2,4-dione;

9-(3-Amino-pyrrolidin-1-yl)-8-fluoro-5-hydroxy-3-methyl-2,3-dihydro-1-oxa-3a,5-diaza-phenalene-4,6-dione;

9-(3-Amino-pyrrolidin-1-yl)-3-ethyl-8-fluoro-5-hydroxy-2,3-dihydro-1-oxa-3a,5-diaza-phenalene-4,6-dione;

9-(3-Amino-pyrrolidin-1-yl)-8-fluoro-5-hydroxy-2,3-dihydro-1-oxa-3a,5-diaza-phenalene-4,6-dione;

9-(3-Amino-pyrrolidin-1-yl)-8-fluoro-5-hydroxy-3-methyl-2,3-dihydro-1-oxa-3a,5-diaza-phenalene-4,6-dione;

9-(3-Amino-pyrrolidin-1-yl)-8-fluoro-5-hydroxy-3-methyl-2,3-dihydro-1-oxa-3a,5-diaza-phenalene-4,6-dione;

9-(3-Amino-pyrrolidin-1-yl)-8-fluoro-5-hydroxy-3-methyl-2,3-dihydro-1-oxa-3a,5-diaza-phenalene-4,6-dione;

9-(3-Amino-pyrrolidin-1-yl)-8-fluoro-5-hydroxy-2-methyl-2,3-dihydro-1-oxa-3a,5-diaza-phenalene-4,6-dione;

9-(3-Amino-pyrrolidin-1-yl)-8-fluoro-5-hydroxy-3-methyl-2,3-dihydro-1-thia-3a,5-diaza-phenalene-4,6-dione;

9-(3-Amino-pyrrolidin-1-yl)-8-fluoro-5-hydroxy-2-methyl-2,3-dihydro-1-thia-3a,5-diaza-phenalene-4,6-dione;

5-Amino-7-(6-amino-3-aza-bicyclo[3.1.0]hex-3-yl)-1-cyclopropyl-6,8-difluoro-3-hydroxy-1H-quinazoline-2,4-dione;

5-Amino-7-(3-amino-pyrrolidin-1-yl)-1-cyclopropyl-6,8-difluoro-3-hydroxy-1H-quinazoline-2,4-dione;

7-(6-Amino-3-aza-bicyclo[3.1.0]hex-3-yl)-6,8-difluoro-3-hydroxy-1-(2-methyl-butyl)-1H-quinazoline-2,4-dione;

7-(3-Aminomethyl-3-methyl-pyrrolidin-1-yl)-6-fluoro-3-hydroxy-1-(2-methyl-butyl)-1H-quinazoline-2,4-dione;

7-(6-Amino-3-aza-bicyclo[3.1.0]hex-3-yl)-1-cyclopropyl-6-fluoro-3-hydroxy-1H-pyrido[2,3-d]pyrimidine-2,4-dione;

7-(3-Amino-pyrrolidin-1-yl)-8-chloro-1-cyclopropyl-6-fluoro-3-hydroxy-1H-quinazoline-2,4-dione;

7-(3-Amino-pyrrolidin-1-yl)-1-cyclopropyl-6-fluoro-3-hydroxy-8-methoxy-1H-quinazoline-2,4-dione; and 7-(3-Amino-pyrrolidin-1-yl)-1-cyclopropyl-6-fluoro-3-hydroxy-8-methylsulfanyl-1H-quinazoline-2,4-dione.

Here, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, and dodecyl. The alkyl groups may contain one or more sites of unsaturation such as double or triple carbon-carbon bonds. The alkyl group is unsubstituted or substituted by from 1 to 3 substituents selected from F, Cl, Br, OH, $NH_2$, CN, $NO_2$, $OCH_3$, $OCH_2CH_2OH$, $NHCH_3$, or $N(CH_3)_2$.

The term "cycloalkyl" means a hydrocarbon ring which contains from 3 to 12 carbon atoms unless otherwise specified, for example, cyclopropyl, cyclobutyl, cyclopentyl, cyclohexyl, and adamantyl. Where possible, the cycloalkyl group may contain double bonds. The cycloalkyl ring may be unsubstituted or substituted by from 1 to 3 substituents selected from alkyl, alkoxy, thioalkoxy all as defined herein, hydroxy, thiol, nitro, halogen, amino, formyl, carboxyl, nitrile, —NH—CO—R, —CO—NHR—, —$CO_2$R, —COR, aryl, or heteroaryl wherein alkyl (R), aryl, and heteroaryl are defined as herein.

The term "heterocycle" means a heterocyclic radical which is 2- or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isaxazolyl, 3- or 5- 1,2,4-triazolyl, 4- or 5- 1,2,3-triazolyl, tetrazolyl, 2-, 3-, or 4-pyridinyl, 3-, 4-, or 5-pyridazinyl, 2-pyrazinyl, 2-, 4-, or 5-pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1- or 2-piperazinyl, 2-, 3-, or 4-morpholinyl, 2-, 3-, or 4-thiomorpholinyl, 1-, 2-, or 3-pyrrolidinyl, 2- or 3-tetrahydrofuranyl, 2-, 3-, or 4-tetrahydropyranyl, 2-3-, or 4-piperidinyl, 1-, 2-, 4-, 5-, or 6-tetrahydropyrimidinyl, 2-dioxolinyl, 2-, 4-, or 5-imidazolidinyl, 1-, 2-, 3-, 4-, 5-, 6-, or 7-indolinyl, unsubstituted or substituted by 1 to 2 substituents selected from alkyl as defined above. For heterocycles containing sulfur, the oxidized sulfur heterocycles containing SO or $SO_2$ groups are also included.

The acids, alcohols, and amines which appear in the invention may have to be protected before or during preparation of the final product.

For purposes of the syntheses of the compounds of the present invention, reactive functional groups present in starting materials, reaction intermediates, or reaction products may be protected during chemical reactions using protecting groups which render the reactive functional groups substantially inert to the reaction conditions (see for example, *Protective Groups in Organic Synthesis*, 2 ed., T. W. Green and P. G. Wuts, John Wiley & Sons, New York, N.Y. 1991). Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl, p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc.

Fused heterocyclic rings of from 8 to 10 atoms include but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

Heterocycles include but are not limited to

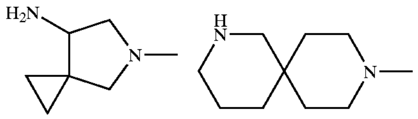
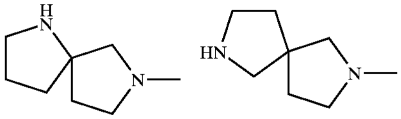
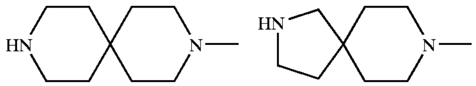
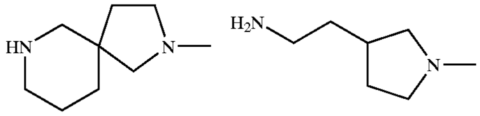
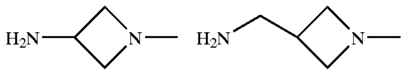
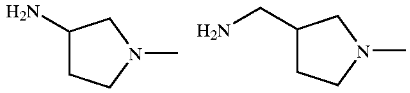
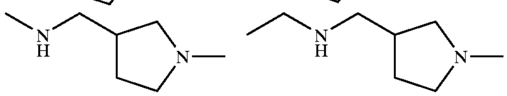
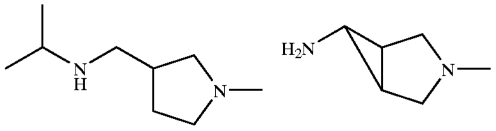

-continued

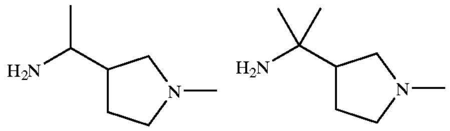
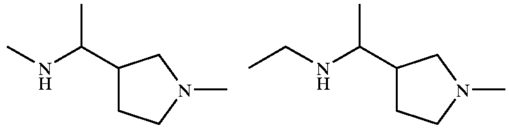
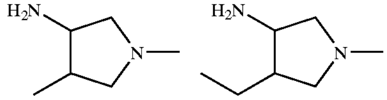
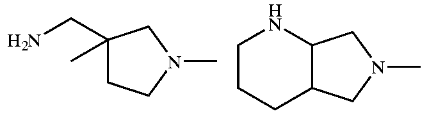
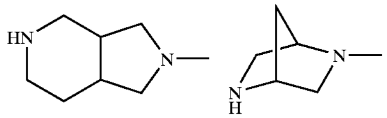
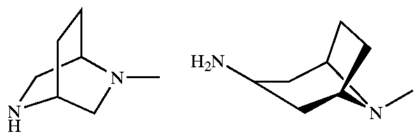
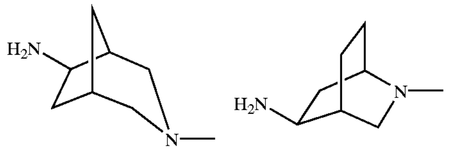
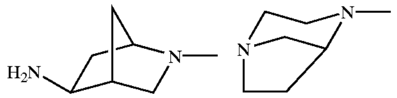
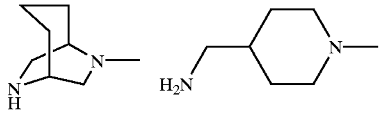
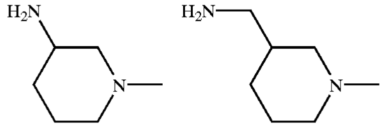
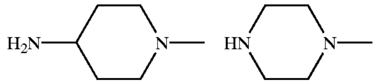
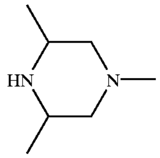
and
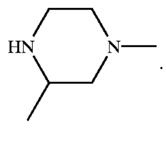
.

In all cases, primary and secondary amines may be substituted by alkyl substituents.

Some of the compounds of Formula I are capable of further forming pharmaceutically acceptable acid-addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science*, 1977;66:1–19).

The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or, synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component as determined by a skilled physician. The composition can, if desired, also contain other compatible therapeutic agents.

In therapeutic use as agents for the treatment of infections caused by a bacteria, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is “Protecting Groups in Organic Synthesis” by Theodora Green. A number of general reactions such as oxidations and reductions etc. are not shown in detail but can be done by methods understood by one skilled in the art. General transformations are well-reviewed in “Comprehensive Organic Transformation” by Richard Larock, and the series “Compendium of Organic Synthetic Methods” published by Wiley-Interscience. In general, the starting materials were obtained from commercial sources unless otherwise indicated.

The compounds of the invention may be prepared according to the following methods in Schemes 1 to 4. All of the N-hydroxy-quinazoline-2,4-diones may be prepared from appropriately substituted benzoic acids. In Scheme 1, the anthranilic acid 1 is the key starting material. Such anthranilic acids are well-known in the art of organic synthesis and numerous methods for their preparation are published. The method employed is taken from Jacobs (*J. Het. Chem.*, 1970;7:1337). Accordingly, compound 1 may be reacted with phosgene ($COCl_2$) or carbonyldiimidazole (CDI) or other such equivalent in inert solvent such as THF, dioxane, benzene, toluene, or chlorocarbon solvents at temperatures of 0° C. to 80° C. The intermediate 2 may be isolated or used as is to react with an O-protected hydroxylamine. Generally, the protecting group is benzyl or p-methoxybenzyl, but any O-protecting group may be employed when desired. Such groups would include tetrahydropropanyl, t-butyl, 2-chloroethyl, allyl, alkyl, etc. Compound 3 is then again reacted with phosgene, triphosgene, CDI, or some equivalent to give the quinazoline-2,4-dione 4. The reaction is carried out in THF or dioxane at 25° C. to 150° C. At this point, the protecting group may be removed to give 5 which may represent a final product or may be further embellished. The protecting group may be removed by hydrogenation, acid or base treatment, metal catalysis, or a number of other methods described in protecting group art. When Pro is benzyl, the benzyl may be removed with $Pd/BaSO_4$ or Pd/C and hydrogen. The t-butyl group may be removed by alcoholic HCl, TFA, or TFA in dichloromethane. The allylic groups may be removed by $PhSiH_3$ and Pd catalyst. Solvents such as alcohol, THF, alcohol/THF, alcohol/THF/DMF, etc. are generally employed. The allyl, benzyl, or t-butyl groups may also be removed with boron tris(trifluoroacetate) in TFA (*Angew. Chem. Int. Ed.*, 1973;12:147). Reactions are run at room temperature to 50° C. and require 1 to 72 hours. Compound 5 may be further reacted, if $R_7$ is a leaving group, with various heterocyclic amines. The amines displace the leaving group, generally a F or a Cl to form the product 7. Other leaving groups would be Br, $OCH_3$, or nitro. Such chemistry is extremely well-known in the quinolone art and is summarized by Bouzard (Recent Progress in the Chemical Synthesis of Antibiotics, Springer Verlag 1990:249–283). Commonly, acetonitrile, DMF, or DMSO are used as solvents and generally reactions require a co-base such as triethylamine, DBU (1,8-diazobicyclo[5.4.0]undec-7-ene) or excess amine heterocycle. Reactions are carried out at 25° C. to 150° C. and require 0.5 to 48 hours. Alternatively, the heterocyclic amine may be directly reacted with 4 prior to removal of the protecting group. The conditions for the reaction are as described above. Carbocycles and aryls may also be introduced at $R_7$ if $R_7$ is a Br, I, or triflate using palladium catalyzed couplings of tin or boronate carbocycles and aryls. Compound 6 may then be deprotected to yield 7 using conditions described above for the conversion of 4 to 5.

Scheme 1

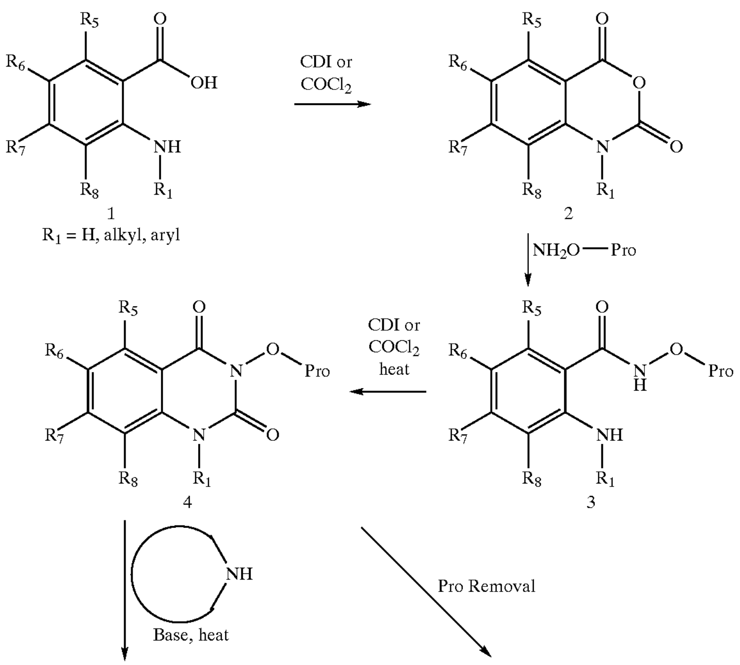

1

$R_1$ = H, alkyl, aryl

2

3

4

-continued

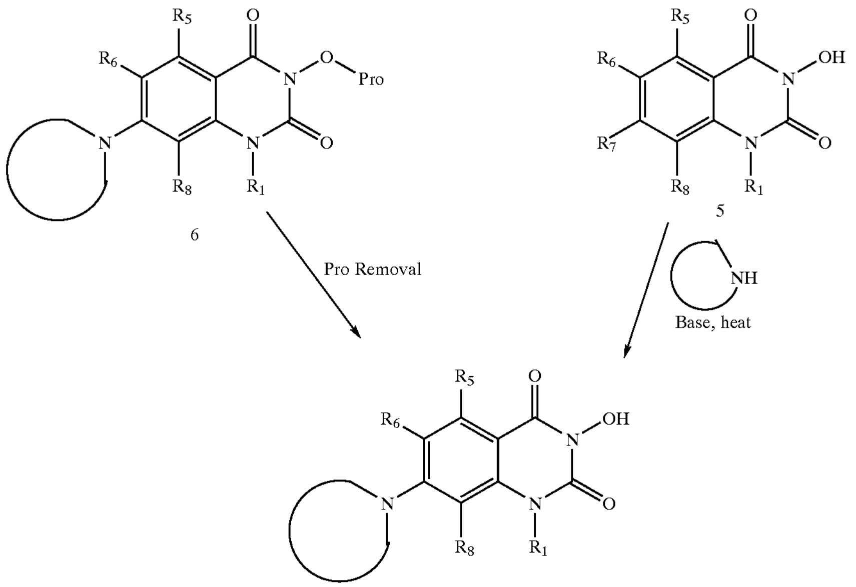

6 5 7

Compounds with structure 1 may be commercially available or synthesized by displacement of a leaving group ortho to the carboxy functional group in compound 10 (structure in Scheme 4) by $R_1NH_2$. When $R_1$ in $R_1NH_2$ is phenyl or substituted phenyl, then compounds of structure 1 may be prepared from the ortho fluorobenzoic acid 10 using lithium diisopropylamide and the appropriate $R_1NH_2$ at −78° C. to 25° C. in solvents such as ether or THF.

In Scheme 2, the method of Romine (*Synthesis*, 1994:846) is employed. This method begins with an anthranilic acid ester and requires the protected hydroxylamine to be activated for appendage to the nitrogen bearing $R_1$. This activation utilizes $(Cl_3CO)_2CO$ and the protected hydroxylamine in solvents such as benzene, toluene, THF, ether, methylene dichloride, and the like. Protecting groups are those as described above with benzyl being common. Reaction of 8 with the activated hydroxylamine yields 9 which may be converted to 4 by treatment with base in inert solvent. Typically, bases would include alkoxide in alcoholic solvents such as t-butoxide in t-butanol. Other hindered bases would also be appropriate such as LDA or Li-hexamethyl disilazide. In these latter cases, THF, ether, or DMSO would be suitable solvents. The reaction may be carried out at 10° C. to 80° C. for 0.5 to 24 hours. The compound 4 may be converted to 5 or 7 as shown in Scheme 1.

Scheme 2

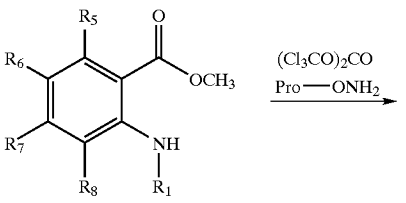

8
$R_1$ = H, alkyl, aryl

-continued

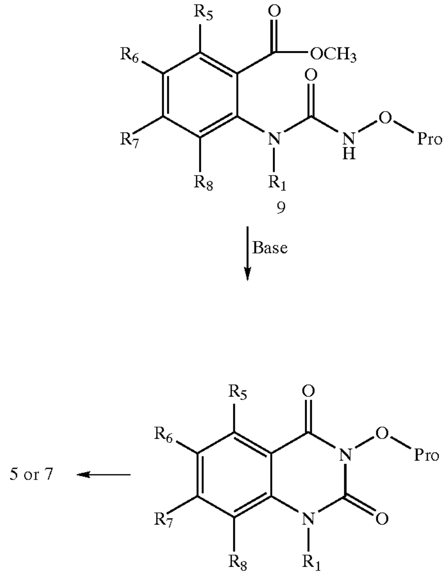

9 4

Scheme 3

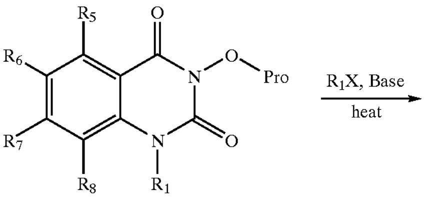

4
$R_1$ = H

-continued

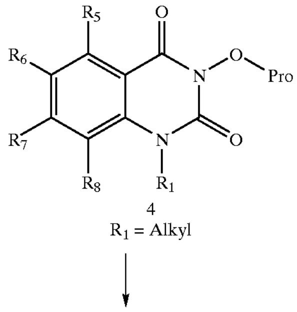

4

$R_1$ = Alkyl 5 or 7

When $R_1$ in 4 is hydrogen, an alkyl $R_1$ group may be introduced as shown in Scheme 3. Such a reaction is well-known in the quinolones art and is described by Bouzard, supra., 1990. Typically, such reactions are carried out in THF, ether, DMSO, alcohol, or DMF. Typical $R_1X$ would include ethyl iodide, ethyl bromide, diethyl sulfate, 2-bromoethanol, and the like. Typical bases would be sodium hydride, potassium carbonate, and the like. Once compound 4 is produced, with $R_1$ being alkyl, conversion to 5 or 7 may proceed according to Scheme 1.

In certain cases it may be desirable to add the $R_1N$ group late in the synthesis (Scheme 4). Such options are available when starting with a leaving group ortho to the carboxy group such as in the 2-fluoro benzoic acid 10. The acid 10 may be activated with oxalyl chloride, CDI, thionyl chloride as known in the art and the protected hydroxylamine added to give 11. Compound 11 is converted to 12 using an isocyanate ($OCNR_1$) and base, or with heat by a thermal reaction. The isocyanates are well-known starting materials. Typical bases would include NaH, KH, or $K_2CO_3$. Solvents would include toluene, xylenes, THF, ether, and the like at −10° C. to 150° C. The adduct 12 would then be cyclized according to the methods cited by Bouzard, supra., 1990. Such conditions would include the use of potassium t-butoxide, NaH, or the like in THF, DMF, DMSO, or other inert solvents at 15° C. to 100° C. Cyclization gives 4 which may be converted to 5 and 7 according to Scheme 1.

Displacement of leaving groups as shown in Scheme 1 is not limited to nitrogen heterocycles. Other nucleophiles (Nu) such as $CH_3O^-$, $R_2NH$, R—NH, and $RS^-$ will also displace a F, Cl, or $NO_2$ leaving group at $R_7$ as shown in Scheme 5.

Scheme 5

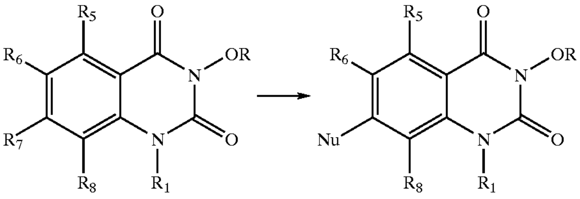

4 or 5

(R = H or Protecting Group)

13

(Same as 5 where $R_7$ is Nu)

Such reactions are carried out at 25° C. to reflux in solvents such as acetonitrile, THF, DMF, DMA, and the like. Likewise the reaction may be carried out in a pressure sealed vessel at elevated temperatures up to 150° C. The nucleophiles may be used in excess or, in the case of the amines, as solvents. When the leaving group is a triflate or higher halide, organo tin reagents or organoboronates may be used with palladium catalysts to deliver a carbon nucleophile. In this manner, all sorts of alkyl and aryl groups may be represented by Nu such as methyl, ethyl, vinyl, cyclopentyl, cyclopentenyl, and the like. The methodology follows that of Stille, et al. (*Agnew. Chem. Int. Ed. Eng.*, 1986;25:508) and is exemplified by Mitchell (*Synthesis*, 1992:803). This method is well-known in the art as is the preparation of triflates and the tin reagents.

All of the chemistry depicted and described in Schemes 1 to 5 would apply using the definitions of X and Y in Formula I. When either X or Y is nitrogen, the displacement chemistry would indeed be more facile than when X and Y are carbon.

In Scheme 6, synthetic methodologies to prepare compounds where two adjacent R groups form a ring are shown.

Scheme 4

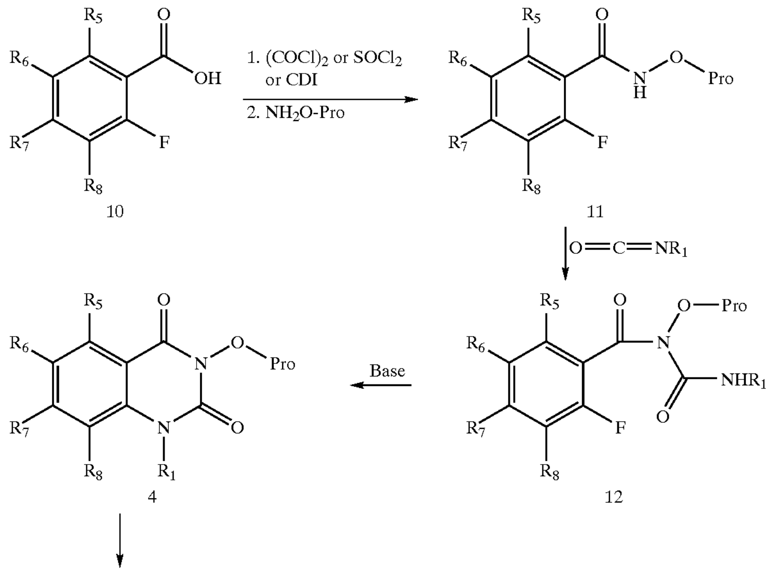

10

11

12

4

5 or 7

The alkylations such as in the preparation of 15 or 16 are carried out with inert bases such as $K_2CO_3$, $Cs_2CO_3$, $NaHCO_3$, and the like. Solvents are typically dioxane, DMF, DMA, DMSO, and the like. Temperatures are 25° C. to 125° C. The reaction of 17 to 18 is carried out at RT to 125° C. in solvents such as dioxane, DMF, and the like.

The reactions of 14 and 17 would also work for amine or thiol substituents and their relative position on the quinazoline ring system would not affect the chemistry. This is not so for the preparation of 20 since it involves a displacement of $R_7$. In this reaction, any primary amine may be employed in solvents such as dioxane, acetonitrile, DMSO, or DMF. The use of pressure-sealed vessels may be employed for volatile amines. The reaction may be carried out at 25° C. to 125° C.

Such systematic substitutions are demonstrated in Scheme 7. The pyridine ester 21 has leaving groups on both sides of the nitrogen. Such groups are generally chlorine, but fluorine, thiols, and thiolates are also good leaving groups in such compounds. These leaving groups may be sequentially displaced based on reactivity. In Scheme 7, where Y═N or CF, the 6-chloro of 21 is displaced preferentially using a nucleophilic amine such as diethylamine, pyrrolidine, methylpiperazine and the like to give 22. An inert base such as triethylamine, DBU, or the like is employed to take up the HCl that is generated in the reaction. The reaction is performed in acetonitrile, DMF, DMA or the like at 0° C. to 100° C. Compound 22 is then reacted with $R_1NH_2$ to displace the second leaving group. The reaction may be carried out with excess $R_1NH_2$ or with inert bases described above. Typical solvents are acetonitrile, THF, DMF, DMA or the like at temperatures from 0° C. to 100° C. The ester 23 is then hydrolyzed by any conditions known in the art, to the acid 24 which is then coupled by one of several amide forming reactions well-known in the art which activate the acid. Such methods would include acid chloride forming reagents, mixed anhydrides, carbonyldiimidazole (CDI), dicyclohexylcarbodiimide (DCC) or, activated esters such as Scheme 6

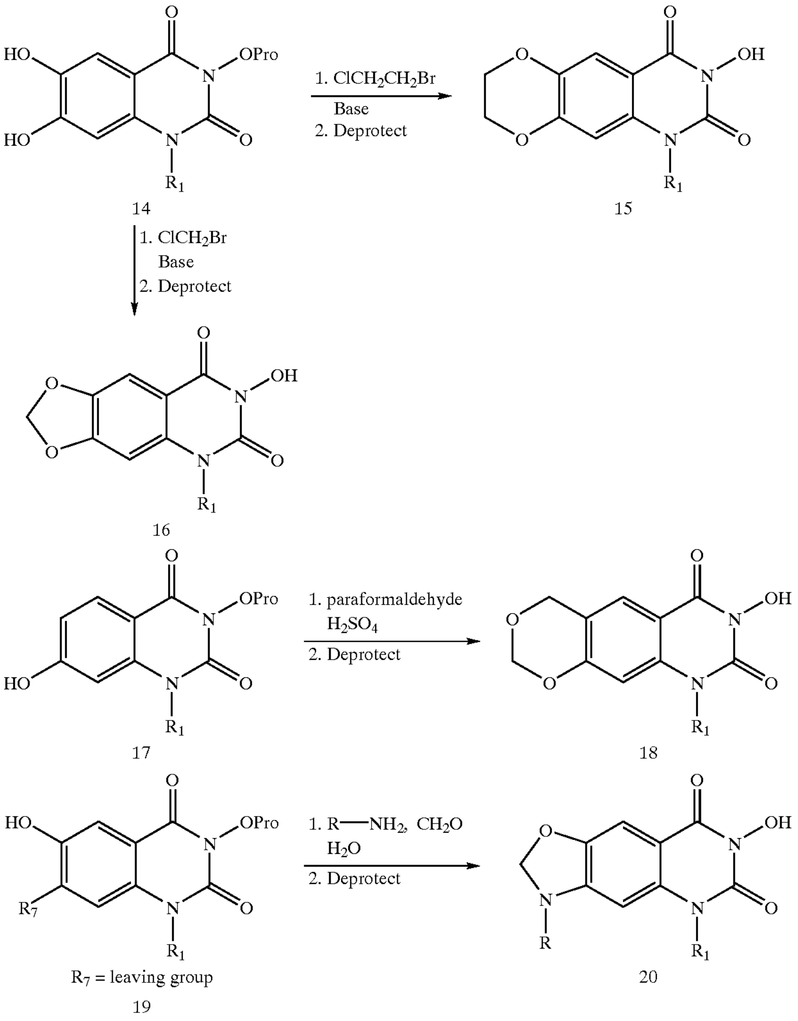

14, 15, 16, 17, 18, 19, 20

Compounds of the invention where X and/or Y of General Formula I are nitrogen may be prepared by the Schemes 1, 2, 3, and 5 or by routes which take advantage of the activation of leaving groups ortho and para to the nitrogen. Such routes will systematically introduce the groups labeled $R_7$ and $R_1$ in the General Formula I. This methodology also applies to cases in Formula I where X is CH or CF and Y is CF.

para nitrophenol, pentafluorophenol, or hydroxybenztriazole with DCC or 1-ethyl-3-(3'-dimethylaminopropyl) carbodimiide (EDCI). The NHO-benzyl amide 25 is then reacted with CDI, phosgene, or a phosgene equivalent to form the cyclized O-protected product 26. Typical solvents are ether, THF, DMF, and the like, and typical temperatures are 15° C. to 100° C. The reaction sequence taking 25 to 26 is identical to that described in Scheme 1 for the conversion of 3 to 4. Deprotection of the O-benzyl groups proceeds as described above to give the final products 27.

Scheme 7

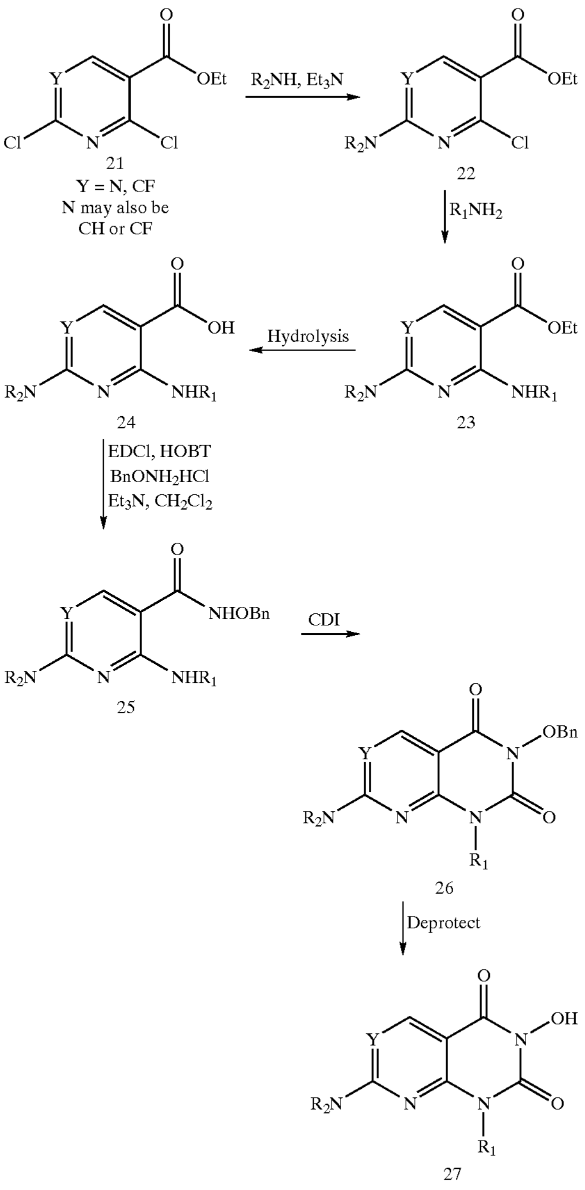

Another method for compounds of type I where X and/or Y are nitrogen in Formula I is patterned after Scheme 4. In Scheme 8, the NHO-benzyl amide 29 is prepared from 28 by one of the amide forming methods known in the art as described above. The NH of the NHO-benzyl of compound 29 is then deprotonated with an inert base such as sodium hydride, potassium hydride, and the like in solvents such as THF, DMF, or DMA at −78° C. to 50° C. The reaction mixture is then reacted with an isocyanate, RNCO, which captures the NO-benzyl anion and cyclizes in one pot. Compound 30 is then reacted, if desired, with various nucleophiles according to the conditions in Scheme 5 to give 26. Deprotection of 26 follows the methods described above to give 27.

Scheme 8

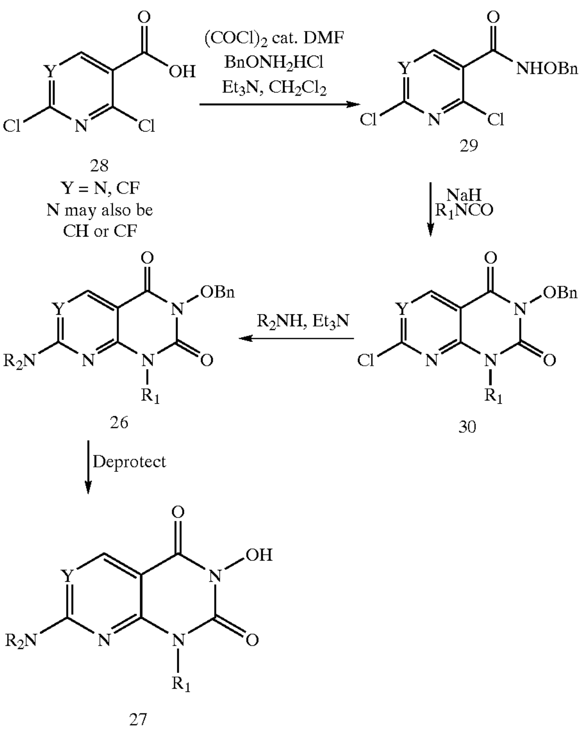

Tricyclic compounds (where $R_1$ and $R_8$ form a ring in Structure I) can be prepared according to Schemes 9 and 10. Schemes 9 and 10 differ in the introduction of the $R_1$ substitutions in 36 and 42 wherein $R_1$ and $R_1'$ are defined as for Structure I. In Scheme 9, the ortho fluoro nitro compound 31 serves as the starting material taking advantage of the activated fluorine toward displacement with a nucleophile: X. Other leaving groups such as chlorine, bromine, and sulfonyl may also be employed. The α-nucleophile substituted ester displaces the fluorine at temperatures 0° C. to 150° C. in solvents such as DMF, DMA, DMSO, acetonitrile and the like. The nitro group is then reduced using Raney Ni, $H_2$ over Pd/C, or with an active metal in acid such as iron or tin in HCl or acetic acid. The newly formed amine readily cyclizes on the ester to form 32. Other acid analogs may be employed such as esters, thio esters, amides and the like. Compound 32 is then reduced with hydride reducing agents such as $LiAlH_4$ and the like to produce compound 33. It is recognized that $R_1$ and $R_1'$ may form a chiral center giving R and S enantiomers. Such enantiomers may be separated, if desired, by chiral HPLC at any stage or by chemical resolution using mandelic acid, tartaric acid, or other chiral, optically pure acid bearing resolving agents. Chiral amides may also be employed such as the camphorsulfonamide, mandelamide, or the like. The quinazolinedione ring is prepared sequentially by first reacting 33 with chloral hydrate which forms the dione ring in 34. Compound 34 is ring opened using sodium hydroxide and hydrogen peroxide to give the benzoic acid which is cyclized with carbonyldiimidazole or a phosgene equivalent according to Scheme 1 to give the final product 36.

Scheme 9

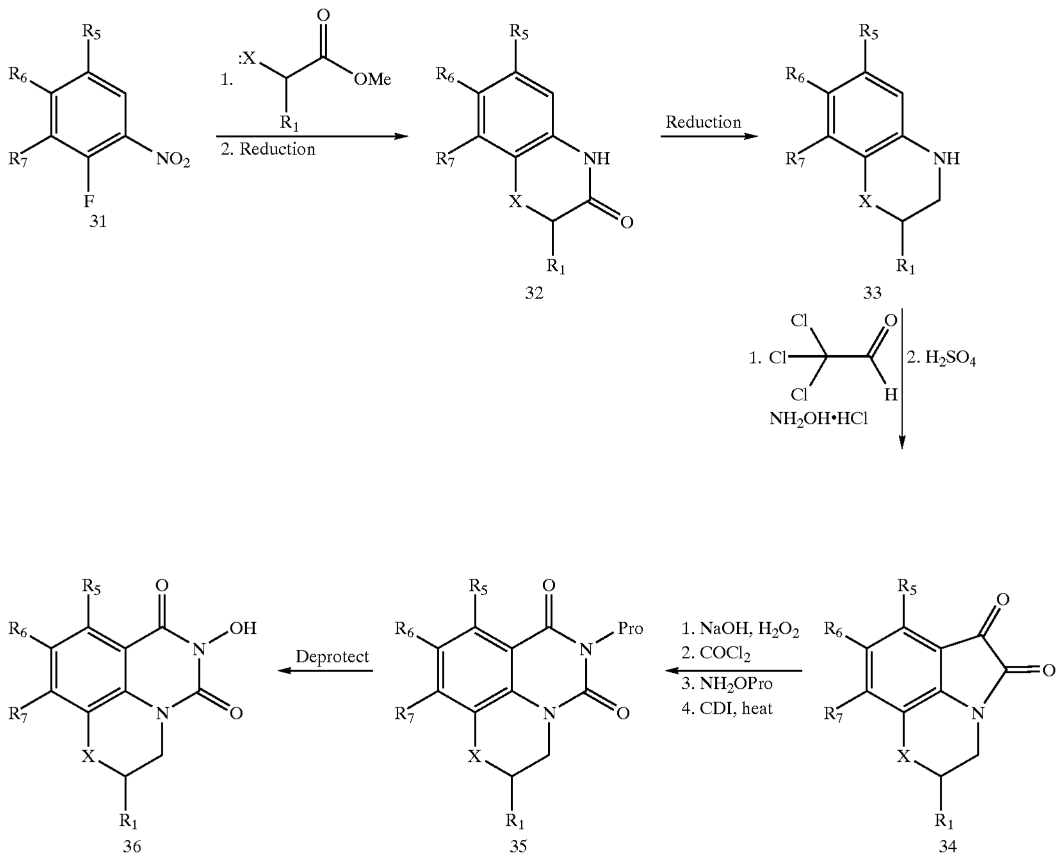

In a similar series of reactions, Scheme 10 utilizes the already reduced version of 31. Thus, the aniline 37 is reacted with an α-nucleophile substituted ketone. In this sequence the aniline forms a cyclic imine, which is reduced with $H_2$ on Pd/C or by chemical hydride reducing agents such as sodium borohydride or sodium cyanoborohydride to give 39. Such reductive aminations are well-known in the art and are typically performed in alcohol, water alcohol mixtures, or in water DMF mixtures at temperatures of 0° C. to 80° C. Again, the chiral centers may be resolved as discussed above. The remaining steps to produce 42 follow those of Scheme 9 for the conversion of 33 to 36. When $R_7$ is a leaving group, compounds 36 and 42 may be further reacted with nucleophiles to give compounds of Formula I as in the previous schemes.

Scheme 10

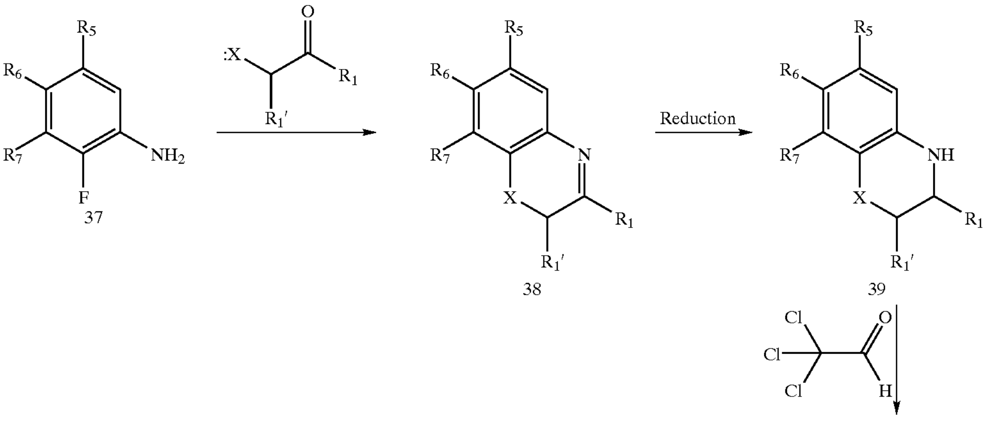

-continued

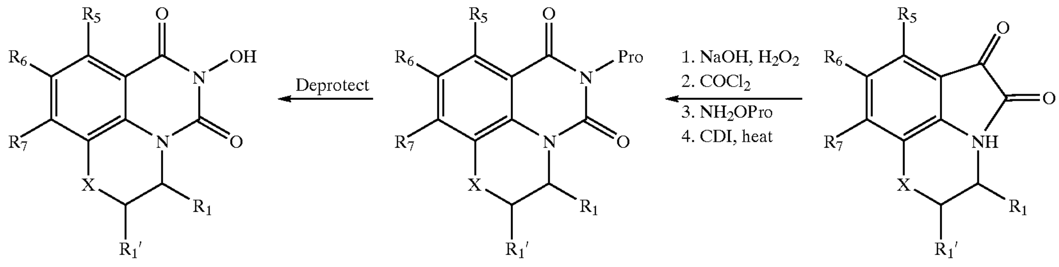

42 41 40

In Scheme 11, the target tricylic compounds as 42 are prepared in a slightly different manner. In this case, the nucleophile X is attached to the phenyl ring, and the leaving group L is attached alpha to the ketone. The nucleophile may be activated with bases such as sodium hydride or potassium hydride in solvents such as ether, THF, or DMF and the like at temperatures of 10° C. to 50° C. Alternate bases may be triethylamine or DBU in solvents such as ether, THF, acetonitrile, DMF or the like at temperatures of 25° C. to 100° C. Still other bases would include sodium or potassium carbonate in alcoholic solvents or DMF at temperatures of 25° C. to 100° C. Once compound 38 is obtained, the rest of Scheme 11 follows that of Scheme 10.

The kinds of nitrogen heterocycles envisioned for Scheme 1 are exemplified but not limited to those shown below:

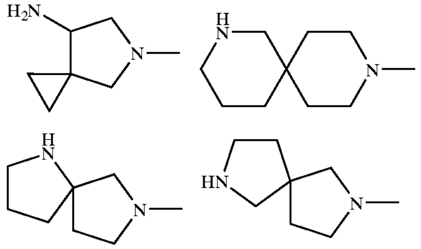

Scheme 11

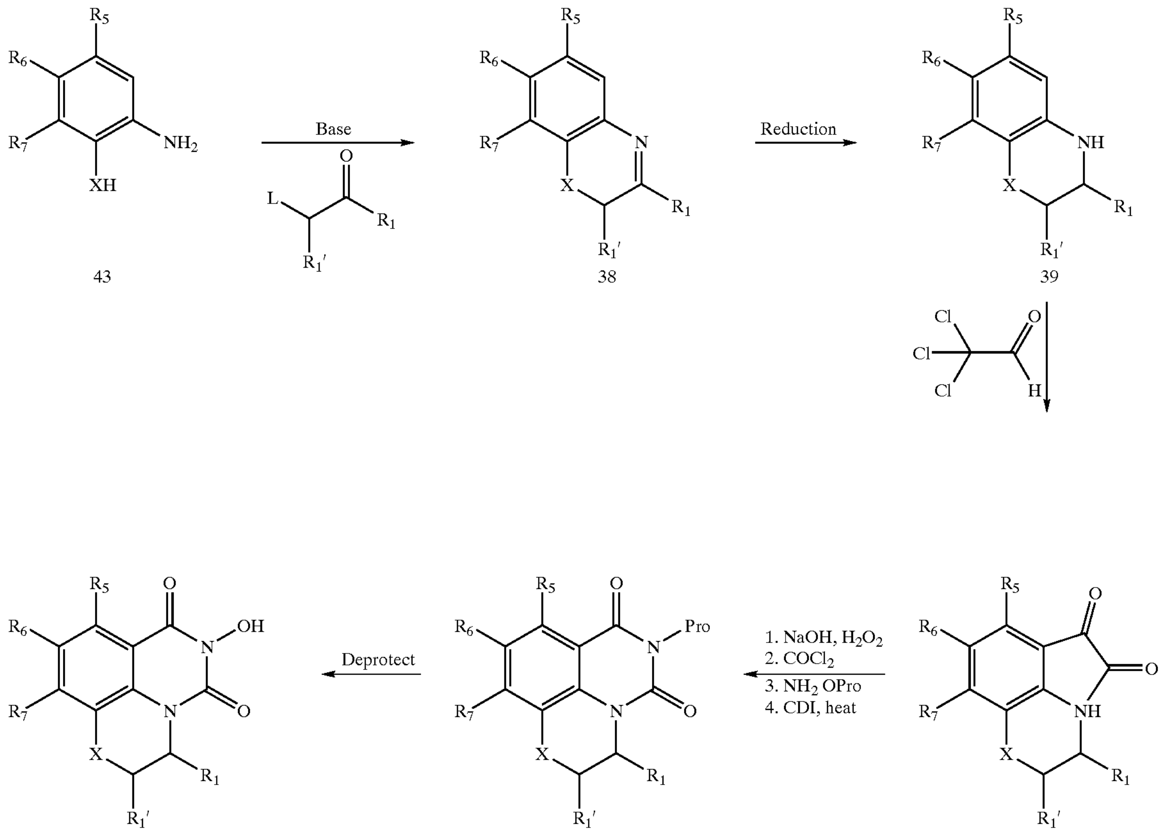

43 38 39

42 41 40

-continued

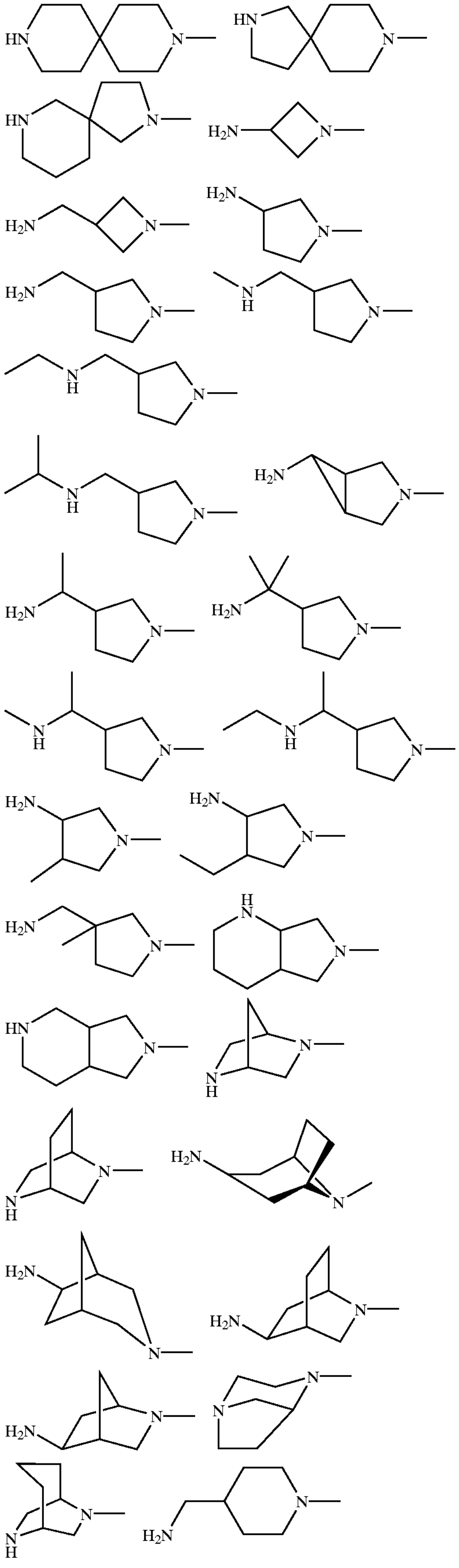

-continued

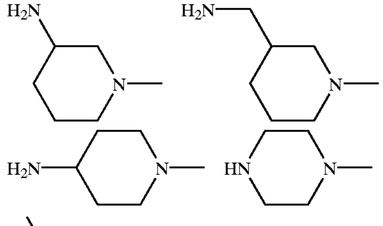

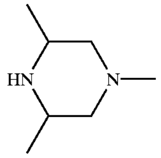 and 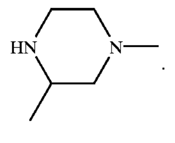.

All of these nitrogen heterocycles are known in the art and are prepared by literature methods such as *J. Med. Chem.*, 1992;35:1764; *J. Med. Chem.*, 1996;39:3070; *Synlett.*, 1996:1097; and *J. Med. Chem.*, 1986;29:445. Any of the primary or secondary amines may be substituted by alkyl.

EXAMPLE A

2-Amino-N-benzyloxy-4,5-difluoro-benzamide

Carbonyldiimidazole (6.1 g, 37 mmol) was added to a suspension of 4,5-difluoroanthranilic acid (5.40 g, 31 mmol) in 250 mL of THF, and the mixture was stirred for 24 hours at 25° C. O-benzylhydroxylamine hydrochloride (4.95 g, 31 mmol) and triethylamine (5.2 mL, 37 mmol) were added, and the mixture was heated to reflux for 4 hours. The reaction mixture was concentrated and washed with 1N HCl, saturated $NaHCO_3$, brine, and dried over magnesium sulfate. The solution was concentrated to give 6.0 g of the title compound as a solid, mp 125–126° C.

EXAMPLE B

3-Benzyloxy-6,7-difluoro-1H-quinazoline-2,4-dione

Phosgene, 12.5% solution in toluene, (16 mL, 20 mmol) was added to a solution of 2-amino-N-benzyloxy-4,5-difluoro-benzamide (Example A, 5.54 g, 19.9 mmol) in 160 mL of dioxane. The solution was heated at reflux for 5 hours and then poured into 450 mL of water. The aqueous solution was extracted with ethyl acetate; the combined organic extracts were washed with water, brine, and dried over magnesium sulfate. The solution was concentrated to give 5.73 g of the title compound as a solid, mp>250° C.

EXAMPLE C

3-Benzyloxy-1-ethyl-6,7-difluoro-1H-quinazoline-2,4-dione

A solution of 3-benzyloxy-6,7-difluoro-1H-quinazoline-2,4-dione (Example B, 3.0 g, 9.9 mmol) in 100 mL of DMF was added to a suspension of sodium hydride (0.47 g, 11.8 mmol) in 40 mL of DMF and stirred for 30 minutes. Ethyl iodide (7.9 mL, 99 mmol) was added, and the mixture was warmed to 50° C. for 18 hours. The reaction was quenched with 1 mL of water and concentrated to an oil. The residue was dissolved in chloroform washed with water, brine, and dried over magnesium sulfate. The solution was concentrated to give 3.2 g of the title compound as a solid, mp 133–135° C.

EXAMPLE D

1-Ethyl-6,7-difluoro-3-hydroxy-1H-quinazoline-2,4-dione

Twenty percent Pd/C was added to a solution of 3-benzyloxy-1-ethyl-6,7-difluoro-1H-quinazoline-2,4-dione (Example C, 0.055 g, 0.16 mmol) in 25 mL of THF and 25 mL of methanol. This was shaken under 50 PSI of hydrogen for 12.5 hours. The mixture was filtered and concentrated to afford 0.03 g of the title compound as a solid, mp 172–174° C.

EXAMPLE E

3-Benzyloxy-1-ethyl-6-fluoro-7-pyrrolidinyl-1H-quinazoline-2,4-dione

Pyrrolidine (0.06 mL, 0.72 mmol) was added to a solution of 3-benzyloxy-1-ethyl-6,7-difluoro-1H-quinazoline-2,4-dione (Example C, 0.2 g, 0.6 mmol) and triethylamine (0.17 mL, 1.2 mmol) in 30 mL of acetonitrile. The solution was warmed to reflux for 3 hours, cooled, and concentrated to a solid. The solid was dissolved in chloroform, washed with 1N HCl, saturated $NaHCO_3$, brine, and dried over magnesium sulfate. The solution was concentrated to give 0.21 g of the title compound as a solid, mp 174–176° C.

EXAMPLE F

3-Benzyloxy-1-ethyl-6-fluoro-7-piperazinyl-1H-quinazoline-2,4-dione

Piperazine (0.06 g, 0.72 mmol) was added to a solution of 3-benzyloxy-1-ethyl-6,7-difluoro-1H-quinazoline-2,4-dione (Example C, 0.2 g, 0.6 mmol) and triethylamine (0.17 mL, 1.2 mmol) in 30 mL of acetonitrile. The solution was warmed to reflux for 24 hours, cooled, and concentrated to a solid. The solid was dissolved in chloroform washed with 1N HCl, saturated $NaHCO_3$, brine, and dried over magnesium sulfate. The solution was concentrated to give 0.13 g of the title compound as a solid, mp 166–167° C.

EXAMPLE G

3-Benzyloxy-1-ethyl-6-fluoro-7-morpholino-1H-quinazoline-2,4-dione

Morpholine (0.06 mL, 0.72 mmol) was added to a solution of 3-benzyloxy-1-ethyl-6,7-difluoro-1H-quinazoline-2,4-dione (Example C, 0.2 g, 0.6 mmol) and triethylamine (0.17 mL, 1.2 mmol) in 30 mL of acetonitrile. The solution was warmed to reflux for 100 hours, cooled, and concentrated to a solid. The solid was dissolved in chloroform washed with 1N HCl, saturated $NaHCO_3$, brine, and dried over magnesium sulfate. The solution was concentrated to give 0.21 g of a solid. The solid was purified by column chromatography (chloroform/methanol 99:1). The appropriate fractions were combined to give 0.17 g of the title compound as a solid.

NMR ($CDCl_3$): δ7.80 (d, 1H), 7.59 (m, 2H), 7.34 (m, 3H), 6.49 (d, 1H), 5.17 (s, 2H), 4.14 (q, 2H), 3.87 (m, 4H), 3.23 (m, 4H), 1.33 (t, 3H).

EXAMPLE H

3-Benzyloxy-1-ethyl-6-fluoro-7-(4-methyl-piperazin-1-yl)-1H-quinazoline-2,4-dione 4-Methylpiperazine (0.08 mL, 0.72 mmol) was added to a solution of 3-benzyloxy-1-ethyl-6,7-difluoro-1H-quinazoline-2,4-dione (Example C, 0.2 g, 0.6 mmol) and DBU (0.09 mL, 0.6 mmol) in 30 mL of acetonitrile. The solution was warmed to reflux for 100 hours, cooled, and concentrated to a solid. The solid was dissolved in chloroform washed with water, brine, and dried over magnesium sulfate. The solution was concentrated to give 0.21 g of a solid. The solid was purified by column chromatography (chloroform/methanol 99:1). The appropriate fractions were combined to give 0.14 g of the title compound as a solid, mp 134–136° C.

EXAMPLE I

3-Benzyloxy-6-fluoro-7-pyrrolidinal-1H-quinazoline-2,4-dione

Pyrrolidine (0.065 mL, 0.8 mmol) was added to a solution of 3-benzyloxy-6,7-difluoro-1H-quinazoline-2,4-dione (Example B, 0.2 g, 0.65 mmol) and triethylamine (0.18 mL, 1.2 mmol) in 30 mL of acetonitrile. The solution was warmed to reflux for 18 hours, cooled, and filtered to give 0.2 g of the title compound as a solid, mp>250° C.

EXAMPLE J 1-(3-Benzyloxy-6-fluoro-1H-2,4-dioxo-1,2,3,4-tetrahydro-quinazolin-7-yl)-pyrrolidin-3-yl]-carbamic acid, tert-butyl ester N-Boc-3-aminopyrrolidine (0.21 g, 1.8 mmol) was added to a solution of 3-benzyloxy-6,7-difluoro-1H-quinazoline-2,4-dione (Example B, 0.2 g, 0.65 mmol) and triethylamine (0.27 mL, 1.8 mmol) in 30 mL of acetonitrile. The solution was warmed to reflux for 120 hours, cooled, and filtered to give 0.22 g of the title compound as a solid, mp>250° C.

EXAMPLE K

3-Benzyloxy-6,7-difluoro-1-methyl-1H-quinazoline-2,4-dione

A solution of 3-benzyloxy-6,7-difluoro-1H-quinazoline-2,4-dione (Example B, 1.5 g, 5 mmol) in 50 mL of DMF was added to a suspension of sodium hydride (0.24 g, 5.9 mmol) in 20 mL of DMF and stirred for 30 minutes. Methyl iodide (3.1 mL, 49 mmol) was added, and the mixture was stirred at 25° C. for 18 hours. The reaction was quenched with 1 mL of water and concentrated to an oil. The residue was dissolved in chloroform, washed with water, brine, and dried over magnesium sulfate. The solution was concentrated to give 1.6 g of the title compound as a solid, mp 167–169° C.

EXAMPLE L 6,7-Difluoro-3-hydroxy-1-methyl-1H-quinazoline-2,4-dione

Twenty percent Pd/C (0.2 g) was added to a solution of 3-benzyloxy-6,7-difluoro-1-methyl-1H-quinazoline-2,4-dione (Example K, 1.55 g, 4.9 mmol) in 25 mL of THF and 25 mL of methanol. The mixture was shaken under 50 PSI of hydrogen for 1.5 hours, and filtered. The catalyst was rinsed with 200 mL of a 50/50 mixture of THF and methanol and concentrated to afford 1.1 g of the title compound as a solid, mp 239–241° C.

General Method 1.

A procedure for the preparation of 2-substituted phenylamino-benzoic acids

A 2.5 M solution of n-butyl lithium (n-BuLi) in hexanes (3.1 equivalents) was added at −5° C. to a solution of diisopropylamine (3 equivalents) in 150 mL of dry THF under nitrogen, and the mixture was stirred for 30 minutes. The reaction mixture was cooled to −78° C. and the appropriate aniline (1 equivalent) was added. The reaction mixture was stirred for 30 minutes, then a solution of a 2-fluorobenzoic acid (1 equivalent) in 50 mL of dry THF was added, and the reaction mixture was allowed to warm to room temperature overnight. Water (100 mL) was added, and the reaction mixture was concentrated, acidified with concentrated HCl to pH 1, and extracted with ether (3×100 mL). Combined ether extracts were washed with 1N hydrochloric acid, water and brine, and dried over sodium sulfate. Solvents were evaporated to give the product as a solid.

EXAMPLE M 2-(4-Hydroxy-anilino)-4,5-difluoro-benzoic acid

Using General Method 1, the reaction of 2.5 M solution of n-BuLi in hexanes (29 mL, 73 mmol), diisopropylamine (9.5 mL, 68 mmol), 4-hydroxyaniline (1.85 g, 17 mmol), and 2,4,5-trifluorobenzoic acid (3 g, 17 mmol) provided 4.5 g of the crude title compound.

EXAMPLE N 2-(4-Fluoro-anilino)-4,5-difluoro-benzoic acid

Using General Method 1, the reaction of 2.5 M solution of n-BuLi in hexanes (14 mL, 35 mmol), diisopropylamine (4.8 mL, 34 mmol), 4-fluoro-aniline (1.1 mL, 11 mmol), and 2,4,5-trifluorobenzoic acid (2 g, 11 mmol) provided 2.59 g of the crude title compound.

EXAMPLE O 2-(4-Methoxy-anilino)-4,5-difluoro-benzoic acid

Using General Method 1, the reaction of 2.5 M solution of n-BuLi in hexanes (26 mL, 64 mmol), diisopropylamine (8.7 mL, 62 mmol), 4-methoxy-aniline (2.6 g, 17 mmol), and 2,4,5-trifluorobenzoic acid (3.6 g, 20.7 mmol) provided 5.72 g of the crude title compound.

EXAMPLE P 2-(3-Chloro-4-fluoro-anilino)-4,5-difluoro-benzoic acid

Using General Method 1, the reaction of 2.5 M solution of n-BuLi in hexanes (21 mL, 53 mmol), diisopropylamine (7.2 mL, 51 mmol), 3-chloro-4-fluoro-aniline (2.48 mL, 17 mmol), and 2,4,5-trifluorobenzoic acid (3.0 g, 17 mmol) provided 4.32 g of the crude title compound.

EXAMPLE Q 2-(3-Methoxy-anilino)-4,5-difluoro-benzoic acid

Using General Method 1, the reaction of 2.5 M solution of n-BuLi in hexanes (21 mL, 53 mmol), diisopropylamine (7.2 mL, 51 mmol), 3-methoxy-aniline (1.91 mL, 17 mmol), and 2,4,5-trifluorobenzoic acid (3.0 g, 17 mmol) provided 4.48 g of the crude title compound.

EXAMPLE R 2-(2-Fluoro-anilino)-4,5-difluoro-benzoic acid

Using General Method 1, the reaction of 2.5 M solution of n-BuLi in hexanes (21 mL, 53 mmol), diisopropylamine (7.2 mL, 51 mmol), 2-fluoro-aniline (1.6 mL, 17 mmol), and 2,4,5-trifluorobenzoic acid (3.0 g, 17 mmol) provided 4.08 g of the crude title compound.

EXAMPLE S 2-(3-Fluoro-anilino)-4,5-difluoro-benzoic acid

Using General Method 1, the reaction of 2.5 M solution of n-BuLi in hexanes (21 mL, 53 mmol), diisopropylamine (7.2 mL, 51 mmol), 3-fluoro-aniline (1.6 mL, 17 mmol), and 2,4,5-trifluorobenzoic acid (3.0 g, 17 mmol) provided 4.24 g of the crude title compound.

EXAMPLE T 2-(2,4,5-Trifluoro anilino)-4,5-difluoro-benzoic acid

Using General Method 1, the reaction of 2.5 M solution of n-BuLi in hexanes (21 mL, 53 mmol), diisopropylamine (7.2 mL, 51 mmol), 2,4,5-trifluoro-aniline (2.5 g, 17 mmol), and 2,4,5-trifluorobenzoic acid (3.0 g, 17 mmol) provided 4.54 g of the crude title compound.

General Method 2.

A procedure for the preparation of 2-substituted phenylamino-N-benzyloxy-benzamides Carbonyldiimidazole (1.1 equivalent) was added to a solution of substituted 2-(anilino)-benzoic acids (1.0 equivalent) in 250 mL of THF, and the mixture was stirred for 24 hours at 25° C. O-benzylhydroxylamine hydrochloride (1 equivalent) and triethylamine (1.1 equivalent) were added, and the mixture was heated to reflux for 4 hours. The reaction mixture was concentrated diluted with ether and washed with 1N HCl, saturated $NaHCO_3$, brine, and dried over sodium sulfate. The solution was concentrated to give the product as an oil.

EXAMPLE U 2-(4-Fluoro-anilino)-N-benzyloxy-4,5-difluoro-benzamide

Using General Method 2, the reaction of carbonyldiimidazole (1.90 g, 11.6 mmol), 2-(4-fluoro-anilino)-4,5-difluorobenzoic acid (Example N, 2.59 g, 9.7 mmol), O-benzylhydroxylamine hydrochloride (1.55 g, 9.7 mmol), and triethylamine (1.63 mL, 11.6 mmol) provided 3.43 g of the crude title compound.

EXAMPLE V 2-(4-Methoxy-anilino)-N-benzyloxy-4,5-difluoro-benzamide

Using General Method 2, the reaction of carbonyldiimidazole (3.6 g, 22.4 mmol), 2-(4-methoxy-anilino)-4,5-difluorobenzoic acid (Example O, 5.72 g, 20.4 mmol), O-benzylhydroxylamine hydrochloride (3.26 g, 20.4 mmol), and triethylamine (3.1 mL, 22.4 mmol) provided 8.0 g of the crude title compound.

EXAMPLE W 2-(3-Chloro-4-fluoro-anilino)-N-benzyloxy-4,5-difluoro-benzamide

Using General Method 2, the reaction of carbonyldiimidazole (2.60 g, 15.7 mmol), 2-(3-chloro-4-fluoro-anilino)-4,5-difluorobenzoic acid (Example P, 4.32 g, 14.3 mmol), O-benzylhydroxylamine hydrochloride (2.3 g, 14.3 mmol), and triethylamine (2.2 mL, 15.7 mmol) provided 6.1 g of the crude title compound.

EXAMPLE X 2-(3-Methoxy-anilino)-N-benzyloxy-4,5-difluoro-benzamide

Using General Method 2, the reaction of carbonyldiimidazole (2.90 g, 17.6 mmol), 2-(3-methoxy-anilino)-4,5-difluorobenzoic acid (Example Q, 4.48 g, 16 mmol), O-benzylhydroxylamine hydrochloride (2.6 g, 16 mmol), and triethylamine (2.5 mL, 17.6 mmol) provided 6.5 g of the crude title compound.

EXAMPLE Y 2-(2-Fluoro-anilino)-N-benzyloxy-4,5-difluoro-benzamide

Using General Method 2, the reaction of carbonyldiimidazole (2.76 g, 16.8 mmol), 2-(2-fluoro-anilino)-4,5-difluorobenzoic acid (Example R, 4.08 g, 15.3 mmol), O-benzylhydroxylamine hydrochloride (2.44 g, 15.3 mmol), and triethylamine (2.3 mL, 16.8 mmol) provided 5.6 g of the crude title compound.

EXAMPLE Z 2-(3-Fluoro-anilino)-N-benzyloxy-4,5-difluoro-benzamide

Using General Method 2, the reaction of carbonyldiimidazole (2.83 g, 17.5 mmol), 2-(3-fluoro-anilino)-4,5-difluorobenzoic acid (Example S, 4.24 g, 15.9 mmol), O-benzylhydroxylamine hydrochloride (2.5 g, 15.9 mmol), and triethylamine (2.4 mL, 17.5 mmol) provided 5.4 g of the crude title compound.

EXAMPLE A-1

2-(2,4,5-Trifluoroanilino)-N-benzyloxy-4,5-difluoro-benzamide

Using General Method 2, the reaction of carbonyldiimidazole (2.85 g, 17.6 mmol), 2-(2,4,5-trifluoro-anilino)-4,5-difluorobenzoic acid (Example T, 4.54 g, 14.7 mmol), O-benzylhydroxylamine hydrochloride (2.34 g, 14.7 mmol), and triethylamine (2.45 mL, 17.6 mmol) provided 6.22 g of the crude title compound.

General Method 3. A procedure for the preparation of 1-substituted phenyl-3-benzyloxy-1H-quinazoline-2,4-diones Carbonyldiimidazole (2 equivalents) was added to a solution of 2-substituted aniline-N-benzyloxy-benzamide (1 equivalent) in 160 mL of THF. The solution was heated at reflux overnight, solvent was evaporated, the residue was dissolved in ethyl acetate and washed with water, 1N HCl, water, brine, and dried over sodium sulfate. The solution was concentrated to give the crude product, which was then purified on silica gel column using a 1/6 (v/v) mixture of ethyl acetate and hexanes, to provide crystalline product.

EXAMPLE B-1

1-(4-Fluorophenyl)-3-benzyloxy-6,7-difluoro-1H-quinazoline-2,4-dione

Using General Method 3, the reaction of carbonyldiimidazole (3.0 g, 18.4 mmol) and crude 2-(4-fluoro-anilino)-N-benzyloxy-4,5-difluoro-benzamide (Example U, 3.43 g, 9.2 mmol) provided 1.8 g of the title compound as a solid, mp 201–202° C.

EXAMPLE C-1

1-(4-Methoxyphenyl)-3-benzyloxy-6,7-difluoro-1H-quinazoline-2,4-dione

Using General Method 3, the reaction of carbonyldiimidazole (6.7 g, 41.6 mmol) and crude 2-(4-methoxy-anilino)-N-benzyloxy-4,5-difluoro-benzamide (Example V, 8.0 g, 20.8 mmol) provided 3.86 g of the title compound as a solid, mp 211–212° C.

EXAMPLE D-1

1-(3-Chloro-4-fluorophenyl)-3-benzyloxy-6,7-difluoro-1H-quinazoline-2,4-dione

Using General Method 3, the reaction of carbonyldiimidazole (4.9 g, 30 mmol) and crude 2-(3-chloro-4-fluoro-anilino)-N-benzyloxy-4,5-difluoro-benzamide (Example W, 6.1 g, 15 mmol) provided 1.27 g of the title compound as a solid, mp 184–186° C.

EXAMPLE E-1

1-(3-Methoxyphenyl)-3-benzyloxy-6,7-difluoro-1H-quinazoline-2,4-dione

Using General Method 3, the reaction of carbonyldiimidazole (5.5 g, 33.8 mmol) and crude 2-(3-methoxy-anilino)-N-benzyloxy-4,5-difluoro-benzamide (Example X, 6.5 g, 16.9 mmol) provided 1.3 g of the title compound as a solid, mp 157–158° C.

EXAMPLE F-1

1-(2-Fluorophenyl)-3-benzyloxy-6,7-difluoro-1H-quinazoline-2,4-dione

Using General Method 3, the reaction of carbonyldiimidazole (4.9 g, 30 mmol) and crude 2-(2-fluoro-anilino)-N-benzyloxy-4,5-difluoro-benzamide (Example Y, 5.6 g, 15 mmol) provided 2.9 g of the title compound as a solid, mp 204–206° C.

EXAMPLE G-1

1-(3-Fluorophenyl)-3-benzyloxy-6,7-difluoro-1H-quinazoline-2,4-dione

Using General Method 3, the reaction of carbonyldiimidazole (4.7 g, 29 mmol) and crude 2-(3-fluoro-anilino)-N-benzyloxy-4,5-difluoro-benzamide (Example Z, 5.4 g, 14.5 mmol) provided 1.8 g of the title compound as a solid, mp 179–181° C.

EXAMPLE H-1

1-(2,4,5-Trifluorophenyl)-3-benzyloxy-6,7-difluoro-1H-quinazoline-2,4-dione

Using General Method 3, the reaction of carbonyldiimidazole (4.9 g, 30.4 mmol) and crude 2-(2,4,5-trifluoro-anilino)-N-benzyloxy-4,5-difluoro-benzamide (Example A-1, 6.22 g, 15.2 mmol) provided 0.35 g of the title compound as a solid.

EXAMPLE I-1

2-(4-Hydroxyanilino)-N-benzyloxy-4,5-difluoro-benzamide

1-Ethyl-3-(3'-dimethylaminopropyl)carbodiimide (EDCI, 0.22 g, 1.1 mmol) and HOBt (0.17 g, 1.1 mmol) were added to a solution of crude 2-(4-hydroxyanilino)-4,5-difluoro-benzoic acid (Example M, 0.265 g, 1.00 mmol) in 70 mL of dichloromethane at 0° C. After 1 hour, O-benzylhydroxylamine hydrochloride (0.176 g, 1.1 mmol), and triethylamine (0.15 mL, 1.1 mmol) were added, and the reaction mixture was allowed to warm to room temperature and stirred overnight. The reaction mixture was diluted with 100 mL of ether and washed with water and 0.1N HCl, water, and brine, dried over sodium sulfate. Solvents were evaporated to give 0.35 g of the title compound as a crude solid.

EXAMPLE J-1

1-(4-Hydroxyphenyl)-3-benzyloxy-6,7-difluoro-1H-quinazoline-2,4-dione

A 2N solution of phosgene in toluene (2.5 mL, 5 mmol) was added to a solution of crude 2-(4-hydroxyanilino)-N-benzyloxy-4,5-difluoro-benzamide (Example I-1, 0.35 g, 0.95 mmol) in 20 mL of dioxane. The solution was heated at reflux for 2 hours, cooled down to room temperature and poured into ice water, and extracted with ethyl acetate (3×30 mL). Combined extracts were washed with water, brine, and dried over sodium sulfate to give 0.065 g of the title product as a solid.

General Method 4. A procedure for the reaction of 1-(substituted phenyl)-3-benzyloxy-1H-quinazoline-2,4-diones with amine nucleophiles The amine nucleophile (3 equivalents) was added to a solution of 1-(substituted phenyl)-3-benzyloxy-6,7-difluoro-1H-quinazoline-2,4-dione (1.0 equivalent) and triethylamine (3 equivalents) in 7 mL of dimethylacetamide (DMA). The solution was heated at 70° C. for 1.5 hours, cooled, and poured into water. The precipitate which formed was collected by filtration, washed with water, and dried to provide the product as a solid.

EXAMPLE K-1

1-(4-Hydroxyphenyl)-6-fluoro-3-benzyloxy-7-pyrrolidin-1-yl-1H-quinazoline-2,4-dione Using General Method 4, the reaction of pyrrolidine (0.04 mL, 0.5 mmol), triethylamine (0.07 mL, 0.5 mmol), and 1-(4-hydroxyphenyl)-3-benzyloxy-6,7-difluoro-1H-quinazoline-2,4-dione (Example J-1, 0.065 g, 0.16 mmol) provided 0.05 g of the title compound as a solid.

EXAMPLE L-1

1-(4-Fluorophenyl)-6-fluoro-3-benzyloxy-7-pyrrolidin-1-yl-1H-quinazoline-2,4-dione Using General Method 4, the reaction of pyrrolidine (0.07 mL, 0.92 mmol), triethylamine (0.08 mL, 0.92 mmol), and 1-(4-fluorophenyl)-3-benzyloxy-6,7-difluoro-1H-quinazoline-2,4-dione (Example B-1, 0.127 g, 0.31 mmol) provided 0.087 g of the title compound as a solid.

EXAMPLE M-1

1-(4-Fluorophenyl)-6-fluoro-3-benzyloxy-7-(4-methylpiperazin-1-yl)-1H-quinazoline-2,4-dione Using General Method 4, the reaction of N-methylpiperazine (0.14 mL, 1.23 mmol), triethylamine (0.17 mL, 1.23 mmol), and 1-(4-fluorophenyl)-3-benzyloxy-6,7-difluoro-1H-quinazoline-2,4-dione (Example B-1, 0.163 g, 0.41 mmol) provided 0.19 g of the title compound as a solid.

EXAMPLE N-1

1-(4-Fluorophenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.28 g, 1.5 mmol), triethylamine (0.2 mL, 1.5 mmol), and 1-(4-fluorophenyl)-3-benzyloxy-6,7-difluoro-1H-quinazoline-2,4-dione (Example B-1, 0.2 g, 0.5 mmol) provided 0.225 g of the title compound as a solid.

EXAMPLE O-1

1-(4-Methoxyphenyl)-6-fluoro-3-benzyloxy-7-pyrrolidin-1-yl-1H-quinazoline-2,4-dione Using General Method 4, the reaction of pyrrolidine (0.125 mL, 1.5 mmol), triethylamine (0.2 mL, 1.5 mmol), and 1-(4-methoxyphenyl)-3-benzyloxy-6,7-difluoro-1H-quinazoline-2,4-dione (Example C-1, 0.20 g, 0.5 mmol) provided 0.21 g of the title compound as a solid.

EXAMPLE P-1

1-(4-Methoxyphenyl)-6-fluoro-3-benzyloxy-7-(4-methylpiperazin-1-yl)-1H-quinazoline-2,4-dione Using General Method 4, the reaction of N-methylpiperazine (0.17 mL, 1.5 mmol), triethylamine (0.2 mL, 1.5 mmol), and 1-(4-methoxyphenyl)-3-benzyloxy-6,7-difluoro-1H-quinazoline-2,4-dione (Example C-1, 0.20 g, 0.5 mmol) provided 0.19 g of the title compound as a solid.

EXAMPLE Q-1

1-(4-Methoxyphenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.28 g, 1.5 mmol), triethylamine (0.2 mL, 1.5 mmol), and 1-(4-methoxyphenyl)-3-benzyloxy-6,7-difluoro-1H-quinazoline-2,4-dione (Example C-1, 0.2 g, 0.5 mmol) provided 0.25 g of the title compound as a solid.

EXAMPLE R-1

1-(3-Chloro-4-fluorophenyl)-6-fluoro-3-benzyloxy-7-(4-methylpiperazin-1-yl)-1H-quinazoline-2,4-dione Using General Method 4, the reaction of N-methylpiperazine (0.12 mL, 1 mmol), triethylamine (0.14 mL, 1 mmol), and 1-(3-chloro-4-fluorophenyl)-3-benzyloxy-6,7-difluoro-1H-quinazoline-2,4-dione (Example D-1, 0.14 g, 0.32 mmol) provided 0.14 g of the title compound as a solid.

EXAMPLE S-1

1-(3-Chloro-4-fluoro-phenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.187 g, 1 mmol), triethylamine (0.14 mL, 1 mmol), and 1-(3-chloro-4-fluorophenyl)-3-benzyloxy-6,7-difluoro-1H-quinazoline-2,4-dione (Example D-1, 0.14 g, 0.32 mmol) provided 0.25 g of the title compound as a solid.

EXAMPLE T-1

1-(3-Methoxyphenyl)-6-fluoro-3-benzyloxy-7-pyrrolidin-1-yl-1H-quinazoline-2,4-dione Using General Method 4, the reaction of pyrrolidine (0.077 mL, 0.9 mmol), triethylamine (0.12 mL, 0.9 mmol), and 1-(3-methoxyphenyl)-3-benzyloxy-6,7-difluoro-1H-quinazoline-2,4-dione (Example E-1, 0.12 g, 0.3 mmol) provided 0.12 g of the title compound as a solid.

EXAMPLE U-1

1-(3-Methoxyphenyl)-6-fluoro-3-benzyloxy-7-(4-methylpiperazin-1-yl)-1H-quinazoline-2,4-dione Using General Method 4, the reaction of N-methylpiperazine (0.1 mL, 0.9 mmol), triethylamine (0.12 mL, 0.9 mmol), and 1-(3-methoxyphenyl)-3-benzyloxy-6,7-difluoro-1H-quinazoline-2,4-dione (Example E-1, 0.12 g, 0.3 mmol) provided 0.12 g of the title compound as a solid.

EXAMPLE V-1

1-(3-Methoxyphenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.162 g, 0.9 mmol), triethylamine (0.12 mL, 0.9 mmol), and 1-(3-methoxyphenyl)-3-benzyloxy-6,7-difluoro-1H-quinazoline-2,4-dione (Example E-1, 0.12 g, 0.3 mmol) provided 0.15 g of the title compound as a solid.

EXAMPLE W-1

1-(2-Fluorophenyl)-6-fluoro-3-benzyloxy-7-pyrrolidin-1-yl-1H-quinazoline-2,4-dione Using General Method 4, the reaction of pyrrolidine (0.063 mL, 0.75 mmol), triethylamine (0.106 mL, 0.75 mmol), and 1-(2-fluorophenyl)-3-benzyloxy-6,7-difluoro-1H-quinazoline-2,4-dione (Example F-1, 0.1 g, 0.25 mmol) provided 0.1 g of the title compound as a solid.

EXAMPLE X-1

1-(2-Fluorophenyl)-6-fluoro-3-benzyloxy-7-(4-methylpiperazin-1-yl)-1H-quinazoline-2,4-dione Using General Method 4, the reaction of N-methylpiperazine (0.083 mL, 0.75 mmol), triethylamine (0.106 mL, 0.75 mmol), and 1-(2-fluorophenyl)-3-benzyloxy-6,7-difluoro-1H-quinazoline-2,4-dione (Example F-1, 0.1 g, 0.25 mmol) provided 0.12 g of the title compound as a solid.

EXAMPLE Y-1

1-(3-Fluorophenyl)-6-fluoro-3-benzyloxy-7-pyrrolidin-1-yl-1H-quinazoline-2,4-dione Using General Method 4, the reaction of pyrrolidine (0.1 mL, 1.28 mmol), triethylamine (0.18 mL, 1.28 mmol), and 1-(3-fluorophenyl)-3-benzyloxy-6,7-difluoro-1H-quinazoline-2,4-dione (Example G-1, 0.17 g, 0.43 mmol) provided 0.1 g of the title compound as a solid.

EXAMPLE Z-1

1-(3-Fluorophenyl)-6-fluoro-3-benzyloxy-7-(4-methylpiperazin-1-yl)-1H-quinazoline-2,4-dione Using General Method 4, the reaction of N-methylpiperazine (0.16 mL, 1.43 mmol), triethylamine (0.2 mL, 1.43 mmol), and 1-(3-fluorophenyl)-3-benzyloxy-6,7-difluoro-1H-quinazoline-2,4-dione (Example G-1, 0.19 g, 0.48 mmol) provided 0.209 g of the title compound as a solid.

EXAMPLE A-2

1-(3-Fluorophenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.266 g, 1.43 mmol), triethylamine (0.2 mL, 1.43 mmol), and 1-(3-fluorophenyl)-3-benzyloxy-6,7-difluoro-1H-quinazoline-2,4-dione (Example G-1, 0.19 g, 0.48 mmol) provided 0.231 g of the title compound as a solid.

EXAMPLE B-2

1-(2,4,5-Trifluorophenyl)-6-fluoro-3-benzyloxy-7-(3-t-butoxycarbonylamino-pyrrolidin-1-yl)-1H-quinazoline-2,4-dione Using General Method 4, the reaction of 3-t-butoxycarbonylamino-pyrrolidine (0.231 g, 1.24 mmol), triethylamine (0.178 mL, 1.24 mmol), and 1-(2,4,5-trifluorophenyl)-3-benzyloxy-6,7-difluoro-1H-quinazoline-2,4-dione (Example H-1, 0.18 g, 0.41 mmol) provided 0.13 g of the title compound as a solid.

EXAMPLE C-2

Ethyl 2-chloro-5-fluoro-6-pyrrolidinyl-3-pyridinecarboxylate

To a solution of ethyl 2,6-dichloro-5-fluoro-3-pyridinecarboxylate (3.00 g, 12.6 mmol: *J. Med. Chem.*, 1986;29:2363) and triethylamine (2.63 mL, 18.90 mmol) in acetonitrile (15 mL) was added pyrrolidine (1.05 mL, 12.6 mmol) dropwise. After being stirred at 60° C. for 1 hour, the reaction mixture was evaporated, and the residue was dissolved in dichloromethane, washed with water, and dried over anhydrous sodium sulfate. The residue was purified on a silica gel column using hexane/dichloromethane (7:3) as eluent giving 2.5 g of the title compound as a solid, mp 95° C.

EXAMPLE D-2

Ethyl 2-chloro-5-fluoro-6-(4-methylpiperazinyl)-3-pyridinecarboxylate

Following the procedure of Example C-2, the reaction of 2,6-dichloro-5-fluoro-3-pyridinecarboxylate (2.00 g, 8.4 mmol) with 4-methylpiperazine (0.95 mL, 8.4 mmol) in acetonitrile (10 mL) in the presence of triethylamine (1.75 mL, 12.58 mmol) gave 2.34 g of the title compound as an oil.

EXAMPLE E-2

Ethyl 2-cyclopropylamino-5-fluoro-6-pyrrolidinyl-3-pyridinecarboxylate

A solution of ethyl 2-chloro-5-fluoro-6-pyrrolidinyl-3-pyridinecarboxylate (Example C-2, 500 mg, 1.83 mmol) and cyclopropylamine (2 mL) in DMA (1 mL) was sealed in a pressure bottle and heated at 90° C. for 1 day. The reaction mixture was diluted with dichloromethane (40 mL), washed with water, and dried on sodium sulfate. Flash chromatography on a silica gel column using dichloromethane/hexane (3:2) as eluent provided 270 mg of the title compound as an oil.

EXAMPLE F-2

Ethyl 2-cyclopropylamino-5-fluoro-6-(4-methylpiperazinyl)-3-pyridinecarboxylate

A solution of ethyl 2-chloro-5-fluoro-6-(4-methylpiperazinyl)-3-pyridine-carboxylate (Example D-2, 1.00 g, 3.314 mmol) and cyclopropylamine (2 mL) in DMA (1 mL) was sealed in a pressure bottle and heated at 90° C. for 60 hours. The reaction mixture was diluted with dichloromethane (30 mL), washed with water, and dried on sodium sulfate. Flash chromatography on silica gel column using dichloromethane as eluent provided compound 0.85 g of the title compound as an oil.

EXAMPLE G-2

2-Cyclopropylamino-5-fluoro-6-pyrrolidinyl-3-pyridinecarboxylic acid

A solution of ethyl 2-cyclopropylamino-5-fluoro-6-pyrrolidinyl-3-pyridine-carboxylate (Example E-2, 270 mg, 0.92 mmol) and NaOH (360 mg, 9.0 mmol) in water (1 mL), THF (2 mL), and MeOH (1 mL) was refluxed for 3 hours. The mixture was cooled to room temperature, acidified with dilute HCl to pH 6, and evaporated under reduced pressure. The residue was mixed with 10% MeOH/dichloromethane (40 mL), dried on sodium sulfate, filtered, and evaporated. The solid residue was further washed with hexane and dried in vacuo, giving 215 mg of the title compound as powder, mp 64–66° C.

EXAMPLE H-2

2-Cyclopropylamino-5-fluoro-6-(4-methylpiperazinyl)-3-pyridinecarboxylic acid

Following the procedure of Example G-2, the reaction of ethyl 2-cyclopropylamino-5-fluoro-6-(4-methylpiperazinyl)-3-pyridinecarboxylate (Example F-2, 0.86 g, 2.67 mmol) with NaOH (1.40 g, 35 mmol) in THF (5 mL) and water (2 mL) provided 0.50 g of the title compound as a foam.

EXAMPLE I-2

N-Benzyloxy-2-cyclopropylamino-5-fluoro-6-pyrrolidinyl-3-pyridinecarboxamide

To a solution of 2-cyclopropylamino-5-fluoro-6-pyrrolidinyl-3-pyridinecarboxylic acid (Example G-2, 215 mg, 0.80 mmol) and 1-hydroxybenzotriazole (HOBT) (119 mg, 0.88 mmol) in chloroform (10 mL) was added 1-ethyl-3-(3'-dimethylamino-propyl)carbodiimide (EDCI) (169 mg, 0.88 mmol). After being stirred at room temperature for 30 minutes, O-benzylhydroxylamine hydrochloride (141 mg, 0.88 mmol) and triethylamine (0.122 mL, 0.88 mmol) were added. The reaction mixture was heated to reflux for 4 hours, diluted with dichloromethane, washed with water, and dried on sodium sulfate. The residue was purified by flash chromatography on a silica gel column with dichloromethane as eluent giving 155 mg of the title compound as an oil.

EXAMPLE J-2

N-Benzyloxy-2-cyclopropylamino-5-fluoro-6-(4-methylpiperazinyl)-3-pyridinecarboxamide Following the procedure of Example I-2, the reaction of 2-cyclopropylamino-5-fluoro-6-(4-methylpiperazinyl)-3-pyridinecarboxylic acid (Example H-2, 200 mg, 0.67 mmol) and HOBT (99.5 mg, 0.74 mmol) with EDCI (154.6 mg, 0.81 mmol) in dichloromethane (10 mL) followed by adding O-benzylhydroxylamine hydrochloride (0.81 mmol) and triethylamine (0.113 mL, 0.81 mmol) gave a crude oil. Purification of the oil by flash chromatography on a silica gel column with 5% of MeOH in dichloromethane provided 160 mg of the title compound as an oil.

EXAMPLE K-2

3-Benzyloxy-1-cyclopropyl-6-fluoro-7-pyrrolidinyl-1H-pyrido[2,3-d]pyrimidine-2,4-dione A solution of N-benzyloxy-2-cyclopropylamino-5-fluoro-6-pyrrolidinyl-3-pyridinecarboxamide (Example I-2, 155 mg, 0.44 mmol) and 1,1'-carbonyldiimidazole (CDI) (142 mg, 0.88 mmol) in chloroform (2 mL) was refluxed overnight. The mixture was concentrated and purified by flash chromatography on a silica gel column with dichloromethane as eluent giving 130 mg of the title compound as a solid, mp 184–186° C.

EXAMPLE L-2

3-Benzyloxy-1-cyclopropyl-6-fluoro-7-(4-methylpiperazinyl)-1H-pyrido[2,3-d]pyrimidine-2,4-dione Following the procedure of Example K-2, the reaction of N-benzyloxy-2-cyclopropylamino-5-fluoro-6-(4-methylpiperazinyl)-3-pyridinecarboxamide (Example J-2, 160 mg, 0.42 mmol) with CDI (135 mg, 0.83 mmol) in chloroform (2 mL) and purification of the reaction mixture by flash chromatography on a silica gel with 5% of MeOH/dichloromethane as eluent provided 125 mg of the title compound as powder, mp 188–189° C.

EXAMPLE M-2

N-Benzyloxy-2,6-dichloro-5-fluoro-3-pyridinecarboxamide

To a suspension of 2,6-dichloro-5-fluoro-3-pyridinecarboxylic acid (20.00 g, 95.2 mmol) and a few drops of DMF in dichloromethane (200 mL) was added oxalyl chloride (24.6 mL, 0.282 mol) dropwise. The mixture was stirred at room temperature until evolution of gas ceased, and the reaction mixture was evaporated under reduced pressure to remove excess of the reagent. The residue was dissolved in dichloromethane (200 mL) and O-benzylhydroxylamine hydrochloride (16.71 g, 0.105 mol) in dichloromethane (200 mL) and triethylamine (15.90 mL, 0.114 mmol) were added dropwise at 0° C. The mixture was stirred at room temperature for 3 hours, diluted with ethyl acetate (100 mL), washed with saturated aqueous sodium hydrogen carbonate, water, and dried on sodium sulfate. The solid residue was recrystallized from chloroform to give 14.87 g of the title compound as solid, mp 176–177° C.

General Method 5. A procedure for the synthesis of 1-substituted-3-benzyloxy-7-chloro-6-fluoro-1H-pyrido[2,3-d]pyrimidine-2,4-dione To a solution of N-benzyloxy-2,6-dichloro-5-fluoro-3-pyridinecarboxamide (Example M-2, 2.00 g, 6.34 mmol) in anhydrous dimethylacetamide (DMA) (25 mL) was added 60% NaH in oil (300 mg, 7.52 mmol). After bubbling of hydrogen ceased, an alkyl or aryl isocyanate (1.5–4.0 equiv.) was added, and the reaction mixture was stirred at room temperature for 1 to 10 hours and quenched with water (200 mL). The solid precipitate was collected by filtration, dissolved in dichloromethane, washed with water, and dried on sodium sulfate. Concentration of the organic layers often gave additional solid product, which were further washed with 20% of dichloromethane/hexane or recrystallized from chloroform.

EXAMPLE N-2

3-Benzyloxy-7-chloro-1-ethyl-6-fluoro-1H-pyrido[2,3-d]pyrimidine-2,4-dione

Using the General Method 5, the reaction of N-benzyloxy-2,6-dichloro-5-fluoro-3-pyridinecarboxamide (Example M-2, 2.00 g, 6.34 mmol) and 60% NaH in oil (380 mg, 9.52 mmol) with ethyl isocyanate (2.0 mL, 25.36 mmol) in DMA afforded 1.725 g of the title compound as a solid, mp 156–157° C.

EXAMPLE O-2

3-Benzyloxy-1-butyl-7-chloro-6-fluoro-1H-pyrido[2,3-d]pyrimidine-2,4-dione

Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with n-butyl isocyanate (2.14 mL, 19.02 mmol) in DMA afforded crude product. Recrystallization from chloroform provided 1.40 g of the title compound as a solid, mp 147–148° C.

EXAMPLE P-2

1-Benzyl-3-benzyloxy-7-chloro-6-fluoro-1H-pyrido[2,3-d]pyrimidine-2,4-dione

Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with benzyl isocyanate (1.17 mL, 9.51 mmol) in DMA afforded crude product. Recrystallization from chloroform provided 2.15 g of the title compound as a solid, mp 209–210° C.

EXAMPLE Q-2

3-Benzyloxy-7-chloro-6-fluoro-1-(4-fluorophenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 4-fluorophenyl isocyanate (0.86 mL, 9.51 mmol) in DMA afforded 1.89 g of the title compound as a solid, mp 208–209° C.

EXAMPLE R-2

3-Benzyloxy-7-chloro-6-fluoro-1-(2-fluorophenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 2-fluorophenyl isocyanate (1.07 mL, 9.51 mmol) in DMA afforded 2.05 g of the title compound as a solid, mp 199–200° C.

EXAMPLE S-2

3-Benzyloxy-7-chloro-1-(2,4-difluorophenyl)-6-fluoro-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 2,4-difluorophenyl isocyanate (1.13 mL, 9.51 mmol) in DMA afforded 2.28 g of the title compound as a solid, mp 215–216° C.

EXAMPLE T-2

3-Benzyloxy-7-chloro-6-fluoro-1-(4-methylphenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 4-methylphenyl isocyanate (1.20 mL, 9.51 mmol) in DMA afforded crude product. Recrystallization from chloroform provided 1.91 g of the title compound as a solid, mp 218–219° C.

EXAMPLE U-2

3-Benzyloxy-7-chloro-6-fluoro-1-(4-trifluoromethylphenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 4-trifluoromethylphenyl isocyanate (1.36 mL, 9.51 mmol) in DMA afforded 1.97 g of the title compound as a solid, mp 245–246° C.

EXAMPLE V-2

3-Benzyloxy-7-chloro-6-fluoro-1-(3-trifluoromethylphenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 3-trifluoromethylphenyl isocyanate (1.31 mL, 9.51 mmol) in DMA afforded 2.04 g of the title compound as a solid, mp 207–208° C.

EXAMPLE W-2

3-Benzyloxy-7-chloro-6-fluoro-1-(4-methoxyphenyl)-1H-pyrido[2,3-d]pyrimidine-2,4-dione Using the General Method 5, the reaction of N-benzyloxy-2,6-dichloro-5-fluoro-3-pyridinecarboxamide (Example M-2, 2.00 g, 6.34 mmol) and 60% NaH in oil (300 mg, 7.52 mmol) with 4-methoxyphenyl isocyanate (1.31 mL, 9.51 mmol) in DMA afforded crude product. Recrystallization from chloroform provided 1.85 g of the title compound as a solid, mp 238–240° C.

EXAMPLE X-2

3-Benzyloxy-1-ethyl-6-fluoro-7-pyrrolidinyl-1H-pyrido[2,3-d]pyrimidine-2,4-dione To a solution of 3-benzyloxy-7-chloro-1-ethyl-6-fluoro-1H-pyrido[2,3-d]-pyrimidine-2,4-dione (Example N-2, 146 mg, 0.42 mmol) in dichloromethane (3 mL) was added pyrrolidine (0.070 mL, 0.84 mmol) and the mixture was stirred at room temperature for 10 minutes. The reaction was diluted with dichloromethane (10 mL). The organic phase was washed with saturated aqueous sodium bicarbonate, dried on $MgSO_4$, and concentrated. Washing the solid residue with hexane afforded 120 mg of the title compound as a solid, mp 189–190° C.

EXAMPLE Y-2

3-Benzyloxy-1-ethyl-6-fluoro-7-(4-methylpiperazinyl)-1H-pyrido[2,3-d]pyrimidine-2,4-dione Following the procedure of Example X-2, the reaction of 3-benzyloxy-7-chloro-1-ethyl-6-fluoro-1H-pyrido[2,3-d]pyrimidine-2,4-dione (Example N-2, 200 mg, 0.572 mmol) with 4-methylpiperazine (0.152 mL, 1.37 mmol) in dichloromethane (3 mL) afforded 200 mg of the title compound as a solid, mp 178–179° C.

EXAMPLE Z-2

3-Benzyloxy-1-ethyl-6-fluoro-7-[3-(N-tert-butoxycarbonylamino)pyrrolidin-1-yl]-1H-pyrido[2,3-d]pyrimidine-2,4-dione Following the procedure of Example X-2, the reaction of 3-benzyloxy-7-chloro-1-ethyl-6-fluoro-1H-pyrido[2,3-d]pyrimidine-2,4-dione (Example N-2, 200 mg, 0.572 mmol) with 3-(N-tert-butoxycarbonylamino)pyrrolidine (117 mg, 0.629 mmol) in dichloromethane (5 mL) in the presence of triethylamine (0.087 mL) afforded 245 mg of the title compound as a solid, mp 157–159° C.

EXAMPLE A-3

1-Benzyl-3-benzyloxy-6-fluoro-7-pyrrolidinyl-1H-pyrido[2,3-d]pyrimidine-2,4-dione Following the procedure of Example X-2, the reaction of 1-benzyl-3-benzyloxy-7-chloro-6-fluoro-1H-pyrido[2,3-d]pyrimidine-2,4-dione (Example P-2, 142 mg, 0.345 mmol) with pyrrolidine (0.070 mL, 0.828 mmol) in dichloromethane (3 mL) afforded 121 mg of the title compound as a solid. mp 171–172° C.

EXAMPLE B-3

4-Chloro-2-cyclopropylamino-5-fluoro-benzoic acid, ethyl ester

A mixture of 4-chloro-2,5-difluorobenzoic acid (5.0 g, 26 mmol) and dichloromethane (150 mL) was reacted with oxalyl chloride (6.0 mL, 69 mmol) and one drop of DMF. The mixture was stirred for 1.5 hours, then concentrated. The residue was then dissolved in dichloromethane (200 mL) and reacted with ethanol (40 mL). After 30 minutes, the mixture was diluted with diethyl ether and washed with 1.0 N NaOH. The organic layer was then dried with sodium sulfate and the solvent concentrated. The residue was then taken up in acetonitrile (40 mL) and heated with an excess of cyclopropyl amine (20 mL) for 48 hours at 80° C. The mixture was cooled to ambient temperature and the solvent concentrated. The residue was then taken up in diethyl ether and washed with water. The organic layer was dried with sodium sulfate and concentrated. The resulting residue was purified by column chromatography (silica gel, gradient dilution of hexanes to 20% ethyl acetate/hexanes) to provide a 4.16 g of the title compound as a solid.

EXAMPLE C-3

4-Chloro-2-cyclopropylamino-5-fluoro-benzoic acid

A solution of 4-chloro-2-cyclopropylamino-5-fluoro-benzoic acid ethyl ester (Example B-3, 4.10 g, 15.9 mmol) in THF (100 mL) was reacted with an aqueous solution of 1.0 N LiOH (45 mL, 45 mmol) and methanol (40 mL) and allowed to stir overnight. The mixture was then concentrated to one-third volume and acidified with 1.0 N HCl. The mixture was extracted with ethyl acetate, the organic layers combined, dried with sodium sulfate, and concentrated to provide 3.0 g of the title compound as an oil.

EXAMPLE D-3

N-Benzyloxy-4-chloro-2-cyclopropylamino-5-fluoro-benzamide

Following the procedure of Example A, 4-chloro-2-cyclopropylamino-5-fluoro-benzoic acid (Example C-3, 2.0 g, 8.7 mmol) was reacted with carbonyldiimidazole (1.7 g, 10.5 mmol), O-benzylhydroxylamine hydrochloride (1.67 g, 10.5 mmol), and triethylamine (1.5 mL, 10.5 mmol) in THF (50 mL) to give 2.92 g of the title compound.

EXAMPLE E-3

3-Benzyloxy-7-chloro-1-cyclopropyl-6-fluoro-1H-quinazoline-2,4-dione

A solution of N-benzyloxy-4-chloro-2-cyclopropylamino-5-fluoro-benzamide (Example D-3, 3.00 g, 8.96 mmol) in 1,4-dioxane (50 mL) was reacted with a 20% solution of phosgene (7.00 mL, 9.86 mmol) in toluene in a sealed tube. The mixture was heated to reflux for 24 hours, then cooled and quenched with $H_2O$. The mixture was extracted three times with ethyl acetate, the organic layers combined, dried with sodium sulfate, and concentrated. The residue was then purified by column chromatography (silica gel, 1:1 hexanes/ethyl acetate) to provide 1.5 g of the title compound as a solid.

EXAMPLE F-3

3-Benzyloxy-1-cyclopropyl-6-fluoro-7-pyrrolidin-1-yl-1H-quinazoline-2,4-dione

A solution of 3-benzyloxy-7-chloro-1-cyclopropyl-6-fluoro-1H-quinazoline-2,4-dione (Example E-3, 0.15 g, 0.42 mmol) in DMF (4.0 mL) was reacted with pyrrolidine (1.0 mL) and heated to 70° C. overnight. The mixture was then cooled, diluted with 0.25 M HCl, and extracted with ethyl acetate. The organic layers were combined, dried with sodium sulfate, and concentrated. The residue was then purified by column chromatography (silica gel, 1:1 hexanes/ethyl acetate) to provide 0.15 g of the title compound as a solid.

EXAMPLE G-3

[1-(3-Benzyloxy-1-cyclopropyl-6-fluoro-2,4-dioxo-1,2,3,4-tetrahydro-quinazolin-7-yl)-pyrrolidin-3-yl]-carbamic acid tert-butyl ester A solution of 3-benzyloxy-7-chloro-1-cyclopropyl-6-fluoro-1H-quinazoline-2,4-dione (Example E-3, 0.15 g, 0.42 mmol) in DMF (3.0 mL) was reacted with pyrrolidin-3-yl-carbamic acid tert-butyl ester (0.700 g, 3.5 mmol) and triethylamine (0.70 mL, 5.0 mmol) then heated to 70° C. overnight. The mixture was then cooled, diluted with $H_2O$, and extracted with ethyl acetate. The organic layers were combined, dried with sodium sulfate, and concentrated. The residue was then purified by column chromatography (silica gel, 1:1 hexanes/ethyl acetate) to provide 0.10 g of the title compound as a solid.

EXAMPLE H-3

[1-(3-Benzyloxy-1-cyclopropyl-6-fluoro-2,4-dioxo-1,2,3,4-tetrahydro-quinazolin-7-yl)-pyrrolidin-3-yl-methyl]-carbamic acid tert-butyl ester A solution of 3-benzyloxy-7-chloro-1-cyclopropyl-6-fluoro-1H-quinazoline-2,4-dione (Example E-3, 0.162 g, 0.44 mmol) in DMF (3.0 mL) was reacted with pyrrolidin-3-yl-methyl-carbamic acid tert-butyl ester (0.40 g, 2.0 mmol) and triethylamine (0.63 mL, 4.5 mmol) then heated to 70° C. for 2 days. The mixture was then cooled, diluted with $H_2O$, and extracted with ethyl acetate. The organic layers were combined, dried with sodium sulfate, and concentrated. The residue was then purified by column chromatography (silica gel, 1:1 hexanes/ethyl acetate) to provide 0.127 g of the title compound as a solid.

EXAMPLE I-3

[1-(3-Benzyloxy-1-cyclopropyl-6-fluoro-2,4-dioxo-1,2,3,4-tetrahydro-quinazolin-7-yl)-azetidin-3-yl]-carbamic acid tert-butyl ester A solution of 3-benzyloxy-7-chloro-1-cyclopropyl-6-fluoro-1H-quinazoline-2,4-dione (Example E-3, 0.20 g, 0.55 mmol) in DMA (3.0 mL) was reacted with azetidin-3-yl-carbamic acid tert-butyl ester (0.286 g, 1.66 mmol), triethylamine (0.76 mL, 5.5 mmol) and heated to 80° C. for 2 days. The mixture was then cooled, diluted with $H_2O$, and extracted with ethyl acetate. The organic layers were combined, dried with sodium sulfate, and concentrated. The residue was purified by column chromatography (silica gel, 3:1 hexanes/ethyl acetate to 1:1 hexanes/ethyl acetate) to provide 0.13 g of the title compound as a solid.

EXAMPLE J-3

(1α,5α,6α)[3-(3-Benzyloxy-1-cyclopropyl-6-fluoro-2,4-dioxo-1,2,3,4-tetrahydro-quinazolin-7-yl)-3-aza-bicyclo[3.1.0]hex-6-yl]-carbamic acid tert-butyl ester A solution of 3-benzyloxy-7-chloro-1-cyclopropyl-6-fluoro-1H-quinazoline-2,4-dione (Example E-3, 0.20 g, 0.55 mmol) in DMSO (3.0 mL) was reacted with 3-aza-bicyclo[3.1.0]hex-6-yl-carbamic acid tert-butyl ester (0.22 g, 1.1 mmol) and triethylamine (0.76 mL, 5.5 mmol), then heated to 100° C. for 2 days. The mixture was cooled, diluted with $H_2O$, and extracted with ethyl acetate. The organic layers were combined, washed with saturated aqueous LiCl, dried with sodium sulfate, and concentrated. The residue was purified by column chromatography (silica gel, 1:1 hexanes/ethyl acetate) to provide 0.195 g of the title compound as a solid.

EXAMPLE K-3

[4αR-(4αα,7αα)]6-(3-Benzyloxy-1-cyclopropyl-6-fluoro-2,4-dioxo-1,2,3,4-tetrahydro-quinazolin-7-yl)-octahydro-pyrrolo[3,4-b]pyridine-1-carboxylic acid tert-butyl ester A solution of 3-benzyloxy-7-chloro-1-cyclopropyl-6-fluoro-1H-quinazoline-2,4-dione (Example E-3, 0.16 g, 0.44 mmol) in DMSO (3.0 mL) was reacted with octahydro-pyrrolo[3,4-b]pyridine-1-carboxylic acid tert-butyl ester (0.402 g, 1.8 mmol), triethylamine (0.28 mL, 2.0 mmol) and heated to 100° C. for 3 days. The mixture was then cooled, diluted with $H_2O$, and extracted with ethyl acetate. The organic layers were combined, washed with saturated aqueous LiCl, dried with sodium sulfate, and concentrated. The residue was purified by column chromatography (silica gel, 1:1 hexanes/ethyl acetate) to provide 0.22 g of the title compound as an oil.

EXAMPLE L-3

7,8-Difluoro-4H-benzo[1,4]thiazin-3-one

A solution of 1,2,3-trifluoro-4-nitrobenzene (6.0 g, 34 mmol) in ethanol (15 mL) was reacted with methylthioglycolate (3.66 mL, 40.7 mmol) and $NaHCO_3$ (3.42 g, 40.7 mmol) and the mixture heated to reflux for 4 hours. The mixture was then cooled, diluted with ethyl acetate, and washed with 1.0N NaOH. The organic layer was then dried with sodium sulfate and the solvent concentrated. The residue was purified by column chromatography (silica gel, 1:1 hexanes/dichloromethane) to provide a solid (5.89 g) as a mixture of isomers, which was taken up in acetic acid (90 mL) and ethanol (50 mL) in a 3-necked flask equipped with a mechanical stirrer. The mixture was reacted with reduced iron powder (5.0 g) and the mixture heated to reflux ($N_2$ atmosphere) for 5 hours and cooled. The mixture was concentrated, taken up with ethyl acetate, and subsequently filtered. The filtrate was washed with saturated $NaHCO_3$, the organic layer dried with sodium sulfate and concentrated to provide 2.4 g of the title compound as a solid.

$^1H$ NMR (300 MHz, DMSO-$d_6$) δ 3.53 (s, 2H), 6.75–6.80 (m, 1H), 7.26 (q, 1H, J=9 Hz), 10.76 (bs, 1H).

EXAMPLE M-3

7,8-Difluoro-3,4-dihydro-2H-benzo[1,4]thiazine

A solution of 7,8-difluoro-4H-benzo[1,4]thiazin-3-one (Example L-3, 2.27 g, 11.3 mmol) in THF (100 mL) was reacted with lithium aluminumhydride (1.07 g, 28.2 mmol) under an $N_2$ atmosphere and heated to reflux overnight. The mixture was cooled and quenched with 1.0N HCl and extracted with ethyl acetate. The organic layers were combined, dried with sodium sulfate, and concentrated to provide 2.2 g of the title compound as an oil.

EXAMPLE N-3

6,7-Difluoro-3,4-dihydro-5-thia-2α-aza-acenaphthylene-1,2-dione

A solution of chloral hydrate (2.22 g, 13.3 mmol), sodium sulfate 10 $H_2O$ (86.0 g, 267 mmol), and hydroxylamine hydrochloride (2.78 g, 40.1 mmol) in $H_2O$ (200 mL) was reacted with a mixture of 7,8-difluoro-3,4-dihydro-2H-benzo[1,4]thiazine (Example M-3, 2.20 g, 13.4 mmol), 1.0 M aqueous HCl (13.4 mL), and methanol (5.0 mL). The reaction was heated to 100° C. overnight. The mixture was cooled, extracted with ethyl acetate, the organic layers combined, dried with sodium sulfate, and concentrated. The residue was reacted with concentrated $H_2SO_4$ (20 mL) and heated to 50° C. for 30 minutes. The mixture was quenched with $H_2O$ and extracted with ethyl acetate. The organic layers were combined, dried with sodium sulfate and concentrated to provide 2.05 g of the title compound as an oil.

EXAMPLE O-3

5-Benzyloxy-8,9-difluoro-2,3-dihydro-1-thia-3α,5-diaza-phenalene-4,6-dione 6,7-Difluoro-3,4-dihydro-5-thia-2α-aza-acenaphthylene-1,2-dione (Example N-3, 2.05 g) was dissolved in methanol (150 mL), reacted with a 1.0 M aqueous solution of NaOH (36 mL), cooled to 0° C., and reacted with 30% $H_2O_2$ (2.8 mL, 34 mmol). The mixture was stirred for 1.5 hours, then quenched with an excess of $Na_2S_2O_3$ and allowed to stir for 20 minutes acidified with a 1.0 N solution of HCl. The mixture was extracted with ethyl acetate, the organic layer dried with sodium sulfate, and concentrated. The residue was dissolved in diethyl ether and extracted with 1.0N aqueous NaOH. The aqueous layers were combined, acidified with concentrated HCl, and the mixture extracted with ethyl acetate three times. The organic layers were combined, dried with sodium sulfate, and concentrated. The residue (1.7 g) was then dissolved in THF (40 mL) and reacted with carbonyldiimidazole (1.49 g, 9.19 mmol). The mixture was heated to 60° C. ($N_2$ atmosphere) for 4 hours and subsequently cooled and reacted with O-benzylhydroxylamine hydrochloride (2.93 g, 18.4 mmol) and triethylamine (2.56 mL, 18.4 mmol). The mixture was then heated to reflux overnight, cooled, and diluted with 0.5 N HCl. The product was extracted with ethyl acetate, the organic layers combined, dried with sodium sulfate, and concentrated. The residue was suspended in THF (100 mL) and reacted with carbonyldiimidazole. The mixture was refluxed for 3 days, cooled, concentrated under reduced pressure, diluted with 1.0 N HCl, and extracted with ethyl acetate. The organic layers were combined, diluted with methanol, dried with sodium sulfate, and concentrated. The resulting solid was washed with a 1:1 mixture of diethyl ether/hexanes to provide 1.91 g of the title compound.

$^1H$ NMR (300 MHz, $CDCl_3$) δ 3.20–3.40 (m, 2H, partially obscured by $H_2O$), 4.29–4.32 (m, 2H), 5.12 (s, 2H), 7.37–7.45 (m, 3H), 7.55–7.58 (m, 2H), 7.83 (t, 1H, J=9 Hz).

EXAMPLE P-3

5-Benzyloxy-8-fluoro-9-pyrrolidin-1-yl-2,3-dihydro-1-thia-3α,5-diaza-phenalene-4,6-dione A solution of 5-benzyloxy-8,9-difluoro-2,3-dihydro-1-thia-3α,5-diaza-phenalene-4,6-dione (Example O-3, 0.150 g, 0.41 mmol) in DMF (3.0 mL) was reacted with pyrrolidine (0.105 mL, 1.23 mmol) and triethylamine (0.17 mL, 1.23 mmol), and then heated to 50° C. overnight. The mixture was cooled, diluted with $H_2O$, and extracted with ethyl acetate. The organic layers were combined, dried with sodium sulfate, and concentrated. The residue was then purified by column chromatography (silica gel, 7:3 hexanes/ethyl acetate) to provide 0.13 g of the title compound as a solid.

EXAMPLE Q-3

[1-(5-Benzyloxy-8-fluoro-4,6-dioxo-2,3,5,6-tetrahydro-4H-1-thia-3α,5-diaza-phenalene-9-yl)-pyrrolidin-3-yl]-carbamic acid tert-butyl ester A solution of 5-benzyloxy-8,9-difluoro-2,3-dihydro-1-thia-3α,5-diaza-phenalene-4,6-dione (Example O-3, 0.200 g, 0.55 mmol) in DMF (3.0 mL) was reacted with pyrrolidin-3-yl-carbamic acid tert-butyl ester (0.30 g, 1.66 mmol) and triethylamine (0.38 mL, 2.75 mmol) and then heated to 50° C. overnight. The mixture was then cooled, diluted with $H_2O$, and extracted with ethyl acetate. The organic layers were combined, dried with sodium sulfate, and concentrated. The residue was purified by column chromatography (silica gel, 6:4 hexanes/ethyl acetate) to provide 0.185 g of the title compound as a solid.

EXAMPLE R-3

(1α,5α,6α)[3-(5-Benzyloxy-8-fluoro-4,6-dioxo-2,3,5,6-tetrahydro-4H-1-thia-3α,5-diaza-phenalene-9-yl)-3-aza-bicyclo[3.1.0]hex-6-yl]-carbamic acid tert-butyl ester A solution of 5-benzyloxy-8,9-difluoro-2,3-dihydro-1-thia-3α,5-diaza-phenalene-4,6-dione (Example O-3, 0.25 g, 0.69 mmol) in DMSO (3.0 mL) was reacted with 3-aza-bicyclo[3.1.0]hex-6-yl-carbamic acid tert-butyl ester (0.21 g, 1.04 mmol) and triethylamine (0.21 mL, 5.0 mmol) and then heated to 50° C. overnight. The mixture was cooled, diluted with ethyl acetate, and washed with $H_2O$ and saturated aqueous LiCl. The organic layers were combined, dried with sodium sulfate, and concentrated. The residue was purified by column chromatography (silica gel, 1:1 hexanes/ethyl acetate) to provide 0.204 g of the title compound as a solid.

EXAMPLE S-3

2,3,5-Trifluoro-4-pyrrolidin-1-yl-benzoic acid ethyl ester

A solution of 2,3,4,5-tetrafluorobenzoic acid (5.0 g, 28.7 mmol) in dichloromethane (20 mL) was reacted with oxalyl chloride (7.5 mL, 86.1 mmol) and one drop of DMF. The mixture was stirred for 30 minutes and concentrated. The residue was dissolved in dichloromethane (20 mL) and reacted with an excess of dry ethanol. After 10 minutes, $H_2O$ was added and the mixture extracted with diethyl ether. The organic layer was then dried with sodium sulfate and concentrated. The residue was taken up in acetonitrile (100 mL) and reacted with triethylamine (21.0 mL, 150 mmol) and pyrrolidine (3.2 mL, 37 mmol). The reaction was allowed to proceed overnight and was concentrated. The residue was taken up in diethyl ether and washed with saturated $NaHCO_3$. The organic layer was dried with magnesium sulfate and concentrated to provide 4.8 g of the title compound as an oil.

EXAMPLE T-3

2-Cyclopropylamino-3,5-difluoro-4-pyrrolidin-1-yl-benzoic acid

A solution of 2,3,5-trifluoro-4-pyrrolidin-1-yl-benzoic acid ethyl ester (Example S-3, 2.4 g, 8.79 mmol) in DMSO (10 mL) was reacted with cyclopropylamine (10 mL) and the mixture heated to 110° C. for 2 days in a sealed tube. The mixture was cooled and diluted with $H_2O$, acidified with citric acid, and extracted with ethyl acetate. The organic layers were combined, dried with magnesium sulfate, and concentrated to provide an oil (2.7 g). The residue was taken up in methanol (20 mL) and reacted with lithium hydroxide (1.05 g, 44.0 mmol) in $H_2O$ (20 mL) and THF (20 mL). The mixture was allowed to stir for 5 days, then acidified with citric acid. The mixture was extracted with ethyl acetate, the organic layers combined, dried with sodium sulfate, and concentrated. The residue was filtered through a plug of silica gel with chloroform to provide 1.65 g of the title compound as a solid.

EXAMPLE U-3

3-tert-Butoxy-1-cyclopropyl-6,8-difluoro-7-pyrrolidin-1-yl-1H-quinazoline-2,4-dione A solution of 2-cyclopropylamino-3,5-difluoro-4-pyrrolidin-1-yl-benzoic acid (Example T-3, 1.65 g, 5.85 mmol) in THF (20 mL) was reacted with carbonyldiimidazole (1.2 g, 7.31 mmol) and stirred overnight at ambient temperature. The mixture was reacted with triethylamine (1.22 mL, 8.77 mmol) and O-t-butyl hydroxylamine hydrochloride (1.10 g, 8.77 mmol) and allowed to stir for 4 hours. The mixture was quenched with $H_2O$ and extracted with ethyl acetate. The organic layers were combined, dried with sodium sulfate, and concentrated. The resulting residue was dissolved in THF (15 mL), reacted with carbonyldiimidazole (2.44 g, 15.0 mmol), and heated to 100° C. in a sealed tube for 5 days. The mixture was cooled, diluted with $H_2O$, and extracted with ethyl acetate. The organic layer was washed with $H_2O$, dried with sodium sulfate, and concentrated. The residue was purified by column chromatography (silica gel, 1:1 hexanes/ethyl acetate) to provide 0.52 g of the title compound as a solid.

$^1$H NMR (300 MHz, DMSO-$d_6$) δ 0.62 (bs, 1H), 0.80 (bs, 1H), 0.98 (bs, 2H), 1.24 (s, 9H), 1.87 (bs, 4H), 3.16–3.19 (m, 1H), 3.59 (bs, 4H), 7.35 (dd, 1H, J=2 Hz, J=13 Hz).

EXAMPLE V-3

2-Amino-N-benzyloxy-3,4,5,6-tetrafluoro-benzamide

Following the procedure for Example A, 2-amino-3,4,5,6-tetrafluorobenzoic acid (3.0 g, 14.4 mmol) was reacted with carbonyldiimidazole (2.8 g, 17.2 mmol), O-benzylhydroxylamine hydrochloride (3.44 g, 21.5 mmol), and triethylamine (3.0 mL, 21.5 mmol) in THF (50 mL) to provide 4.8 g of the title compound.

EXAMPLE W-3

3-Benzyloxy-5,6,7,8-tetrafluoro-1H-quinazoline-2,4-dione

A solution of 2-amino-N-benzyloxy-3,4,5,6-tetrafluoro-benzamide (Example V-3, 1.72 g, 5.47 mmol) in 1,4-dioxane (50 mL) was reacted with a 20% solution of phosgene (4.25 mL, 8.00 mmol) in toluene and heated to 80° C. in a sealed tube for 18 hours. The mixture was then cooled, diluted with ethyl acetate, and washed with saturated aqueous $NaHCO_3$. The organic layer was dried with magnesium sulfate and concentrated. The residue was triturated with diethyl ether and filtered to provide 0.95 g of the title compound as a solid.

EXAMPLE X-3

3-Benzyloxy-1-ethyl-5,6,8-trifluoro-7-pyrrolidin-1-yl-1H-quinazoline-2,4-dione

A solution of 3-benzyloxy-5,6,7,8-tetrafluoro-1H-quinazoline-2,4-dione (Example W-3, 0.90 g, 2.7 mmol), in DMA (10 mL) was reacted with pyrrolidine (0.55 mL, 6.6 mmol) and heated to 60° C. for 3 hours. The mixture was then cooled and quenched with $H_2O$ and acidified with citric acid. The mixture was then extracted with ethyl acetate, dried with $MgSO_4$, and concentrated. The residue was triturated with diethyl ether/hexanes and the solid filtered and dried (0.87 g). A portion of the solid (0.500 g, 1.28 mmol) was dissolved in DMF and reacted with ethyl iodide (1.0 mL, 12.77 mmol) and sodium hydride (0.060 g, 1.5 mmol). The mixture was stirred for 16 hours. The mixture was quenched with $H_2O$ and extracted with ethyl acetate. The organic layers were combined, dried with sodium sulfate. and concentrated. The residue was triturated with diethyl ether and filtered to yield 0.25 g of the title compound as a solid.

$^1$H NMR (300 MHz, DMSO-$d_6$) δ 1.29 (t, 3H, J=7 Hz), 1.83–1.90 (bm, 4H), 3.66 (bs, 4H), 4.00–4.10 (bm, 2H), 5.04 (s, 2H), 7.38–7.41 (m, 3H), 7.53–7.56 (m, 2H).

EXAMPLE Y-3

2-Amino-N-allyloxy-4,5-difluoro-benzamide

Carbonyldiimidazole (3.37 g, 20 mmol) was added to a suspension of 4,5-difluoroanthranilic acid (3.0 g, 17 mmol) in 80 mL of THF, and the mixture was heated to reflux for 2 hours. The solution was cooled and O-allylhydroxylamine hydrochloride (1.89 g, 17 mmol) and triethylamine (2.8 mL, 20 mmol) were added, and the mixture was heated to reflux for 17 hours. The reaction mixture was concentrated and washed with 1N HCl, saturated $NaHCO_3$, and brine and dried over magnesium sulfate. The solution was concentrated and purified by column chromatography (silica gel, $CHCl_3$/MeOH, 98:2) to give 2.08 g of the title compound as a solid.

Example Z-3

3-Allyloxy-6,7-difluoro-1H-quinazoline-2,4-dione

Phosgene, as a 12.5% solution in toluene (9.4 mL, 12 mmol), was added to a solution of 2-amino-N-allyloxy-4,5-difluorobenzamide (Example Y-3, 2.08 g, 9.1 mmol) in 75 mL of dioxane. The solution was heated at reflux for 20 hours and then poured into 200 mL of water. The aqueous solution was extracted with ethyl acetate, and the combined organic fractions were washed with water and brine and dried over magnesium sulfate. The solution was concentrated to give 2.18 g of the title compound as a solid, mp 220–221° C.

EXAMPLE A-4

3-Allyloxy-1-benzyl-6,7-difluoro-1H-quinazoline-2,4-dione

A solution of 3-allyloxy-6,7-difluoro-1H-quinazoline-2,4-dione (Example Z-3, 0.7 g, 2.8 mmol) in 20 mL of DMF was added to a suspension of sodium hydride (0.12 g, 3.0 mmol) in 15 mL of DMF and stirred for 30 minutes. Benzyl bromide (0.65 mL, 5.5 mmol) was added, and the mixture was stirred at 25° C. for 18 hours. The reaction was quenched with 1 mL of water and concentrated to an oil. The residue was dissolved in chloroform washed with water and brine and dried over magnesium sulfate. The solution was concentrated to give 1.04 g of the title compound as a solid, mp 130–132° C.

EXAMPLE B-4

3-Allyloxy-1-benzyl-6-fluoro-7-pyrrolidin-1-yl-1H-quinazoline-2,4-dione

Pyrrolidine (0.04 mL, 0.52 mmol) was added to a solution of 3-allyloxy-1-benzyl-6,7-difluoro-1H-quinazoline-2,4-dione (Example A-4, 0.15 g, 0.4 mmol) and triethylamine (0.12 mL, 0.9 mmol) in 15 mL of acetonitrile. The solution was warmed to reflux for 17 hours, cooled, and concentrated to a solid. The solid was dissolved in chloroform washed with 1N HCl, saturated $NaHCO_3$, brine, and dried over magnesium sulfate. The solution was concentrated to give 0.15 g of the title compound as a solid, mp 148–150° C.

EXAMPLE C-4

1-(3-Allyloxy-1-benzyl-6-fluoro-2,4-dioxo-1,2,3,4-tetrahydro-quinazolin-7-yl)-pyrrolidin-3-yl]-carbamic acid tert-butyl ester N-Boc-3-aminopyrrolidine (0.12 g, 0.65 mmol) was added to a solution of 3-allyloxy-1-benzyl-6,7-difluoro-1H-quinazoline-2,4-dione (Example A-4, 0.15 g, 0.4 mmol) and triethylamine (0.12 mL, 0.9 mmol) in 15 mL of acetonitrile. The solution was warmed to reflux for 17 hours, cooled, and concentrated to a solid. The solid was dissolved in chloroform washed with 1N HCl, saturated $NaHCO_3$, brine and dried over magnesium sulfate. The solution was concentrated to give 0.24 g of the title compound as a glass.

NMR ($CDCl_3$) δ 7.62 (d, 1H), 7.26 (m, 5H), 6.15 (m, 1H), 5.95 (d, 1H), 5.31 (dd, 2H), 5.22 (bs, 2H), 4.70 (d, 2H), 4.60 (bs, 1H), 4.21 (m, 1H), 3.60–3.18 (m, 4H), 2.11 (m, 1H), 1.83 (m, 1H), 1.38 (s, 9H).

EXAMPLE D-4

3-Benzyloxy-1-(2-fluoroethyl)-6,7-difluoro-1H-quinazoline-2,4-dione

A solution of 3-benzyloxy-6,7-difluoro-1H-quinazoline-2,4-dione (Example B, 1.0 g, 3.2 mmol) in 20 mL of DMF was added to a suspension of sodium hydride (0.16 g, 3.9 mmol) in 20 mL of DMF and stirred for 30 minutes. 2-Fluoroethyl iodide (1.1 g, 6.4 mmol) was added, and the mixture was warmed to 50° C. for 18 hours. The reaction was quenched with 1 mL of water and concentrated to an oil. The residue was dissolved in chloroform, washed with water, brine and dried over magnesium sulfate. The solution was concentrated to give 0.73 g of the title compound as a solid, mp 145–147° C.

EXAMPLE E-4

3-Benzyloxy-1-(2-fluoroethyl)-6-fluoro-7-pyrrolidin-1-yl-1H-quinazoline-2,4-dione Pyrrolidine (0.04 mL, 0.52 mmol) was added to a solution of 3-benzyloxy-1-(2-fluoroethyl)-6,7-difluoro-1H-quinazoline-2,4-dione (Example D-4, 0.15 g, 0.42 mmol) and triethylamine (0.36 mL, 2.6 mmol) in 20 mL of acetonitrile. The solution was warmed to reflux for 17 hours, cooled, and concentrated to a solid. The solid was dissolved in chloroform washed with 1N HCl, saturated $NaHCO_3$, brine and dried over magnesium sulfate. The solution was concentrated to give 0.14 g of the title compound as a solid.

EXAMPLE F-4

1-(3-Benzyloxy-1-(2-fluoroethyl)-6-fluoro-2,4-dioxo-1,2,3,4-tetrahydro-quinazolin-7-yl)-pyrrolidin-3-yl]-carbamic acid tert-butyl ester N-Boc-3-aminopyrrolidine (0.09 g, 0.65 mmol) was added to a solution of 3-benzyloxy-1-(2-fluoroethyl)-6,7-difluoro-1H-quinazoline-2,4-dione (Example D-4, 0.15 g, 0.4 mmol) and triethylamine (0.36 mL, 2.6 mmol) in 20 mL of acetonitrile. The solution was warmed to reflux for 41 hours, cooled, and concentrated to a solid. The solid was dissolved in chloroform washed with 1N HCl, saturated $NaHCO_3$, brine and dried over magnesium sulfate. The solution was concentrated to give 0.20 g of the title compound as a solid.

EXAMPLE G-4

3-Benzyloxy-1-(2-fluoroethyl)-6-fluoro-7-(ethyl-pyrrolidin-3-ylmethyl-amine-1-yl)-1H-quinazoline-2,4-dione Ethyl-pyrrolidin-3-ylmethyl-amine (0.06 g, 0.51 mmol) was added to a solution of 3-benzyloxy-1-(2-fluoroethyl)-6,7-difluoro-1H-quinazoline-2,4-dione (Example D-4, 0.15 g, 0.42 mmol) and triethylamine (0.36 mL, 2.6 mmol) in 20 mL of acetonitrile. The solution was warmed to reflux for 17 hours, cooled, and concentrated to a solid. The solid was dissolved in chloroform, washed with brine, and dried over magnesium sulfate. The solution was concentrated to give 0.21 g of solid, which was purified by column chromatography (silica gel, $CHCl_3$/MeOH, 80:20) to give 0.13 g of the title compound as a solid.

EXAMPLE H-4

2-(2,4-Difluoroanilino)-4,5-difluorobenzoic acid

Lithium diisopropylamide was generated at −5° C. by combining diisopropylamine (7.2 mL, 51 mmol) and n-butyl lithium (33 mL, 53 mmol) in 150 mL of dry THF. After 30 minutes, the solution was cooled to −78° C. and 2,4-difluoroaniline (3.46 mL, 34 mmol) was added and stirred for 2 hours. 2,4,5-Trifluorobenzoic acid (3.0 g, 17 mmol) was added, and the mixture was allowed to warm to room temperature over 17 hours. A saturated solution of HCl/dioxane (10 mL) was added, and after 1 hour the mixture was concentrated to a solid. The solid was redissolved in chloroform and washed with 1N HCl, water, and brine. The solution was dried and concentrated to afford 4.54 g of the title compound as a solid.

$^1H$ NMR ($CDCl_3$) δ 8.95 (bs, 1H), 7.80 (m, 2H), 7.24 (m, 1H), 6.90 (m, 2H), 6.48 (m, 1H).

EXAMPLE I-4

N-Benzyloxy-2-(2,4-difluoroanilino)-4,5-difluoro-benzamide

Carbonyldiimidazole (3.1 g, 19.1 mmol) was added to a suspension of 2-(2,4-difluoroanilino)-4,5-difluorobenzoic acid (Example H-4, 4.54 g, 15.9 mmol) in 120 mL of THF, and the mixture was stirred for 24 hours at 25° C. O-Benzylhydroxylamine hydrochloride (2.54 g, 15.9 mmol) and triethylamine (2.66 mL, 19.1 mmol) were added, and the mixture was heated to reflux for 4 hours. The reaction mixture was concentrated and washed with 1N HCl, saturated $NaHCO_3$, brine, and dried over magnesium sulfate. The solution was concentrated to give 5.66 g of the title compound as an oil.

EXAMPLE J-4

3-Benzyloxy-1-(2,4-difluorophenyl)-6,7-difluoro-1H-quinazoline-2,4-dione

N-benzyloxy-2-(2,4-difluoroanilino)-4,5-difluoro-benzamide (Example I-4, 5.66 g, 15 mmol) and carbonyl-diimidazole (2.83 g, 17 mmol) were combined in 300 mL of THF and heated to reflux for 30 hours. The solution was cooled, concentrated, and redissolved in chloroform. The solution was washed with 1N HCl, saturated $NaHCO_3$, brine, and dried over magnesium sulfate. The solution was concentrated to give 4.25 g of a solid which was purified by column chromatography (silica gel, $CHCl_3$/MeOH, 98:2) to give 2.0 g of the title compound as a solid.

EXAMPLE K-4

3-Benzyloxy-1-(2,4-difluorophenyl)-6-fluoro-7-pyrrolidin-1-yl-1H-quinazoline-2,4-dione Pyrrolidine (0.04 mL, 0.52 mmol) was added to a solution of 3-benzyloxy-1-(2,4-difluorophenyl)-6,7-difluoro-1H-quinazoline-2,4-dione (Example J-4, 0.20 g, 0.45 mmol) and triethylamine (0.34 mL, 2.4 mmol) in 20 mL of acetonitrile. The solution was warmed to reflux for 6 hours, cooled, and concentrated to a solid. The solid was dissolved in chloroform, washed with 1N HCl, saturated $NaHCO_3$, brine, and dried over magnesium sulfate. The solution was concentrated to give 0.23 g of the title compound as a solid, mp 212–214° C.

EXAMPLE L-4

1-(3-Benzyloxy-1-(2,4-difluorophenyl)-6-fluoro-2,4-dioxo-1,2,3,4-tetrahydro-quinazolin-7-yl)-pyrrolidin-3-yl]-carbamic acid tert-butyl ester N-Boc-3-aminopyrrolidine (0.11 g, 0.57 mmol) was added to a solution of 3-benzyloxy-1-(2,4-difluorophenyl)-6,7-difluoro-1H-quinazoline-2,4-dione (Example J-4, 0.2 g, 0.43 mmol) and triethylamine (0.34 mL, 2.4 mmol) in 20 mL of acetonitrile. The solution was warmed to reflux for 41 hours, cooled, and concentrated to a solid. The solid was dissolved in chloroform, washed with 1N HCl, saturated $NaHCO_3$, brine, and dried over magnesium sulfate. The solution was concentrated to give 0.27 g of the title compound as a solid.

EXAMPLE M-4

3-Benzyloxy-6,7-difluoro-1-cyclopropylmethyl-1H-quinazoline-2,4-dione

A solution of 3-benzyloxy-6,7-difluoro-1H-quinazoline-2,4-dione (Example B, 1.22 g, 4 mmol) in 25 mL of DMF was added to a suspension of sodium hydride (0.19 g, 4.8 mmol) in 20 mL of DMF and stirred for 30 minutes.

Bromomethylcyclopropane (0.6 mL, 6.0 mmol) was added, and the mixture was stirred at 25° C. for 18 hours. The reaction was quenched with 1 mL of water and concentrated to an oil. The residue was dissolved in chloroform, washed with water, brine, and dried over magnesium sulfate. The solution was concentrated to give 1.10 g of the title compound as a solid, mp 121–123° C.

EXAMPLE N-4

3-Benzyloxy-6-fluoro-1-(4-fluorophenyl)-7-pyrrolidin-1-yl-1H-pyrido[2,3-d]pyrimidine-2,4-dione Pyrrolidine (0.04 mL, 0.52 mmol) was added to a solution of 3-benzyloxy-7-chloro-6-fluoro-1-(4-fluorophenyl)-1H-pyrido[2,3-d]pyrimidine-2,4-dione (Example Q-2, 0.17 g, 0.42 mmol) and triethylamine (0.36 mL, 2.6 mmol) in 20 mL of acetonitrile. The solution was warmed to reflux for 17 hours, cooled, and concentrated to a solid. The solid was dissolved in chloroform, washed with 1N HCl, saturated $NaHCO_3$, brine, and dried over magnesium sulfate. The solution was concentrated to give 0.15 g of the title compound as a solid.

EXAMPLE O-4

3-Benzyloxy-1-butyl-6-fluoro-7-pyrrolidin-1-yl-1H-pyrido[2,3-d]pyrimidine-2,4-dione Pyrrolidine (0.04 mL, 0.52 mmol) was added to a solution of 3-benzyloxy-1-butyl-7-chloro-6-fluoro-1H-pyrido[2,3-d]pyrimidine-2,4-dione (Example O-2, 0.16 g, 0.42 mmol) and triethylamine (0.36 mL, 2.6 mmol) in 20 mL of acetonitrile. The solution was warmed to reflux for 17 hours, cooled, and concentrated to a solid. The solid was dissolved in chloroform washed with 1N HCl, saturated $NaHCO_3$, brine, and dried over magnesium sulfate. The solution was concentrated to give 0.14 g of the title compound as a solid.

EXAMPLE P-4

3-Benzyloxy-6-fluoro-7-pyrrolidin-1-yl-1-(4-trifluoromethylphenyl)-1H-pyrido[2,3-d]pyrimidine-2,4-dione Using the method of Example N-4, pyrrolidine (0.04 mL, 0.52 mmol), 3-benzyloxy-7-chloro-6-fluoro-1-(4-trifluoromethylphenyl)-1H-pyrido[2,3-d]pyrimidine-2,4-dione (Example U-2, 0.19 g, 0.42 mmol) and triethylamine (0.36 mL, 2.6 mmol) were combined in 20 mL of acetonitrile to give 0.18 g of the title compound as a solid, mp 231–233° C.

EXAMPLE Q-4

3-Benzyloxy-1-(2,4-difluorophenyl)-6-fluoro-7-pyrrolidin-1-yl-1H-pyrido[2,3-d]pyrimidine-2,4-dione Using the method of Example N-4, pyrrolidine (0.04 mL, 0.52 mmol), 3-benzyloxy-7-chloro-6-fluoro-1-(2,4-difluorophenyl)-1H-pyrido[2,3-d]pyrimidine-2,4-dione (Example S-2, 0.18 g, 0.42 mmol) and triethylamine (0.36 mL, 2.6 mmol) were combined in 20 mL of acetonitrile to give 0.15 g of the title compound as a solid, mp 183–185° C.

EXAMPLE R-4

3-Benzyloxy-6-fluoro-1-(4-methylphenyl)-7-pyrrolidin-1-yl-1H-pyrido[2,3-d]pyrimidine-2,4-dione Using the method of Example N-4, pyrrolidine (0.04 mL, 0.52 mmol), 3-benzyloxy-7-chloro-6-fluoro-1-(4-methylphenyl)-1H-pyrido[2,3-d]pyrimidine-2,4-dione (Example T-2, 0.17 g, 0.42 mmol) and triethylamine (0.36 mL, 2.6 mmol) were combined in 20 mL of acetonitrile to give 0.17 g of the title compound as a solid, mp 192–194° C.

EXAMPLE S-4

3-Benzyloxy-6-fluoro-7-pyrrolidin-1-yl-1-(3-trifluoromethylphenyl)-1H-pyrido[2,3-d]pyrimidine-2,4-dione Using the method of Example N-4, pyrrolidine (0.04 mL, 0.52 mmol), 3-benzyloxy-7-chloro-6-fluoro-1-(3-trifluoromethylphenyl)-1H-pyrido[2,3-d]pyrimidine-2,4-dione (Example V-2, 0.19 g, 0.42 mmol) and triethylamine (0.36 mL, 2.6 mmol) were combined in 20 mL of acetonitrile to give 0.16 g of the title compound as a solid, mp>250° C.

EXAMPLE T-4

3-Benzyloxy-6-fluoro-1-(2-fluorophenyl)-7-pyrrolidin-1-yl-1H-pyrido[2,3-d]pyrimidine-2,4-dione Using the method of Example N-4, pyrrolidine (0.04 mL, 0.52 mmol), 3-benzyloxy-7-chloro-6-fluoro-1-(2-fluorophenyl)-1H-pyrido[2,3-d]pyrimidine-2,4-dione (Example R-2, 0.15 g, 0.42 mmol) and triethylamine (0.36 mL, 2.6 mmol) were combined in 20 mL of acetonitrile to give 0.16 g of the title compound as a solid, mp 221–222° C.

EXAMPLE U-4

3-Benzyloxy-6-fluoro-1-(4-methoxyphenyl)-7-pyrrolidin-1-yl-1H-pyrido[2,3-d]pyrimidine-2,4-dione Using the method of Example N-4, pyrrolidine (0.04 mL, 0.52 mmol), 3-benzyloxy-7-chloro-6-fluoro-1-(4-methoxyphenyl)-1H-pyrido[2,3-d]pyrimidine-2,4-dione (Example W-2, 0.17 g, 0.42 mmol) and triethylamine (0.36 mL, 2.6 mmol) were combined in 20 mL of acetonitrile to give 0.17 g of the title compound as a solid, mp 186–188° C.

EXAMPLE V-4

3-Benzyloxy-1-cyclopropylmethyl-6-fluoro-7-pyrrolidin-1-yl-1H-quinazoline-2,4-dione Using the method of Example N-4, pyrrolidine (0.04 mL, 0.52 mmol), 3-benzyloxy-6,7-difluoro-1-methylcyclopropyl-1H-quinazoline-2,4-dione (Example M-4, 0.15 g, 0.42 mmol) and triethylamine (0.36 mL, 2.6 mmol) were combined in 20 mL of acetonitrile to give 0.16 g of the title compound as a solid, mp 198–200° C.

Example W-4

1-(3-Benzyloxy-1-cyclopropylmethyl-6-fluoro-2,4-dioxo-1,2,3,4-tetrahydro-quinazolin-7-yl)-pyrrolidin-3-yl]-carbamic acid tert-butyl ester Using the method of Example N-4, boc-3-aminopyrrolidine (0.09 g, 0.52 mmol), 3-benzyloxy-6,7-difluoro-1-methylcyclopropyl-1H-quinazoline-2,4-dione (Example M-4, 0.15 g, 0.42 mmol) and triethylamine (0.36 mL, 2.6 mmol) were combined in 20 mL of acetonitrile to give 0.17 g of the title compound as a solid.

EXAMPLE X-4

1-(3-Benzyloxy-1-(4-fluorophenyl)-6-fluoro-2,4-dioxo-1,2,3,4-tetrahydro-pyrido[2,3-d]pyrimidine-7-yl)-pyrrolidin-3-yl]-carbamic acid tert-butyl ester Using the method of Example N-4, boc-3-aminopyrrolidine (0.09 g, 0.52 mmol), 3-benzyloxy-7-chloro-6-fluoro-1-(4-fluorophenyl)-1H-pyrido[2,3-d]pyrimidine-2,4-dione (Example Q-2, 0.17 g, 0.42 mmol)) and triethylamine (0.36 mL, 2.6 mmol) were combined in 20 mL of acetonitrile to give 0.26 g of the title compound as a solid, mp 128–130° C.

EXAMPLE Y-4

(1α,5α,6α)[3-(3-Benzyloxy-1-(4-fluorophenyl)-6-fluoro-2,4-dioxo-1,2,3,4-tetrahydro-pyrido[2,3-d]pyrimidine-7-yl)-3-aza-bicyclo[3.1.0]hex-6-yl]-carbamic acid tert-butyl ester Using the method of Example N-4, 3-aza-bicyclo[3.1.0]hex-6-yl-carbamic acid tert-butyl ester (0.1 g, 0.52 mmol), 3-benzyloxy-7-chloro-6-fluoro-1-(4-fluorophenyl)-1H-pyrido[2,3-d]pyrimidine-2,4-dione (Example Q-2, 0.17 g, 0.42 mmol)) and triethylamine (0.36 mL, 2.6 mmol) were combined in 20 mL of acetonitrile to give 0.25 g of the title compound as a solid, mp 244–245° C.

EXAMPLE 1

1-Ethyl-6-fluoro-3-hydroxy-7-pyrrolidin-1-yl-1H-quinazoline-2,4-dione

Five percent Pd/$BaSO_4$ (60 mg) was added to a solution of 3-benzyloxy-1-ethyl-6-fluoro-7-pyrrolidinyl-1H-quinazoline-2,4-dione (Example E, 0.21 g, 0.55 mmol) in 16 mL of THF. The mixture was shaken under 50 PSI of hydrogen for 31 hours, filtered, and concentrated to afford 0.16 g of a solid. This solid was dissolved in 1N sodium hydroxide and washed with chloroform. The chloroform layer was back extracted with sodium hydroxide, and the combined basic extracts were acidified to pH 3. The aqueous layer was extracted with chloroform, dried over magnesium sulfate, and concentrated to give 0.11 g of the title compound as a solid, mp 170–171 ° C.

EXAMPLE 2

1-Ethyl-6-fluoro-3-hydroxy-7-(4-methyl-piperazin-1-yl)-1H-quinazoline-2,4-dione

Five percent Pd/$BaSO_4$ (110 mg) was added to a solution of 3-benzyloxy-1-ethyl-6-fluoro-7-(4-methylpiperazin-1-yl)-1H-quinazoline-2,4-dione (Example H, 0.14 g, 0.33 mmol) in 50 mL of THF. The mixture was shaken under 50 PSI of hydrogen for 60 hours, filtered, and concentrated to afford 0.1 g of the title compound as a solid, mp 132–134° C.

EXAMPLE 3

1-Ethyl-6-fluoro-3-hydroxy-7-morpholin-4-yl-1H-quinazoline-2,4-dione

Five percent Pd/$BaSO_4$ (50 mg) was added to a solution of 3-benzyloxy-1-ethyl-6-fluoro-7-morpholino-1H-quinazoline-2,4-dione (Example G, 0.23 g, 0.58 mmol) in 70 mL of THF and 5 mL methanol. The mixture was shaken under 50 PSI of hydrogen for 16 hours, filtered, and concentrated to afford 0.17 g of the title compound as a solid, mp 162–163° C.

EXAMPLE 4

1-Ethyl-6-fluoro-3-hydroxy-7-piperidin-1-yl-1H-quinazoline-2,4-dione

Piperidine (0.025 mL, 0.22 mmol) was added to a solution of 1-ethyl-6,7-difluoro-3-hydroxy-1H-quinazoline-2,4-dione (Example D, 0.05 g, 0.2 mmol) and triethylamine (0.06 mL, 0.4 mmol) in 20 mL of acetonitrile. The solution was heated to reflux for 23 hours, cooled, and concentrated to a solid. The solid was dissolved in chloroform washed with 1N HCl, water, brine, and dried over magnesium sulfate. The solution was concentrated to give 0.03 g of the title compound as a solid, mp 173–175° C.

EXAMPLE 5

1-(1-Ethyl-6-fluoro-3-hydroxy-2,4-dioxo-1,2,3,4-tetrahydro-quinazolin-7-yl)-pyrrolidin-3-yl-methyl]-carbamic acid, tert-butyl ester N-Boc-3-aminomethylpyrrolidine (0.2 g, 1.0 mmol) was added to a solution of 1-ethyl-6,7-difluoro-3-hydroxy-1H-quinazoline-2,4-dione (Example D, 0.2 g, 0.8 mmol) and triethylamine (0.23 mL, 1.7 mmol) in 20 mL of acetonitrile. The solution was heated to reflux for 23 hours, cooled, and concentrated to a solid. The solid was dissolved in chloroform washed with 1N HCl, water, brine, and dried over magnesium sulfate. The solution was concentrated to a give 0.34 g of the title compound as a solid, mp 121–124° C.

EXAMPLE 6

7-(3-Aminomethyl-pyrrolidin-1-yl)-1-ethyl-6-fluoro-3-hydroxy-1H-quinazoline-2,4-dione, hydrochloride Hydrogen chloride gas was bubbled into a solution of 1-(1-ethyl-6-fluoro-3-hydroxy-2,4-dioxo-1,2,3,4-tetrahydro-quinazolin-7-yl)-pyrrolidin-3-ylmethyl]-carbamic acid, tert-butyl ester (Example 5, 0.24 g, 0.57 mmol) in 20 mL of methylene chloride at 0° C. for 10 minutes. The solution became a suspension, and it was stirred for 24 hours. The mixture was filtered and dried to give 0.17 g of the title compound as a solid, mp 228–231 ° C.

EXAMPLE 7

1-Ethyl-6-fluoro-3-hydroxy-7-piperazin-1-yl-1H-quinazoline-2,4-dione

Piperazine (0.06 g, 0.74 mmol) was added to a solution of 1-ethyl-6,7-difluoro-3-hydroxy-1H-quinazoline-2,4-dione (Example D, 0.15 g, 0.6 mmol) and triethylamine (0.17 mL, 1.2 mmol) in 20 mL of acetonitrile. The solution was heated to reflux for 23 hours, cooled, and filtered to give 0.17 g of the title compound as a solid, mp 206–208° C.

EXAMPLE 8

1-(1-Ethyl-6-fluoro-3-hydroxy-2,4-dioxo-1,2,3,4-tetrahydro-quinazolin-7-yl)-pyrrolidin-3-methyl-3-yl-methyl]-carbamic acid, tert-butyl ester N-Boc-3-methyl-3-aminomethylpyrrolidine (0.16 g, 0.74 mmol) was added to a solution of 1-ethyl-6,7-difluoro-3-hydroxy-1H-quinazoline-2,4-dione (Example D, 0.15 g, 0.6 mmol) and triethylamine (0.17 mL, 1.2 mmol) in 20 mL of acetonitrile. The solution was heated to reflux for 23 hours, cooled, and concentrated to a solid. The solid was dissolved in chloroform, washed with 1N HCl, water, brine, and dried over magnesium sulfate. The solution was concentrated to give 0.15 g of the title compound as a solid.

NMR ($CDCl_3$): δ 8.28 (bs, 1H), 7.64 (d, 1H), 6.06 (d, 1H), 4.67 (m, 1H), 4.11 (q, 2H), 3.63 (m, 2H), 3.40 (m, 1H), 3.20 (m, 2H), 3.07 (m, 1H), 1.87 (m, 1H), 1.67 (m, 1H), 1.49 (s, 3H), 1.38 (s, 9H), 1.30 (t, 3H).

EXAMPLE 9

7-(3-Aminomethyl-3-methyl-pyrrolidin-1-yl)-1-ethyl-6-fluoro-3-hydroxy-1H-quinazoline-2,4-dione, hydrochloride Hydrogen chloride gas was bubbled into a solution of 1-(1-ethyl-6-fluoro-3-hydroxy-2,4-dioxo-1,2,3,4-tetrahydro-quinazolin-7-yl)-pyrrolidin-3-methyl-3-ylmethyl]-carbamic acid tert-butyl ester (Example 8, 0.13 g, 0.29 mmol) in 20 mL of methylene chloride at 0° C. for 10 minutes. The solution became a suspension, and it was stirred for 24 hours. The mixture was concentrated to give 0.08 g of the title compound as a foam, mp 209–211 ° C.

EXAMPLE 10

6-Fluoro-3-hydroxy-7-pyrrolidin-1-yl-1H-quinazoline-2,4-dione

Twenty percent Pd/C (50 mg) was added to a solution of 3-benzyloxy-6-fluoro-7-pyrrolidinyl-1H-quinazoline-2,4-dione (Example I, 0.21 g, 0.6 mmol) in 100 mL of THF and 100 mL of methanol. The mixture was shaken under 50 PSI of hydrogen for 4.5 hours, filtered, and concentrated to afford 0.18 g of the title compound as a solid, mp>250° C.

EXAMPLE 11

1-(6-Fluoro-3-hydroxy-1H-2,4-dioxo-1,2,3,4-tetrahydro-quinazolin-7-yl)-pyrrolidin-3-yl]-carbamic acid, tert-butyl ester Twenty percent Pd/C (50 mg) was added to a solution of 1-(3-benzyloxy-6-fluoro-1H-2,4-dioxo-1,2,3,4-tetrahydro-quinazolin-7-yl)-pyrrolidin-3-yl]-carbamic acid, tert-butyl ester (Example J, 0.22 g, 0.47 mmol) in 25 mL of THF and 25 mL of methanol. The mixture was shaken under 50 PSI of hydrogen for 1.5 hours, filtered, and concentrated to afford 0.15 g of the title compound as a solid.

EXAMPLE 12

6-Fluoro-3-hydroxy-1-methyl-7-pyrrolidin-1-yl-1H-quinazoline-2,4-dione

Pyrrolidine (0.07 mL, 0.8 mmol) was added to a solution of 6,7-difluoro-3-hydroxy-1-methyl-1H-quinazoline-2,4-dione (Example L, 0.15 g, 0.66 mmol) and triethylamine (1.2 mL, 8.6 mmol) in 30 mL of acetonitrile. The solution was warmed to reflux for 18 hours, cooled, and filtered to give a solid. The solid was triturated with chloroform, filtered, and dried to give 0.07 g of the title compound as a solid, mp>250° C.

EXAMPLE 13

7-(3-Amino-pyrrolidin-1-yl)-6-fluoro-3-hydroxy-1-methyl-1H-quinazoline-2,4-dione, Hydrochloride N-Boc-3-aminopyrrolidine (0.35 g, 1.9 mmol) was added to a solution of 6,7-difluoro-3-hydroxy-1-methyl-1H-quinazoline-2,4-dione (Example L, 0.2 g, 0.88 mmol) and triethylamine (1.7 mL, 12.1 mmol) in 30 mL of acetonitrile. The solution was warmed to reflux for 90 hours, cooled, and concentrated to a solid. The solid was dissolved in chloroform washed with 1N HCl, water, brine, and dried over magnesium sulfate. The solution was concentrated to a give 0.39 g of a solid. The solid was purified by column chromatography (chloroform/methanol 9:1). The appropriate fractions were combined to give 0.14 g of a solid, mp 164–166° C. The solid was redissolved in 20 mL of methylene chloride, and HCl gas was bubbled in at 0° C. for 10 minutes. The solution became a suspension, and it was stirred for 24 hours. The resulting precipitate was filtered and dried to give 0.1 g of the title compound as a solid, mp 220–222° C.

General Method 6. Two procedures for the deprotection of 1-(substituted phenyl)-3-benzyloxy-7-aminonucleophile-1H-quinazoline-2,4-diones Method A. Ten percent Pd/C (33% w/w) was added to a solution of 1-(substituted phenyl)-3-benzyloxy-7-aminonucleophile-1H-quinazoline-2,4-dione in 25 mL of THF and 25 mL of methanol. The mixture was stirred under atmospheric pressure of hydrogen for 1.5 hours, and filtered. The catalyst was rinsed with 200 mL of methanol and the combined organic fractions were concentrated to afford the product as a solid.

Method B. A 1 M TFA solution of $B(TFA)_3$ (3 equivalents) was added to a solution of 1-(substituted phenyl)-3-benzyloxy-7-aminonucleophile-1H-quinazoline-2,4-dione (1 equivalent) in 10 mL of TFA at 0° C. with stirring. The mixture was stirred under nitrogen at 0° C. for 10 minutes, then the cooling bath was removed, and the reaction mixture was allowed to warm to room temperature. Solvents were evaporated and the residue dissolved in methanol. The resulting solution was heated at reflux for 10 minutes, cooled to room temperature, and evaporated to dryness in vacuo. This procedure with methanol was repeated two times to afford the product as a solid.

EXAMPLE 14

1-(4-Hydroxyphenyl)-6-fluoro-3-hydroxy-7-pyrrolidin-yl-1-1H-quinazoline-2,4-dione Using the General Method 6B, the reaction of 1 M TFA solution of $B(TFA)_3$ (0.5 mL, 0.44 mmol) with 1-(4-hydroxyphenyl)-6-fluoro-3-benzyloxy-7-pyrrolidin-1-yl-1H-quinazoline-2,4-dione (Example K-1, 0.05 g, 0.11 mmol) afforded 0.038 g of the title compound as a solid, mp 264–268° C. (decomp.).

EXAMPLE 15

1-(4-Fluorophenyl)-6-fluoro-3-hydroxy-7-pyrrolidin-1-yl-1H-quinazoline-2,4-dione Using the General Method 6A, the reaction of 10% Pd/C (0.027 g) with 1-(4-fluorophenyl)-6-fluoro-3-benzyloxy-7-pyrrolidin-1-yl-1H-quinazoline-2,4-dione (Example L-1, 0.08 g, 0.18 mmol) afforded 0.05 g of the title compound as a solid, mp 183–185° C.

EXAMPLE 16

1-(4-Fluorophenyl)-6-fluoro-3-hydroxy-7-(4-methylpiperazin-1-yl)-1H-quinazoline-2,4-dione, trifluoroacetate Using the General Method 6B, the reaction of 1 M TFA solution of $B(TFA)_3$ (0.63 mL, 0.63 mmol) with 1-(4-fluorophenyl)-6-fluoro-3-benzyloxy-7-(4-methylpiperazin-1-yl)-1H-quinazoline-2,4-dione (Example M-1, 0.1 g, 0.21 mmol) afforded 0.08 g of the title compound as a solid, mp 153–154° C. (decomp.).

EXAMPLE 17

1-(4-Fluorophenyl)-6-fluoro-3-hydroxy-7-(3-aminopyrrolidin-1-yl)-1H-quinazoline-2,4-dione, hydrochloride Using the General Method 6A, the reaction of 10% Pd/C (0.075 g) with 1-(4-fluorophenyl)-6-fluoro-3-benzyloxy-7-(3-t-butoxycarbonylamino-pyrrolidin-1-yl)-1H-quinazoline-2,4-dione (Example N-1, 0.225 g, 0.4 mmol) afforded 0.182 g of 1-(4-fluorophenyl)-6-fluoro-3-hydroxy-7-(3-t-butoxycarbonylamino-pyrrolidin-1-yl)-1H-quinazoline-2,4-dione.

This material was dissolved in 20 mL of dichloromethane and a stream of HCl gas was bubbled through for 10 minutes at 0° C. The mixture was allowed to stir for an additional 24 hours when it was concentrated to give 0.131 g of the title compound as a solid, mp 197–198° C. (decomp.)

EXAMPLE 18

1-(4-Methoxyphenyl)-6-fluoro-3-hydroxy-7-pyrrolidin-1-yl-1H-quinazoline-2,4-dione Using the General Method 6A, the reaction of 10% Pd/C (0.03 g) with 1-(4-methoxyphenyl)-6-fluoro-3-benzyloxy-7-pyrrolidin-1-yl-1H-quinazoline-2,4-dione (Example O-1, 0.09 g, 0.195 mmol) afforded 0.086 g of the title compound as a solid, mp 224–226° C.

EXAMPLE 19

1-(4-Methoxyphenyl)-6-fluoro-3-hydroxy-7-(4-methylpiperazin-1-yl)-1H-quinazoline-2,4-dione Using the General Method 6A, the reaction of 10% Pd/C (0.057 g) with 1-(4-methoxyphenyl)-6-fluoro-3-benzyloxy-7-(4-methylpiperazin-1-yl)-1H-quinazoline-2,4-dione (Example P-1, 0.17 g, 0.35 mmol) afforded 0.13 g of the title compound as a solid, mp 195–196° C.

EXAMPLE 20

1-(4-Methoxyphenyl)-6-fluoro-3-hydroxy-7-(3-aminopyrrolidin-1-yl)-1H-quinazoline-2,4-dione, hydrochloride Using the General Method 6A, the reaction of 10% Pd/C (0.074 g) with 1-(4-methoxy phenyl)-6-fluoro-3-benzyloxy-7-(3-t-butoxycarbonylamino-pyrrolidin-1-yl)-1H-quinazoline-2,4-dione (Example Q-1, 0.222 g, 0.38 mmol) afforded 0.185 g of 1-(4-methoxyphenyl)-6-fluoro-3-hydroxy-7-(3-t-butoxycarbonylamino-pyrrolidin-1-yl)-1H-quinazoline-2,4-dione as a solid.

This material was dissolved in 20 mL of dichloromethane, and a stream of HCl gas was bubbled through for 10 minutes at 0° C. The mixture was allowed to stir for an additional 24 hours, when it was concentrated to give 0.136 g of the title compound as a solid, mp 209–210° C. (decomp.).

EXAMPLE 21

1-(3-Chloro-4-fluorophenyl)-6-fluoro-3-hydroxy-7-(4-methylpiperazin-1-yl)-1H-quinazoline-2,4-dione Using the General Method 6A, the reaction of 10% Pd/C (0.06 g) with 1-(3-chloro-4-fluorophenyl)-6-fluoro-3-benzyloxy-7-(4-methylpiperazin-1-yl)-1H-quinazoline-2,4-dione (Example R-1, 0.12 g, 0.23 mmol) afforded 0.085 g of the title compound as a solid, mp 197–199° C.

EXAMPLE 22

1-(3-Chloro-4-fluorophenyl)-6-fluoro-3-hydroxy-7-(3-aminopyrrolidin-1-yl)-1H-quinazoline-2,4-dione, trifluoroacetate Using the General Method 6B, the reaction of 1 M TFA solution of $B(TFA)_3$ (1.0 mL, 1.0 mmol) with 1-(3-chloro-4-fluoro-phenyl)-6-fluoro-3-benzyloxy-7-(3-t-butoxycarbonylamino-pyrrolidin-1-yl)-1H-quinazoline-2,4-dione (Example S-1, 0.19 g, 0.37 mmol) afforded 0.06 g of the title compound as a solid, mp 229–231 ° C.

EXAMPLE 23

1-(3-Methoxyphenyl)-6-fluoro-3-hydroxy-7-pyrrolidin-1-yl-1H-quinazoline-2,4-dione Using the General Method 6A, the reaction of 10% Pd/C (0.04 g) with 1-(3-methoxyphenyl)-6-fluoro-3-benzyloxy-7-pyrrolidin-1-yl-1H-quinazoline-2,4-dione (Example T-1, 0.12 g, 0.26 mmol) afforded 0.09 g of the title compound as a solid, mp 216–218° C.

EXAMPLE 24

1-(3-Methoxyphenyl)-6-fluoro-3-hydroxy-7-(4-methylpiperazin-1-yl)-1H-quinazoline-2,4-dione Using the General Method 6A, the reaction of 10% Pd/C (0.04 g) with 1-(3-methoxyphenyl)-6-fluoro-3-benzyloxy-7-(4-methylpiperazin-1-yl)-1H-quinazoline-2,4-dione (Example U-1, 0.12 g, 0.24 mmol) afforded 0.08 g of the title compound as a solid, mp 158–160° C.

EXAMPLE 25

1-(3-Methoxyphenyl)-6-fluoro-3-hydroxy-7-(3-aminopyrrolidin-1-yl)-1H-quinazoline-2,4-dione, hydrochloride Using the General Method 6A, the reaction of 10% Pd/C (0.05 g) with 1-(3-methoxyphenyl)-6-fluoro-3-benzyloxy-7-(3-t-butoxycarbonylamino-pyrrolidin-1-yl)-1H-quinazoline-2,4-dione (Example V-1, 0.15 g, 0.26 mmol) afforded 0.12 g of 1-(3-methoxyphenyl)-6-fluoro-3-hydroxy-7-(3-t-butoxycarbonylamino-pyrrolidin-1-yl)-1H-quinazoline-2,4-dione as a solid.

This material was dissolved in 20 mL of dichloromethane, and a stream of HCl gas was bubbled through for 10 minutes at 0° C. The mixture was allowed to stir for an additional 24 hours, when it was concentrated to give 0.10 g of the title compound as a solid, mp 215–217° C. (decomp.).

EXAMPLE 26

1-(2-Fluorophenyl)-6-fluoro-3-hydroxy-7-pyrrolidin-1-yl-1H-quinazoline-2,4-dione Using the General Method 6A, the reaction of 10% Pd/C (0.03 g) with 1-(2-fluorophenyl)-6-fluoro-3-benzyloxy-7-pyrrolidin-1-yl-1H-quinazoline-2,4-dione (Example W-1, 0.1 g, 0.22 mmol) provided 0.07 g of the title compound as a solid, mp 235–237° C.

EXAMPLE 27

1-(2-Fluorophenyl)-6-fluoro-3-hydroxy-7-(4-methylpiperazin-1-yl)-1H-quinazoline-2,4-dione Using the General Method 6A, the reaction of 10% Pd/C (0.03 g) with 1-(2-fluorophenylamino)-6-fluoro-3-benzyloxy-(4-methylpiperazin-1-yl)-1H-quinazoline-2,4-dione (Example X-1, 0.09 g, 0.18 mmol) provided 0.07 g of the title compound as a solid, mp 160–162° C.

EXAMPLE 28

1-(3-Fluorophenyl)-6-fluoro-3-hydroxy-7-pyrrolidin-1-yl-1H-quinazoline-2,4-dione Using the General Method 6A, the reaction of 10% Pd/C (0.03 g) with 1-(3-fluorophenyl)-6-fluoro-3-benzyloxy-7-pyrrolidin-1-yl-1H-quinazoline-2,4-dione (Example Y-1, 0.1 g, 0.22 mmol) provided 0.09 g of the title compound as a solid, mp 239–241° C.

EXAMPLE 29

1-(3-Fluorophenyl)-6-fluoro-3-hydroxy-7-(4-methylpiperazin-1-yl)-1H-quinazoline-2,4-dione Using the General Method 6A, the reaction of 10% Pd/C (0.07 g) with 1-(3-fluorophenyl)-6-fluoro-3-benzyloxy-7-(4-methylpiperazin-1-yl)-1H-quinazoline-2,4-dione (Example Z-1, 0.209 g, 0.43 mmol) provided 0.11 g of the title compound as a solid, mp 176–178° C.

EXAMPLE 30

1-(3-Fluorophenyl)-6-fluoro-3-hydroxy-7-(3-aminopyrrolidin-1-yl)-1H-quinazoline-2,4-dione, trifluoroacetate Using the General Method 6B, the reaction of 1 M TFA solution of $B(TFA)_3$ (1.3 mL, 1.3 mmol) with 1-(3-fluorophenyl)-6-fluoro-3-benzyloxy-7-(3-t-butoxycarbonylamino-pyrrolidin-1-yl)-1H-quinazoline-2,4-dione (Example A-2, 0.231 g, 0.41 mmol) afforded 0.11 g of the title compound as a solid, mp 214–216° C.

EXAMPLE 31

1-(2,4,5-Trifluoroethyl)-6-fluoro-3-hydroxy-7-(3-aminopyrrolidin-1-yl)-1H-quinazoline-2,4-dione, trifluoroacetate Using the General Method 6B, the reaction of 1 M TFA solution of $B(TFA)_3$ (0.6 mL, 0.6 mmol) with 1-(2,4,5-trifluoro-phenyl)-6-fluoro-3-benzyloxy-7-(3-t-butoxycarbonylamino-pyrrolidin-1-yl)-1H-quinazoline-2,4-dione (Example B-2, 0.13 g, 0.2 mmol) afforded 0.063 g of the title compound as a solid, mp 240–242° C. (decomp.).

EXAMPLE 32

1-Cyclopropyl-6-fluoro-3-hydroxy-7-pyrrolidin-1-yl-1H-pyrido[2,3-d]pyrimidine-2,4-dione A suspension of 3-benzyloxy-1-cyclopropyl-6-fluoro-7-pyrrolidin-1-yl-1H-pyrido[2,3-d]pyrimidine-2,4-dione (Example K-2, 60 mg, 0.152 mmol) and 10% Pd/C (30 mg)

in MeOH (3 mL) was stirred at room temperature in hydrogen atmosphere provided by a balloon for 30 minutes. Filtration and concentration of the filtrate gave a solid residue, which was further washed with 10% of dichloromethane/hexane to give 40 mg of the title compound as powder, mp 238° C. (decomp.).

EXAMPLE 33

1-Cyclopropyl-6-fluoro-3-hydroxy-7-(4-methylpiperazin-1-yl)-1H-pyrido[2,3-d]pyrimidine-2,4-dione, hydrochloride Following the procedure of Example 32, the reaction of 3-benzyloxy-1-cyclopropyl-6-fluoro-7-(4-methylpiperazin-1-yl)-1H-pyrido[2,3-d]pyrimidine-2,4-dione (Example L-2, 65 mg, 0.157 mmol), 10% Pd/C (30 mg) in MeOH (3 mL) under a hydrogen atmosphere, followed by adding a few drop of acetyl chloride into the reaction mixture provided 45 mg of the title compound as powder, mp>300° C. (decomp.).

EXAMPLE 34

1-Ethyl-6-fluoro-3-hydroxy-7-pyrrolidin-1-yl-1H-pyrido[2,3-d]pyrimidine-2,4-dione Following the procedure of Example 32, hydrogenation of 3-benzyloxy-1-ethyl-6-fluoro-7-pyrrolidin-1-yl-1H-pyrido[2,3-d]pyrimidine-2,4-dione (Example X-2, 110 mg, 0.286 mmol) and 10% Pd/C (60 mg) in MeOH (2 mL) and ethyl acetate (3 mL) afforded 55 mg, of the title compound as a solid, mp 236–237° C. (decomp.).

EXAMPLE 35

1-Ethyl-6-fluoro-3-hydroxy-7-(4-methylpiperazin-1-yl)-1H-pyrido[2,3-d]pyrimidine-2,4-dione Following the procedure of Example 32, hydrogenation of 3-benzyloxy-1-ethyl-6-fluoro-7-(4-methylpiperazin-1-yl)-1H-pyrido[2,3-d]pyrimidine-2,4-dione (Example Y-2, 187 mg, 0.450 mmol) and 10% Pd/C (35 mg) in MeOH (5 mL) afforded 105 mg of the title compound as a solid, mp 219–220° C. (decomp.).

EXAMPLE 36

7-(3-Aminopyrrolidin-1-yl)-1-ethyl-6-fluoro-3-hydroxy-1H-pyrido[2,3-d]pyrimidine-2,4-dione, trifluoroacetate To a solution of 3-benzyloxy-1-ethyl-6-fluoro-7-[3-(N-tert-butoxycarbonylamino)-pyrrolidin-1-yl]-1H-pyrido[2,3-d]pyrimidine-2,4-dione (Example Z-2, 230 mg, 0.46 mmol) in trifluoroacetic acid (TFA) (3 mL) was added 1 M $B(TFA)_3$ in TFA (1.4 mL, 1.4 mmol) at 0° C., and stirring was continued at room temperature for 30 minutes. The mixture was evaporated under reduced pressure, and the residue was dissolved in MeOH (3 mL), refluxed for 1 hour and concentrated into 1 mL. White powder precipitated, when the methanolic solution was diluted with dichloromethane (5 mL) and cooled in an ice-water bath. Filtration and drying in vacuo provided the title compound (150 mg, 77%) as solid, mp 258° C.

EXAMPLE 37

1-Benzyl-6-fluoro-3-hydroxy-7-pyrrolidin-1-yl-1H-pyrido[2,3-d]pyrimidine-2,4-dione Following the procedure of Example 32, hydrogenation of 1-benzyl-3-benzyloxy-6-fluoro-7-pyrrolidin-1-yl-1H-pyrido[2,3-d]pyrimidine-2,4-dione (Example A-3, 110 mg, 0.247 mmol) and 10% Pd/C (15 mg) in MeOH (2 mL) and ethyl acetate (3 mL) afforded 67 mg, of the title compound as a solid, mp 219–220° C.

EXAMPLE 38

1-Cyclopropyl-6-fluoro-3-hydroxy-7-(pyrrolidin-1-yl)-1H-quinazoline-2,4-dione

A solution of 3-benzyloxy-1-cyclopropyl-6-fluoro-7-pyrrolidin-1-yl-1H-quinazoline-2,4-dione (Example F-3, 0.15 g, 0.38 mmol) in trifluoroacetic acid (TFA, 3.0 mL) was reacted with a 1.0 M solution of boron tris(trifluoroacetate) (1.5 mL, 1.5 mmol, *Angew. Chem, Internat. Ed.*, 1973;12:147) in TFA and allowed to stir for 2 hours. The mixture was then concentrated and the residue diluted in methanol and concentrated. This process was repeated two times. The residue was then triturated from diethyl ether/hexanes and filtered to provide 0.073 g of the title compound as solid, mp 248–250° C. (dec.).

EXAMPLE 39

7-(3-Amino-pyrrolidin-1-yl)-1-cyclopropyl-6-fluoro-3-hydroxy-1H-quinazoline-2,4-dione A solution of [1-(3-benzyloxy-1-cyclopropyl-6-fluoro-2,4-dioxo-1,2,3,4-tetrahydro-quinazolin-7-yl)-pyrrolidin-3-yl]-carbamic acid tert-butyl ester (Example G-3, 0.10 g, 0.22 mmol) in trifluoroacetic acid (TFA, 3.0 mL) was reacted with a 1.0 M solution of boron tris(trifluoroacetate) (1.1 mL, 1.1 mmol) in TFA and allowed to stir for 3 hours. The mixture was then concentrated and the residue rediluted in methanol and concentrated. This process was repeated two times. The residue was then triturated from diethyl ether and filtered to provide 0.075 g of the title compound as a solid, mp 244–245° C. (dec.).

EXAMPLE 40

7-(3-Aminomethyl-pyrrolidin-1-yl)-1-cyclopropyl-6-fluoro-3-hydroxy-1H-quinazoline-2,4-dione, trifluoroacetate A solution of [1-(3-benzyloxy-1-cyclopropyl-6-fluoro-2,4-dioxo-1,2,3,4-tetrahydro-quinazolin-7-yl)-pyrrolidin-3-ylmethyl]-carbamic acid tert-butyl ester (Example H-3, 0.127 g, 0.24 mmol) in trifluoroacetic acid (TFA, 3.0 mL) was reacted with a 1.0 M solution of boron tris(trifluoroacetate) (1.5 mL, 1.5 mmol) in TFA and allowed to stir for 3 hours. The mixture was then concentrated and the residue rediluted in methanol and concentrated again. This process was repeated three times. The residue was then triturated from diethyl ether and filtered to provide 0.095 g of the title compound as a solid, mp 146–148° C.

EXAMPLE 41

7-(3-Amino-azetidin-1-yl)-1-cyclopropyl-6-fluoro-3-hydroxy-1H-quinazoline-2,4-dione, trifluoroacetate A solution of [1-(3-benzyloxy-1-cyclopropyl-6-fluoro-2,4-dioxo-1,2,3,4-tetra-hydro-quinazolin-7-yl)-azetidin-3-yl]-carbamic acid tert-butyl ester (Example I-3, 0.13 g, 0.26 mmol) in trifluoroacetic acid (TFA, 3.0 mL) was reacted with a 1.0 M solution of boron tris(trifluoroacetate) (2.0 mL, 1.0 mmol) in TFA and allowed to stir for 2 hours. The mixture was then concentrated and the residue diluted in methanol and concentrated again. This process was repeated three times. The residue was then triturated from diethyl ether and filtered to provide 0.097 g of the title compound as a solid, mp 214–216° C. (dec.).

EXAMPLE 42

(1α, 5α, 6α)7-(6-Amino-3-aza-bicyclo[3.1.0]hex-3-yl)-1-cyclopropyl-6-fluoro-3-hydroxy-1H-quinazoline-2,4-dione, trifluoroacetate A solution of (1α, 5α, 6α)[3-(3-benzyloxy-1-cyclopropyl-6-fluoro-2,4-dioxo-1,2,3,4-tetrahydro-quinazolin-7-yl)-3-aza-bicyclo[3.1.0]hex-6-yl]-carbamic acid tert-butyl ester (Example J-3, 0.19 g, 0.36 mmol) in trifluoroacetic acid (TFA, 4.0 pmL) was reacted with a 1.0 M solution of boron tris(trifluoroacetate) (1.8 mL, 1.8 mmol) in TFA and allowed to stir for 2 hours. The mixture was concentrated and the residue dissolved in methanol and concentrated again. This process was repeated three times. The residue was triturated from diethyl ether and filtered to provide 0.134 g of the title compound as a solid, mp 200–201° C. (dec.).

EXAMPLE 43

(4αS-cis) 1-Cyclopropyl-6-fluoro-3-hydroxy-7-(octahydro-pyrrolo[3,4-b]pyridin-6-yl)-1H-quinazoline-2,4-dione, trifluoroacetate A solution of (4aR-(4aα7aα)6-(3-benzyloxy-1-cyclopropyl-6-fluoro-2,4-dioxo-1,2,3,4-tetrahydro-quinazolin-7-yl)-octahydro-pyrrolo[3,4-b]pyridine-1-carboxylic acid tert-butyl ester (Example K-3, 0.215 g, 0.39 mmol) in trifluoroacetic acid (TFA, 4.0 mL) was reacted with a 1.0 M solution of boron tris(trifluoroacetate) (2.0 mL, 2.0 mmol) in TFA and allowed to stir for 2 hours. The mixture was concentrated and the residue dissolved in methanol and concentrated again. This process was repeated three times. The residue was triturated from diethyl ether and filtered to provide 0.16 g of the title compound as a solid, mp 190–192° C. (dec.).

EXAMPLE 44

8-Fluoro-5-hydroxy-9-pyrrolidin-1-yl-2,3-dihydro-1-thia-3α,5-diaza-phenalene-4,6-dione A solution of 5-benzyloxy-8-fluoro-9-pyrrolidin-1-yl-2,3-dihydro-1-thia-3α,5-diaza-phenalene-4,6-dione (Example P-3, 0.120 g, 0.29 mmol) in trifluoroacetic acid (3.0 mL) was reacted with a 1.0 M solution of boron tris(trifluoroacetate) (1.74 mL, 1.74 mmol) in TFA and allowed to stir for 3 hours. The mixture was concentrated and the residue dissolved in methanol and concentrated again. This process was repeated three times. The residue was triturated from diethyl ether and filtered to provide the 0.084 g of the title compound as a solid, mp 182–184° C.

EXAMPLE 45

9-(3-Amino-pyrrolidin-1-yl)-8-fluoro-5-hydroxy-2,3-dihydro-1-thia-3α,5-diaza-phenalene-4,6-dione, trifluoroacetate A solution of [1-(5-benzyloxy-8-fluoro-4,6-dioxo-2,3,5,6-tetrahydro-4H-1-thia-3α,5-diaza-phenalene-9-yl)-pyrrolidin-3-yl]-carbamic acid tert-butyl ester (Example Q-3, 0.187 g, 0.353 mmol) in trifluoroacetic acid (3.0 mL) was reacted with a 1.0 M solution of boron tris (trifluoroacetate) (2.12 mL, 2.12 mmol) in TFA and allowed to stir for 2 hours. The mixture was concentrated and the residue dissolved in methanol and concentrated again. This process was repeated three times. The residue was triturated from diethyl ether and filtered to provide 0.154 g of the title compound as a solid, mp 232–234° C.

EXAMPLE 46

(1α,5α,6α)9-(6-Amino-3-aza-bicyclo[3.1.0]hex-3-yl)-8-fluoro-5-hydroxy-2,3-dihydro-1-thia-3α,5-diaza-phenalene-4,6-dione, trifluoroacetate A solution of (1α,5α,6α)[3-(5-benzyloxy-8-fluoro-4,6-dioxo-2,3,5,6-tetrahydro-4H-1-thia-3α,5-diaza-phenalene-9-yl)-3-aza-bicyclo[3.1.0]hex-6-yl]-carbamic acid tert-butyl ester (Example R-3, 0.200 g, 0.38 mmol) in trifluoroacetic acid (3.0 mL) was reacted with a 1.0 M solution of boron tris(trifluoroacetate) (1.92 mL, 1.92 mmol) in TFA and allowed to stir for 2 hours. The mixture was concentrated and the residue dissolved in methanol and concentrated again. This process was repeated three times. The residue was triturated from diethyl ether and filtered to provide 0.17 g of the title compound as a solid, mp 185–187° C.

EXAMPLE 47

1-Cyclopropyl-6,8-difluoro-3-hydroxy-7-pyrrolidin-1-yl-1H-quinazoline-2,4-dione

A solution of 3-tert-butoxy-1-cyclopropyl-6,8-difluoro-7-pyrrolidin-1-yl-1H-quinazoline-2,4-dione (Example U-3, 0.52 g) in TFA (10 mL) was allowed to stir overnight at ambient temperature. The mixture was then concentrated and the product triturated with diethyl ether (repeated three times). The solid was filtered and washed with diethyl ether and dried to provide 0.35 g of the title compound as a solid, mp 228–230° C.

EXAMPLE 48

1-Ethyl-5,6,8-trifluoro-3-hydroxy-7-pyrrolidin-1-yl-1H-quinazoline-2,4-dione

A solution of 3-benzyloxy-1-ethyl-5,6,8-trifluoro-7-pyrrolidin-1-yl-1H-quinazoline-2,4-dione (Example X-3, 0.15 g, 0.36 mmol) in trifluoroacetic acid (5.0 mL) was reacted with a 1.0 M solution of boron tris(trifluoroacetate) (1.8 mL, 1.8 mmol) in TFA and allowed to stir for 1 hour. The mixture was then concentrated and the residue dissolved in methanol and concentrated. This process was repeated three times. The residue was then triturated from diethyl ether and filtered to provide 0.11 g of the title compound as a solid, mp 223–225° C.

EXAMPLE 49

1-Benzyl-6-fluoro-3-hydroxy-7-pyrrolidin-1-yl-1H-quinazoline-2,4-dione

Phenylsilane (0.07 mL, 0.56 mmol) and palladium tetrakistriphenylphosphine (17 mg, 0.015 mmol) were added to a solution of 3-allyloxy-1-benzyl-6-fluoro-7-pyrrolidin-1-yl-1H-quinazoline-2,4-dione (Example B-4, 0.15 g, 0.4 mmol) in 10 mL of dichloromethane at 0° C. The mixture was stirred for 17 hours and filtered to give 0.06 g of the title compound as a solid, mp 234–236° C.

EXAMPLE 50

1-Benzyl-6-fluoro-3-hydroxy-7-(3-amino-pyrrolidin-1-yl)-1H-quinazoline-2,4-dione Phenylsilane (0.09 mL, 0.71 mmol) and palladium tetrakistriphenylphosphine (21 mg, 0.019 mmol) were added to a solution of 1-(3-allyloxy-1-benzyl-6-fluoro-2,4-dioxo-1,2,3,4-tetrahydro-quinazolin-7-yl)-pyrrolidin-3-yl]-carbamic acid tert-butyl ester (Example C-4, 0.24 g, 0.4 mmol) in 3 mL of dichloromethane at 0° C. The mixture was stirred for 17 hours and filtered to give 0.08 g of a solid. The filtrate was purified by column chromatography (silica gel, $CHCl_3$/MeOH, 80:20) to give an additional 0.06 g. The solids were combined to give 0.14 g 1-benzyl-6-fluoro-3-hydroxy-2,4-dioxo-1,2,3,4-tetrahydro-quinazolin-7-yl)-pyrrolidin-3-yl]-carbamic acid tert-butyl ester as a solid. This material was dissolved in 20 mL of dichloromethane at 0° C. and a stream of HCl was bubbled in for 10 minutes. The solution became a suspension and it was stirred for 24 hours. The mixture was filtered and dried to give 0.08 g of the title compound as a solid.

EXAMPLE 51

1-(2-Fluoroethyl)-6-fluoro-3-hydroxy-7-pyrrolidin-1-yl-1H-quinazoline-2,4-dione

Twenty percent Pd/C (25 mg) was added to a solution of 3-benzyloxy-1-(2-fluoroethyl)-6-fluoro-7-pyrrolidin-1-yl- 1H-quinazoline-2,4-dione (Example E-4, 0.17 g, 0.4 mmol) in 50 mL of THF, this was shaken under 50 PSI of hydrogen for 14.5 hours. The mixture was filtered and concentrated to afford 0.16 g of a solid, which was triturated with ether and dried to give 0.07 g of the title compound as a solid, mp 228–230° C.

EXAMPLE 52

1-(2-Fluoroethyl)-6-fluoro-3-hydroxy-2,4-dioxo-1,2,3,4-tetrahydro-quinazolin-7-yl)-pyrrolidin-3-yl]-carbamic acid tert-butyl ester Twenty percent Pd/C (25 mg) was added to a solution of 1-(3-benzyloxy-1-(2-fluoroethyl)-6-fluoro-2,4-dioxo-1,2,3,4-tetrahydro-quinazolin-7-yl)-pyrrolidin-3-yl]-carbamic acid tert-butyl ester (Example F-4, 0.20 g, 0.38 mmol) in 50 mL of THF. This was shaken under 50 PSI of hydrogen for 6.3 hours. The mixture was filtered and concentrated to afford 0.16 g of the title compound.

EXAMPLE 53

1-(2-Fluoroethyl)-6-fluoro-3-hydroxy-7-(ethyl-pyrrolidin-3-ylmethyl-amine-1-yl)-1H-quinazoline-2,4-dione Twenty percent Pd/C (25 mg) was added to a solution of 3-benzyloxy-1-(2-fluoroethyl)-6-fluoro-7-(ethyl-pyrrolidin-3-ylmethyl-amine -1-yl)-1H-quinazoline-2,4-dione (Example G-4, 0.15 g, 0.33 mmol) in 16 mL of THF; this was shaken under 50 PSI of hydrogen for 14.5 hours. The mixture was filtered and concentrated, and the solid formed was triturated with ether and dried to give 0.07 g of the title compound as a solid.

EXAMPLE 54

1-(2,4-Difluorophenyl)-6-fluoro-3-hydroxy-7-pyrrolidin-1-yl-1H-quinazoline-2,4-dione Twenty percent Pd/C (50 mg) was added to a solution of 3-benzyloxy-1-(2,4-difluorophenyl)-6-fluoro-7-pyrrolidin-1-yl-1H-quinazoline-2,4-dione (Example K-4, 0.22 g, 0.5 mmol) in 40 mL of THF, and this was shaken under 50 PSI of hydrogen for 16 hours. The mixture was filtered and concentrated to afford 0.19 g of a solid. This solid was triturated with ether and filtered to give 0.08 g of the title compound as a solid, mp 232–234° C.

EXAMPLE 55

1-(2,4-Difluorophenyl)-6-fluoro-3-hydroxy-7-(3-amino-pyrrolidin-1-yl)-1H-quinazoline-2,4-dione, hydrochloride Twenty percent Pd/C (50 mg) was added to a solution of 1-(3-benzyloxy-1-(2,4-difluorophenyl)-6-fluoro-2,4-dioxo-1,2,3,4-tetrahydro-quinazolin-7-yl)-pyrrolidin-3-yl]-carbamic acid tert-butyl ester (Example L-4, 0.23 g, 0.4 mmol) in 16 mL of THF, and this was shaken under 50 PSI of hydrogen for 2.5 hours. The mixture was filtered and concentrated to give 0.22 g of 1-(2,4-difluorophenyl)-6-fluoro-3-hydroxy-2,4-dioxo-1,2,3,4-tetrahydro-quinazolin-7-yl)-pyrrolidin-3-yl]-carbamic acid tert-butyl ester. This material was dissolved in 10 mL of dichloromethane and reacted with a stream of HCl gas at 0° C. for 10 minutes. The solution became a suspension and it was stirred for 17 hours. The mixture was filtered and dried to give 0.12 g of the title compound as a solid, mp>250° C.

EXAMPLE 56

6-Fluoro-1-(4-fluorophenyl)-3-hydroxy-7-pyrrolidin-1-yl-1H-pyrido[2,3-d]pyrimidine-2,4-dione Twenty percent Pd/C (70 mg) was added to a solution of 3-benzyloxy-6-fluoro-1-(4-fluorophenyl)-7-pyrrolidin-1-yl-1H-pyrido[2,3-d]pyrimidine-2,4-dione (Example N-4, 0.15 g, 0.33 mmol) in 25 mL of THF, and this was shaken under 50 PSI of hydrogen for 17.5 hours. The mixture was filtered and concentrated to give 0.13 g of the title compound as a solid, mp 172–174° C.

EXAMPLE 57

1-Butyl-6-fluoro-3-hydroxy-7-pyrrolidin-1-yl-1H-pyrido[2,3-d]pyrimidine-2,4-dione Twenty percent Pd/C (70 mg) was added to a solution of 3-benzyloxy-1-butyl-6-fluoro-7-pyrrolidin-1-yl-1H-pyrido[2,3-d]pyrimidine-2,4-dione (Example O-4, 0.13 g, 0.32 mmol) in 25 mL of THF, and this was shaken under 50 PSI of hydrogen for 17.5 hours. The mixture was filtered and concentrated to give 0.11 g of the title compound as a solid, mp 153–155° C.

EXAMPLE 58

6-Fluoro-3-hydroxy-7-pyrrolidin-1-yl-1-(4-trifluoromethylphenyl-1H-pyrido[2,3-d]pyrimidine-2,4-dione Using the method of Example 56, 20% Pd/C (30 mg), 3-benzyloxy-6-fluoro-7-pyrrolidin-1-yl-1-(4-trifluoromethylphenyl)-1H-pyrido[2,3-d]pyrimidine-2,4-dione (Example P-4, 0.17 g, 0.34 mmol) were combined in 50 mL of THF, to give 0.14 g of the title compound as a solid, mp 203–205° C.

EXAMPLE 59

1-(2,4-Difluorophenyl)-6-fluoro-3-hydroxy-7-pyrrolidin-1-yl-1H-pyrido[2,3-d]pyrimidine-2,4-dione Using the method of Example 56, 20% Pd/C (40 mg), 3-benzyloxy-1-(2,4-difluorophenyl)-6-fluoro-7-pyrrolidin-1-yl-1H-pyrido[2,3-d]pyrimidine-2,4-dione (Example Q-4, 0.15 g, 0.33 mmol) were combined in 50 mL of THF, to give 0.06 g of the title compound as a solid, mp 189–191° C.

EXAMPLE 60

6-Fluoro-3-hydroxy-1-(4-methylphenyl)-7-pyrrolidin-1-yl-1H-pyrido[2,3-d]pyrimidine-2,4-dione Using the method of Example 56, 20% Pd/C (20 mg), 3-benzyloxy-6-fluoro-1-(4-methylphenyl)-7-pyrrolidin-1-yl-1H-pyrido[2,3-d]pyrimidine-2,4-dione (Example R-4, 0.16 g, 0.33 mmol) were combined in 25 mL of THF, to give 0.11 g of the title compound as a solid, mp 228–230° C.

EXAMPLE 61

6-Fluoro-3-hydroxy-7-pyrrolidin-1-yl-1-(3-trifluoromethylphenyl)-1H-pyrido[2,3-d]pyrimidine-2,4-dione Using the method of Example 56, 20% Pd/C (25 mg), 3-benzyloxy-6-fluoro-7-pyrrolidin-1-yl-1-(3-trifluoromethylphenyl)-1H-pyrido[2,3-d]pyrimidine-2,4-dione (Example S-4, 0.17 g, 0.34 mmol) were combined in 25 mL of THF, to give 0.08 g of the title compound as a solid, mp 136–138° C.

EXAMPLE 62

1-(2-Fluorophenyl)-6-fluoro-3-hydroxy-7-pyrrolidin-1-yl-1H-pyrido[2,3-d]pyrimidine-2,4-dione Using the method of Example 56, 20% Pd/C (25 mg), 3-benzyloxy-1-(2-fluorophenyl)-6-fluoro-7-pyrrolidin-1-yl-1H-pyrido[2,3-d]pyrimidine-2,4-dione (Example T-4, 0.14 g, 0.31 mmol) were combined in 25 mL of THF, to give 0.13 g of the title compound as a solid, mp>250° C.

EXAMPLE 63

6-Fluoro-3-hydroxy-1-(4-methoxyphenyl)-7-pyrrolidin-1-yl-1H-pyrido[2,3-d]pyrimidine-2,4-dione Using the method of Example 56, 20% Pd/C (20 mg), 3-benzyloxy-6-fluoro-1-(4-methoxyphenyl)-7-pyrrolidin-1- yl-1H-pyrido[2,3-d]pyrimidine-2,4-dione (Example U-4, 0.16 g, 0.34 mmol) were combined in 15 mL of THF, to give 0.11 g of the title compound as a solid.

EXAMPLE 64

1-Cyclopropylmethyl-6-fluoro-3-hydroxy-7-pyrrolidin-1-yl-1H-quinazoline-2,4-dione Using the method of Example 56, 20% Pd/C (25 mg), 3-benzyloxy-1-cyclopropylmethyl-6-fluoro-7-pyrrolidin-1-yl-1H-quinazoline-2,4-dione (Example V-4, 0.16 g, 0.39 mmol) were combined in 25 mL of THF, to give 0.06 g of the title compound as a solid, mp 211–213° C.

EXAMPLE 65

1-(4-Fluorophenyl)-6-fluoro-3-hydroxy-7-(3-amino-pyrrolidin-1-yl)-1H-pyrido[2,3-d]pyrimidine-2,4-dione, hydrochloride Using the method of Example 55, 20% Pd/C (30 mg), and 1-(3-benzyloxy-1-(4-fluorophenyl)-6-fluoro-2,4-dioxo-1,2,3,4-tetrahydropyrido[2,3-d]pyrimidine-7-yl)-pyrrolidin-3-yl]-carbamic acid tert-butyl ester (Example X-4, 0.26 g, 0.42 mmol) were combined in 12 mL of THF, to give 0.19 g of 1-[(4-fluorophenyl)-6-fluoro-2,4-dioxo-1,2,3,4-tetrahydropyrido[2,3-d]pyrimidine-7-yl]-carbamic acid tert-butyl ester. This was dissolved in 20 mL of dichloromethane and treated with HCl gas to afford 0.14 g of the title compound as a solid, mp 235–238° C.

EXAMPLE 66

(1α,5α,6α)[3-(1-(4-fluorophenyl)-6-fluoro-3-hydroxy-2,4-dioxo-1,2,3,4-tetrahydro pyrido[2,3-d]pyrimidine-7-yl)-3-aza-bicyclo[3.1.0]hex-6-yl]-carbamic acid tert-butyl ester Using the method of Example 56, 20% Pd/C (30 mg), (1α,5α,6α)[3-(3-Benzyloxy-1-(4-fluorophenyl)-6-fluoro-2,4-dioxo-1,2,3,4-tetrahydropyrido[2,3-d]pyrimidine-7-yl)-3-aza-bicyclo[3.1.0]hex-6-yl]-carbamic acid tert-butyl ester (Example Y-4, 0.19 g, 0.33 mmol) were combined in 25 mL of THF, to give 0.19 g of the title compound as a foam.

The compounds of the current invention were evaluated to demonstrate their desired antibacterial activities and inhibition of bacterial enzymes, and versus the undesired cell cytotoxicity.

Antibacterial assay: The compounds of the present invention were tested against an assortment of Gram negative and Gram positive organisms using standard microtitration techniques (Cohen, et al., *Antimicrob. Agents Chemother.*, 1985;28:766; Heifetz, et al., *Antimicrob. Agents Chemother.*, 1974;6:124). The results of the evaluation are shown in Table 1.

TABLE 1

Antibacterial Activity

Minimum Inhibitory Concentrations μg/mL

| | Gram Negatives | | | Gram Positives | | |
|---|---|---|---|---|---|---|
| Example Number | E. coli MC4100 | E. coli B90 | E. coli Tol C | B. subtilis RB1 | S. aureus 29213 | S. pyogenes C203 |
| 1 | >64 | 2.0 | 1.0 | 4.0 | 32 | 32 |
| 2 | 16 | 4.0 | 2.0 | 16 | >64 | >64 |
| 3 | >64 | 4.0 | 2.0 | 8.0 | >64 | >64 |
| 4 | >64 | 16 | 16 | 8.0 | 64 | 64 |
| 6 | 64 | 8.0 | 8.0 | 32 | 64 | 16 |
| 7 | 16 | 4.0 | 8.0 | >64 | >64 | >64 |
| 9 | 16 | 4.0 | 2.0 | 16 | 16 | 8.0 |
| 14 | 64 | 4.0 | 1.0 | — | 32 | 64 |

TABLE 1-continued

Antibacterial Activity

Minimum Inhibitory Concentrations μg/mL

| | Gram Negatives | | | Gram Positives | | |
|---|---|---|---|---|---|---|
| Example Number | E. coli MC4100 | E. coli B90 | E. coli Tol C | B. subtilis RB1 | S. aureus 29213 | S. pyogenes C203 |
| 17 | >64 | 64 | 32 | — | >64 | 32 |
| 23 | >64 | 32 | 32 | — | 32 | 32 |
| 28 | >64 | 2.0 | 2.0 | — | 32 | 32 |
| 32 | >64 | 0.5 | 0.5 | — | 8.0 | 64 |
| 36 | 8.0 | 2.0 | 2.0 | — | 64 | 32 |
| 38 | 8.0 | 0.1 | 0.1 | 0.25 | 1.0 | 16 |
| 39 | 1.0 | 0.3 | 0.25 | 2.0 | 32 | 4.0 |
| 42 | 1.0 | 0.25 | 0.25 | — | 4.0 | 2.0 |
| 44 | >64 | 1.0 | 1.0 | — | 4.0 | 32 |
| 46 | 8.0 | 2.0 | 1.0 | — | >64 | 32 |
| 56 | 16 | 0.13 | 0.13 | — | 8.0 | 8.0 |

DNA gyrase assay: The effects of test agents on the activity of DNA gyrase was determined by the supercoiling inhibition assay, following reaction conditions recommended by the enzyme supplier (Lucent, Ltd., Leicester, UK), as follows. Reactions were performed in buffer G (35 mM Tris-HCl (pH 7.5), 24 mM KCl, 4 mM $MgCl_2$, 2 mM DTT, 1.8 mM spermidine, 1 mM ATP, 0.1 mg/mL bovine serum albumin). 0.25 μg of relaxed plasmid pBR322 (Lucent, Ltd., Leicester, UK) was reacted with 1 U *E. coli* gyrase (Lucent, Ltd., Leicester, UK), in the absence or presence of drugs, for 30 minutes at 37° C. Reactions were stopped by the addition of SDS and proteinase K to respective final concentrations of 1% and 0.5 mg/mL. After an additional 30 minutes at 37° C., one-tenth volume of 10×loading buffer (0.3% bromophenol blue, 16% Ficoll, 10 mM $Na_2HPO_4$) was added, and reactions were loaded onto agarose gels and electrophoresed as described above for intercalation assays. The concentration of drug inhibiting 50% of the supercoiling activity of DNA gyrase is given as an $IC_{50}$ and recorded in Table 2.

TABLE 2

Inhibitory Activities vs DNA Gyrase and Topoismerase IV

| Example Number | Gyrase $IC_{50}$ (μM) | DNA TopIV $IC_{50}$ (μM) |
|---|---|---|
| 2 | 22 | >100 |
| 6 | 5.5 | 59 |
| 7 | >100 | 49 |
| 9 | 15.5 | >100 |
| 14 | 46 | — |
| 23 | 36 | >100 |
| 32 | 6.4 | >100 |
| 38 | 6.6 | 57 |
| 39 | 2.4 | 9 |
| 42 | 0.76 | 28 |
| 44 | 12 | >100 |
| 46 | 8.3 | — |

Topoisomerase IV assay: Topoisomerase IV was purified from *E. coli* overexpressing strains, and the compounds were assayed according to literature conditions (*Journal of Biological Chemistry*, 1993;268(32):24481). The k-DNA decatenation assay was used. Briefly, reactions were performed in buffer R (40 mM Tris-HCl (pH 7.5),6 mM $MgCl_2$, 10 mM DTT, 100 mM potassium glutamate, 40 μM ATP, 50 μg/mL bovine serum albumin, 10 mM NaCl). Two-tenths microgram of kinetoplast DNA (k-DNA; TopoGen, Columbus, Ohio) was incubated with 5 ng of *E. coli* Topoisomerase IV in the presence or absence of test compounds for 10 minutes at 37° C. Subsequently, one-tenth volume of 10×gel loading buffer (0.3% bromophenol blue, 16% Ficoll, 10 mM $Na_2HPO_4$) was added, and samples were loaded onto horizontal 0.8% agarose gels prepared with TBE buffer and containing 0.05 μg/mL of ethidium bromide. Electrophoresis was at 70 V for 2 to 4 hours. Gels were then examined by exposure to UV light. The concentration of drug inhibiting 50% of the decantenating activity of Topoisomerase IV is given as an $IC_{50}$ and recorded in Table 2.

Mammalian Cell Cytotoxicity: Compounds were also evaluated in the mammalian cell cytotoxicity assay following the procedures of Suto, et al., (*J. Med Chem.*, 1992;35:4745) and Ciaravino, et al., (*Mutation Res.*, 1993;298:227). The cytotoxicity was determined in Chinese hamster V79 cells. The cells were grown overnight and treated with drug for 3 hours at 37° C., at which time the compound containing media was replaced with fresh media. The cells were then incubated for 5 days and examined for colony formation. The concentration of the drug inhibiting colony formation by 50% is represented by the $IC_{50}$ and is recorded in Table 3.

TABLE 3

Cytotoxicity to Mammalian Cells

| Example Number | 50% Cytotoxic Conc. in CHO Cells (μg/mL) |
|---|---|
| 2 | 177 |
| 3 | 176 |

The quinolone mimics described in this invention display Gram-negative and -positive activity. The compounds also show inhibition of bacterial DNA gyrase/DNA Top IV.

Finally, the compounds are not highly cytotoxic to mammalian cells indicating selectivity for bacteria.

What is claimed is:

1. A compound of Formula I

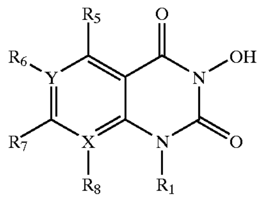

I or a pharmaceutically acceptable salt thereof wherein:

$R_1$ is H, a straight or branched alkyl of 1 to 6 carbons, cycloalkyl of 3 to 6 carbons, a heterocycle of 4 to 6 atoms having 1 to 2 heteroatoms, or a phenyl group, each is optionally substituted by R, F, Cl, OR, or $N(R)_2$ wherein R is H, a straight or branched alkyl of 1 to 6 atoms having 0 to 1 degrees of unsaturation, a ring of 3 to 6 atoms having 0 to 2 heteroatoms, or a phenyl group, each may be substituted by F, Cl, CN, $NO_2$, OH, $NH_2$; also, two R's may form a 3- to 7-membered ring with the atom to which it is attached which ring may have 0 to 1 heteroatoms;

$R_5$ and $R_6$ are each independently H, F, Cl, Br, $NO_2$, CN, $CF_3$, $(C(R)_2)_n$OR, $(C(R)_2)_nCO_2R$, $(C(R)_2)_nCON(R)_2$, $(C(R)_2)_nN(R)_2$, $(C(R)_2)_n$NRCOR, a straight or branched alkyl of 1 to 4 carbons containing 0 to 1 degrees of unsaturation, a cycloalkyl of 3 to 6 carbons, each optionally substituted by F, Cl, OR, or $N(R)_2$ wherein R is as defined above;

$R_7$ is selected from F, Cl, Br, $NO_2$, CN, $CF_3$, $(C(R)_2)_n$OR, $(C(R)_2)_nCO_2R$, $(C(R)_2)_nCON(R)_2$, $(C(R)_2)_nN(R)_2$, $(C(R)_2)_n$NRCOR, a straight or branched alkyl of 1 to 4 carbons containing 0 to 1 degrees of unsaturation, a cycloalkyl of 3 to 6 carbons, each optionally substituted by F, Cl, OR, or $N(R)_2$ wherein R is as defined above, a phenyl, or a heterocyclic ring of 4 to 7 atoms, a fused heterocyclic ring of 8 to 10 atoms, a bicyclic heterocycle of 6 to 9 atoms, or a spiro heterocycle of 7 to 12 atoms each having 1 to 4 heteroatoms, and each of which is optionally substituted by one or more of R, F, Cl, $(C(R)_2)_nN(R)_2$, $(C(R)_2)_n$OR, O, $(C(R)_2)_nCON(R)_2$, $(C(R)_2)_n$COR, $(C(R)_2)_n$NRCOR, $(C(R)_2)_nCO_2R$, wherein R is defined above; any of the adjacent groups $R_5$–$R_8$ may together form a 5- to 7-membered ring having 0 to 2 heteroatoms, which rings may be substituted by any of the groups described for $R_7$; and n is an integer of from 0 to 3.

2. A compound according to claim 1 wherein:

$R_1$ is methyl, ethyl, cyclopropyl, t-butyl, 2-fluorocyclopropyl, 1- or 2-methylcyclopropyl, cyclopropylmethyl, CH═$CH_2$, 4-fluorophenyl, or 2,4-difluorophenyl;

R is H, a straight or branched alkyl of 1 to 6 atoms, a ring of 3 to 6 atoms having 0 to 2 heteroatoms, or a phenyl group, each may be substituted by F, Cl, OH, $NH_2$; alternatively two R's may form a 3- to 7-membered ring having 0 or 1 heteroatom;

$R_5$, and $R_6$, are each independently H, F, Cl, Br, $NO_2$, CN, $CF_3$, CH═$CH_2$, $(C(R)_2)_n$OR, $(C(R)_2)_nCO_2R$, $(C(R)_2)_nCON(R)_2$, $(C(R)_2)_nN(R)_2$, $(C(R)_2)_n$NRCOR, a straight or branched alkyl of 1 to 4 carbons, a cycloalkyl of 3 to 6 carbons wherein the alkyl or cycloalkyl is optionally substituted by F, Cl, OR, or $N(R)_2$;

$R_7$ is selected from F, Cl, Br, $NO_2$, CN, $CF_3$, $(C(R)_2)_n$OR, $(C(R)_2)_nCO_2R$, $(C(R)_2)_nCON(R)_2$, $(C(R)_2)_nN(R)_2$, $(C(R)_2)_n$NRCOR, a straight or branched alkyl of 1 to 4 carbons containing 0 to 1 degrees of unsaturation, a cycloalkyl of 3 to 6 carbons, each optionally substituted by F, Cl, OR, or $N(R)_2$ wherein R is as defined above, a heterocyclic ring of 4 to 7 atoms, a fused heterocyclic ring of 8 to 10 atoms or a bicyclic heterocycle of 6 to 9 atoms, each having 1 to 4 heteroatoms, and each of which may be substituted by one or more of R, F, Cl, $(C(R)_2)_nNR_2$, $(C(R)_2)_n$OR, O, $(C(R)_2)_nCONR_2$, $(C(R)_2)_n$COR, $(C(R)_2)_n$NRCOR, $(C(R)_2)_nCO_2R$, wherein R is H, a straight or branched alkyl of 1 to 6 atoms having 0 to 1 degrees of unsaturation, a ring of 3 to 6 atoms having 0 to 2 heteroatoms, or a phenyl group, each may be substituted by F, Cl, CN, $NO_2$, OH, $NH_2$; also, two R's may form a 3- to 7-membered ring with the atom to which it is attached which ring may have 0 to 1 heteroatoms; and n is an integer of from 0 to 3.

3. A compound according to claim 1 wherein:

any of the adjacent groups $R_5$–$R_8$ may together form a 5- to 7-membered ring having 0 or 1 heteroatom and such rings may be substituted by any of the groups described for $R_7$;

n is 0 to 3; and

R is H, a straight or branched alkyl of 1 to 4 carbons, a ring of 3 to 6 atoms having 0 to 2 heteroatoms or a phenyl, each may be optionally substituted by F, Cl, OH, CN, $NO_2$, or $NH_2$.

4. A compound according to claim 1 wherein:

$R_1$ is ethyl, cyclopropyl, 2-fluorocyclopropyl, cyclopropylmethyl, t-butyl, or phenyl optionally substituted by F, Cl, OR, or $N(R)_2$;

R is H, methyl, ethyl, isopropyl, t-butyl, or phenyl;

R is methyl, ethyl, phenyl, or a 2, 3, or 4-pyridyl each of which may be substituted with F, Cl, $CH_3$, $(CH_2)_nN(R)_2$, or OR;

$R_5$, and $R_6$ are each independently selected from H, F, Cl, Br, $CH_3$, $NH_2$, $CH{=}CH_2$, $NO_2$, and $OCH_3$;

$R_7$ is selected from $R_5$, and $R_6$ a heterocyclic ring of 4 to 7 atoms, a fused heterocyclic ring of 8 to 10 atoms or a bicyclic heterocycle of 6 to 9 atoms, each having 1 to 4 heteroatoms, and each of which may be substituted by one or more of R, F, Cl, $(C(R)_2)_nNR_2$, $(C(R)_2)_nOR$, O, $(C(R)_2)_nCON(R)_2$, $(C(R)_2)_nCOR$, $(C(R)_2)_nNRCOR$, $(C(R)_2)_nCO_2R$, a straight or branched alkyl of 1 to 4 atoms, or a phenyl group which may also be substituted as described above; and n is an integer from 0 to 3.

5. A compound according to claim 1 wherein:

$R_1$ is ethyl, cyclopropyl, t-butyl, or phenyl, optionally substituted by F, Cl, OR, or $NR_2$;

$R_5$ and $R_6$ are each independently selected from H, F, Cl, Br, $CH_3$, $NH_2$, $NO_2$, and $OCH_3$;

$R_7$ is a 5- or 6-membered ring heterocycle, having 1 to 2 heteroatoms, optionally substituted by $(C(R)_2)_nN(R)_2$; a [4.3.0]-bridged heterocycle with 1 to 2 heteroatoms, optionally substituted by $(C(R)_2)_nN(R)_2$; a [3.1.0]-bridged heterocycle having 1 heteroatom, optionally substituted by $(C(R)_2)_nN(R)_2$; a bridged heterocycle of 7 to 9 atoms having 1 to 3 heteroatoms, or a spiro heterocycle of 7 to 12 atoms having 1 to 2 heteroatoms optionally substituted by $(C(R)_2)_nN(R)_2$, which heterocycles may also be substituted by R, F, Cl, or OH;

n is an integer from 0 to 3;

R is H, a straight or branched alkyl of 1 to 6 atoms, which may be substituted by F, Cl, OH, $NH_2$; alternatively two R's may form a 3- to 7-membered ring having 0 to 2 additional heteroatoms; and R is a straight or branched alkyl of 1 to 4 carbons, a phenyl or a heterocycle of 5 or 6 atoms with 1 or 2 heteroatoms optionally substituted by F, Cl, OH, CN, $NO_2$, or $(CH_2)_nN(R)_2$; also, two R's may form a cyclobutyl or a cyclobutyl ring.

6. A compound according to claim 1 wherein:

$R_1$ is ethyl, cyclopropyl, cyclopropylmethyl, t-butyl, or phenyl, optionally substituted by F, Cl, OR, or $N(R)_2$; adjacent groups $R_5$–$R_8$ form a 5- or 6-membered ring having 1 to 2 heteroatoms and which may be substituted by any of the groups described above for $R_7$;

n is 0 to 1; and

R is H, a straight or branched alkyl of 1 to 4 carbons, a ring of 3 to 6 atoms having 0 to 2 heteroatoms or a phenyl, optionally substituted by F, Cl, OH, CN, $NO_2$, or $NH_2$.

7. A compound according to claim 1 wherein:

R is H, a straight or branched alkyl of 1 to 3 atoms or phenyl optionally substituted by F, Cl, OH, or $NH_2$;

$R_5$ and $R_6$ are each independently H, F, Cl, Br, $NO_2$, $NH_2$, $CH_3$, $CHCH_2$ or $R_5$ and $R_6$ may form a ring of 5 to 7 atoms having 0 to 2 heteroatoms;

$R_7$ is selected from $R_5$, $R_6$, cyclopropane, cyclobutane, cyclopentane, cyclohexane, a heterocyclic ring of 4 to 7 atoms, a fused heterocyclic ring of 8 to 10 atoms, or a bicyclic heterocycle of 6 to 9 atoms, each having 1 to 4 heteroatoms, and each of the above may be optionally substituted by one or more of R, F, Cl, $(CR_2)_nN(R)_2$, $(CR_2)_nOR$, or O, wherein R is methyl, ethyl, isopropyl, phenyl, a heterocycle of 5 to 6 atoms having 1 to 2 heteroatoms, each of which may be substituted by F, Cl, $CH_3$, $(CH_2)_nN(R)_2$, or OR; and n is an integer of 0 to 3.

8. A compound according to claim 1 wherein:

$R_1$ is ethyl, cyclopropyl, cyclopropylmethyl, or fluorocyclopropyl;

R is H, ethyl, propyl, isopropyl or phenyl, each optionally substituted with F, Cl, OH, or $NH_2$;

$R_5$, and $R_6$ are each independently H, F, Cl, Br, $NO_2$, methyl, ethyl, ethylene;

$R_7$ is a carbocycle of 3 to 6 atoms, a heterocycle of 5 to 6 atoms having 1 to 2 heteroatoms, a fused heterocycle having 9 atoms and 2 heteroatoms, a bicyclic heterocycle of 6 to 8 atoms having 1 to 2 heteroatoms, each of which may be substituted by one or more of R, F, $N(R)_2$, $CH_2N(R)_2$, $CH_2CH_2N(R)_2$, $CH(CH_3)N(R)_2$, $C(CH_3)_2N(R)_2$, $CH_2OH$, $CH_2CH_2OH$, or OH, wherein R is methyl, ethyl, or phenyl optionally substituted by any of the above.

9. A compound according to claim 1 wherein:

$R_1$ is ethyl, cyclopropyl, cyclopropylmethyl, t-butyl, or phenyl, optionally substituted by F, OH, or $NR_2$;

R is H, methyl, or ethyl;

R is methyl, ethyl, phenyl, a heterocycle of 5 to 6 atoms containing 1 to 2 heteroatoms, each of which may be substituted by F, Cl, $CH_3$, $(CH_2)_nN(R)_2$, or OR;

$R_5$ is H, F, or $NH_2$;

$R_6$ is H, F, Cl, Br, $OCH_3$, $CH{=}CH_2$, or $NO_2$;

$R_7$ is a 5- or 6-membered ring heterocycle, having 1 to 2 heteroatoms, optionally substituted by $(C(R)_2)_nN(R)_2$; a [4.3.0]-bridged heterocycle, with 1 to 2 heteroatoms, which may be optionally substituted by $(C(R)_2)_nN(R)_2$; a [3.1.0]-bridged heterocycle, having 1 heteroatom, which may be optionally substituted by $(C(R)_2)_nN(R)_2$; a bridged heterocycle of 7 to 9 atoms having 1 to 3 heteroatoms, which may be optionally substituted by $(C(R)_2)_nNR_2$, which heterocycles may also be substituted by R, F, Cl, or OH; and n is 0 to 1.

10. A compound according to claim 1 wherein $R_7$ is selected from:

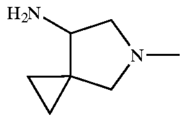
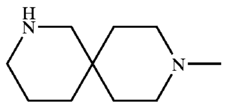

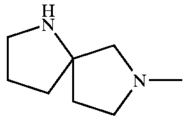
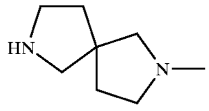

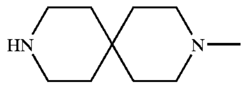
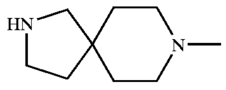

-continued

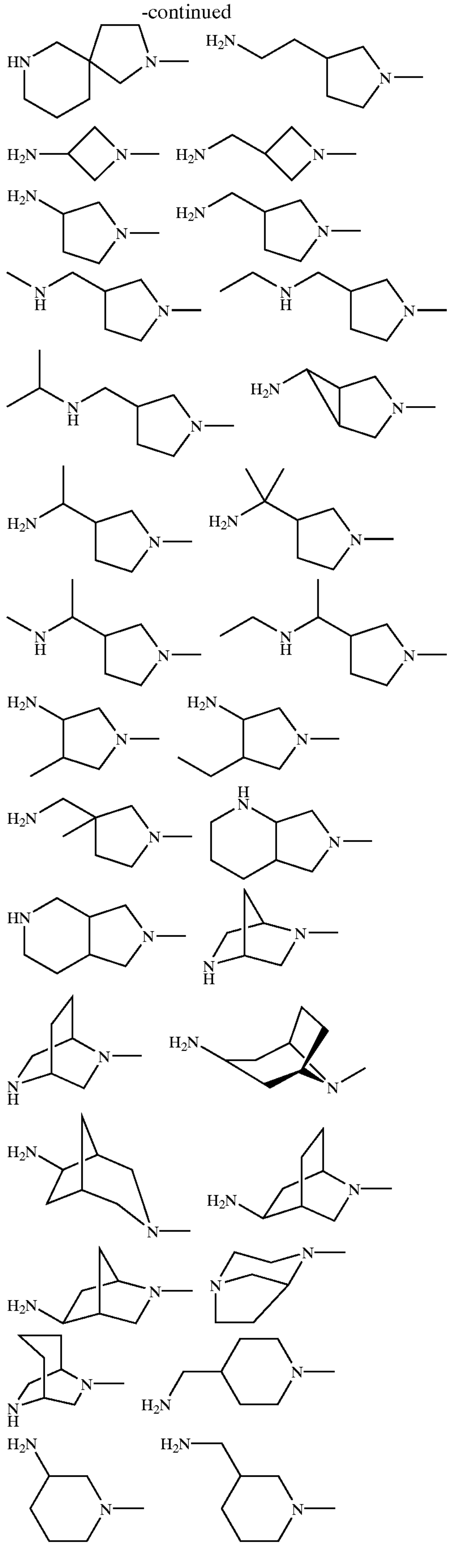

-continued

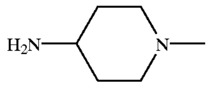 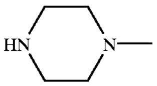

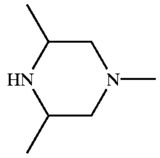 and 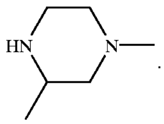.

wherein the NH or $NH_2$'s may be substituted with methyl or ethyl.

11. A compound according to claim 1 selected from:

1-Cyclopropyl-6-fluoro-3-hydroxy-7-pyrrolidin-1-yl-1H-pyrido[2,3-d]pyrimidine-2,4-dione;

1-Cyclopropyl-6-fluoro-3-hydroxy-7-(4-methylpiperazin-1-yl)-1H-pyrido[2,3-d]pyrimidine-2,4-dione, hydrochloride;

1-Ethyl-6-fluoro-3-hydroxy-7-pyrrolidin-1-yl-1H-pyrido[2,3-d]pyrimidine-2,4-dione;

1-Ethyl-6-fluoro-3-hydroxy-7-(4-methylpiperazin-1-yl)-1H-pyrido[2,3-d]pyrimidine-2,4-dione;

7-(3-Aminopyrrolidin-1-yl)-1-ethyl-6-fluoro-3-hydroxy-1H-pyrido[2,3-d]pyrimidine-2,4-dione, trifluoroacetate;

1-Benzyl-6-fluoro-3-hydroxy-7-pyrrolidin-1-yl-1H-pyrido[2,3-d]pyrimidine-2,4-dione;

8-Fluoro-5-hydroxy-9-pyrrolidin-1-yl-2,3-dihydro-1-thia-3a,5-diaza-phenalene-4,6-dione;

6-Fluoro-1-(4-fluorophenyl)-3-hydroxy-7-pyrrolidin-1-yl-1H-pyrido[2,3-d]pyrimidine-2,4-dione;

1-Butyl-6-fluoro-3-hydroxy-7-pyrrolidin-1-yl-1H-pyrido[2,3-d]pyrimidine-2,4-dione;

6-Fluoro-3-hydroxy-7-pyrrolidin-1-yl-1-(4-trifluoromethylphenyl)-1H-pyrido[2,3-d]pyrimidine-2,4-dione;

1-(2,4-Difluorophenyl)-6-fluoro-3-hydroxy-7-pyrrolidin-1-yl-1H-pyrido[2,3-d]pyrimidine-2,4-dione;

6-Fluoro-3-hydroxy-1-(4-methylphenyl)-7-pyrrolidin-1-yl-1H-pyrido[2,3-d]pyrimidine-2,4-dione;

6-Fluoro-3-hydroxy-7-pyrrolidin-1-yl-1-(3-trifluoromethylphenyl)-1H-pyrido[2,3-d]pyrimidine-2,4-dione;

1-(2-Fluorophenyl)-6-fluoro-3-hydroxy7pyrrolidin-1-yl-1H-pyrido[2,3-d]pyrimidine-2,4-dione;

6-Fluoro-3-hydroxy-1-(4-methoxyphenyl)-7-pyrrolidin-1-yl-1H-pyrido[2,3-d]pyrimidine-2,4-dione;

1-(4-Fluorophenyl)-6-fluoro-3-hydroxy-7-(3-amino-pyrrolidin-1-yl-1H-pyrido[2,3-d]pyrimidine-2,4-dione, hydrochloride; and 7-(6-Amino-3-aza-bicyclo[3.1.0]hex-3-yl)-1-cyclopropyl-6-fluoro-3-hydroxy-1H-pyrido[2,3-d]pyrimidine-2,4-dione.

12. A pharmaceutical composition comprising a therapeutically effective amount of a compound according to claim 1 and a pharmaceutically acceptable carrier.

13. A method for treating bacterial infections in a mammal comprising administering to said mammal a therapeutically effective amount of a compound according to claim 1.

14. A compound selected from:

3-Benzyloxy-7-chloro-1-ethyl-6-fluoro-1H-pyrido[2,3-d]pyrimidine-2,4-dione;

3-Benzyloxy-1-butyl-7-chloro-6-fluoro-1H-pyrido[2,3-d]pyrimidine-2,4-dione;

1-Benzyl-3-benzyloxy-7-chloro-6-fluoro-1H-pyrido[2,3-d]pyrimidine-2,4-dione;

3-Benzyloxy-7-chloro-6-fluoro-1-(4-fluorophenyl)-1H-pyrido[2,3-d]pyrimidine-2,4-dione;

3-Benzyloxy-7-chloro-6-fluoro-1-(2-fluorophenyl)-1H-pyrido[2,3-d]pyrimidine-2,4-dione;

3-Benzyloxy-7-chloro-1-(2,4-difluorophenyl)-6-fluoro-1H-pyrido[2,3-d]pyrimidine-2,4-dione;

3-Benzyloxy-7-chloro-6-fluoro-1-(4-methylphenyl)-1H-pyrido[2,3-d]pyrimidine-2,4-dione;

3-Benzyloxy-7-chloro-6-fluoro-1-(4-trifluoromethylphenyl)-1H-pyrido[2,3-d]pyrimidine-2,4-dione;

3-Benzyloxy-7-chloro-6-fluoro-1-(3-trifluoromethylphenyl)-1H-pyrido[2,3-d]pyrimidine-2,4-dione; and 3-Benzyloxy-7-chloro-6-fluoro-1-(4-methoxyphenyl)-1H-pyrido[2,3-d]pyrimidine-2,4-dione.

15. A compound selected from:

3-Benzyloxy-1-cyclopropyl-6-fluoro-7-pyrrolidinyl-1H-pyrido[2,3-d]pyrimidine-2,4-dione;

3-Benzyloxy-1-cyclopropyl-6-fluoro-7-(4-methylpiperazinyl)-1H-pyrido[2,3-d]pyrimidine-2,4-dione;

3-Benzyloxy-1-ethyl-6-fluoro-7-pyrrolidinyl-1H-pyrido[2,3-d]pyrimidine-2,4-dione;

3-Benzyloxy-1-ethyl-6-fluoro-7-(4-methylpiperazinyl)-1H-pyrido[2,3-d]pyrimidine-2,4-dione;

3-Benzyloxy-1-ethyl-6-fluoro-7-[3-(N-tert-butoxycarbonylamino)pyrrolidin-1-yl]-1H-pyrido[2,3-d]pyrimidine-2,4-dione; and 1-Benzyl-3-benzyloxy-6-fluoro-7-pyrrolidinyl-1H-pyrido[2,3-d]pyrimidine-2,4-dione.

* * * * *